US007598077B2

(12) United States Patent
Horikawa et al.

(10) Patent No.: US 7,598,077 B2
(45) Date of Patent: Oct. 6, 2009

(54) COMPOSITIONS AND METHODS FOR ENHANCING DIFFERENTIAL EXPRESSION

(75) Inventors: Izumi Horikawa, Rockville, MD (US); J. Carl Barrett, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1216 days.

(21) Appl. No.: 10/456,830

(22) Filed: Jun. 5, 2003

(65) Prior Publication Data

US 2004/0248246 A1    Dec. 9, 2004

(51) Int. Cl.
*C12N 15/85* (2006.01)
*C07H 21/04* (2006.01)
(52) U.S. Cl. .................. 435/320.1; 536/23.2; 435/455; 435/325
(58) Field of Classification Search .............. 435/320.1, 435/455, 325; 536/23.1
See application file for complete search history.

(56) References Cited

U.S. PATENT DOCUMENTS

| | | | |
|---|---|---|---|
| 5,891,639 | A | 4/1999 | Harley et al. |
| 5,972,605 | A | 10/1999 | Villeponteau et al. |
| 6,054,575 | A | 4/2000 | Villeponteau et al. |
| 6,258,535 | B1 | 7/2001 | Villeponteau et al. |
| 6,261,556 | B1 | 7/2001 | Weinrich et al. |
| 6,300,110 | B1 | 10/2001 | Villeponteau et al. |
| 6,320,039 | B1 | 11/2001 | Villeponteau et al. |
| 6,337,200 | B1 | 1/2002 | Morin |
| 6,372,742 | B1 | 4/2002 | Chin et al. |
| 6,391,554 | B1 | 5/2002 | West et al. |
| 6,777,203 | B1 * | 8/2004 | Morin et al. ............... 435/69.1 |
| 2002/0028785 | A1 | 3/2002 | Wold et al. |
| 2005/0048466 | A1 * | 3/2005 | Qian et al. .................... 435/5 |

FOREIGN PATENT DOCUMENTS

| | | | |
|---|---|---|---|
| CN | WO/2003/006640 | * | 1/2003 |
| WO | WO 00/46355 | | 8/2000 |
| WO | WO 02/42468 | | 5/2002 |

OTHER PUBLICATIONS

Li et al Nat Biotechnol. 1999;17(3):241-5.*
Oskouian et al Biochem J, 1997, 324, 113-121.*
Iyer and Struhl The EMBO Jornal vol. 14, 2570-2579, 1995.*
Cong et al., "Histone deacetylation is involved in the transcriptional repression of hTERT in normal human cells," *J. Biol. Chem.* 275(46):35665-35668, Nov. 17, 2000.
Cong et al., "The human telomerase catalytic subunit hTERT: Organization of the gene and characterization of the promoter," *Hum. Mol. Gen.* 8(1):137-142, 1999.
D'Costa et al., "Human immunodeficiency virus type 2 lentiviral vectors: packaging signal and splice donor in expression and encapsidation," *J. Gen. Virol.* 82:425-434, 2001.
Farwell et al., "Genetic and epigenetic changes in human epithelial cells immortalized by telomerase," *Am. J. Virol.*,156(5):1537-1547, May 2000.
Fujimoto et al., "Identification and characterization of negative regulatory elements of the human telomerase catalytic subunit (hTERT) gene promoter: possible role of MZF-2 in transcriptional repression of hTERT," *Nuc. Acids Res.* 28(13):2557-2562, 2000.
Gu et al., "Tumor-specific transgene expression from the human telomerase reverse transcriptase promoter enables targeting of the therapeutic effects of the *Bax* gene to cancers," *Cancer Res.* 60:5359-5364, Oct. 1, 2000.
Günes et al., "Expression of *hTERT* gene is regulated at the level of transcriptional initiation and repressed by Mad1," *Cancer Res.*, 60:2116-2121, Apr. 15, 2000.
Horikawa et al., "Cloning and characterization of the promoter region of *human telomerase reverse transcriptase* gene," *Cancer Res.*, 59:826-830, Feb. 15, 1999.
Horikawa et al., "Downstream E-box-mediated regulation of the human telomerase reverse transcriptase (*hTERT*) gene transcription: Evidence for an endogenous mechanism of transcriptional repression," *Mol. Biol. Cell* published online Jun. 6, 2002, 10.1091/mbc.E01-11-0107.
Horikawa et al., "Multiple mechanisms in the transcriptional regulation of the human telomerase reverse transcriptase (hTERT) gene," *Am. Assoc. Cancer Res.* $91^{st}$ Annual Meeting, Apr. 1-5, 2000. (abstract only).
Horikawa et al., "Transcriptional regulation of the telomerase *hTERT* gene as a target for cellular and viral oncogenic mechanisms," *Carcin. Adv. Acc.* pp. 1-24, May 22, 2003.
Keith et al., "Telomerase-directed molecular therapeutics," *Exp. Rev. Mol. Med.* pp. 1-22, Apr. 22, 2002.
Koch et al., "Augmenting transgene expression from carcinoembryonic antigen (CEA) promoter via a GAL4 gene regulatory system," *Mol. Ther.* 3(3):278-283, Mar. 2001. (abstract only).
Koga et al., "A novel telomerase-specific gene therapy: Gene transfer of Caspase-8 utilizing the human telomerase catalytic subunit gene promoter," *Hum. Gene Ther.* 11:1397-1406, Jul. 1, 2000.
Komata et al., "Treatment of malignant glioma cells with the transfer of constitutively active Caspase-6 using the human telomerase catalytic subunit (human telomerase reverse transcriptase) gene promoter," *Cancer Res.*, 61:5796-5802, Aug. 1, 2001.

(Continued)

*Primary Examiner*—Valarie Bertoglio
*Assistant Examiner*—Anoop Singh
(74) *Attorney, Agent, or Firm*—Klarquist Sparkman, LLP

(57) ABSTRACT

Artificial TERT promoters, which are useful for enhancing the differential expression of operably linked heterologous nucleic acid sequences, such as polypeptide cytotoxins, are disclosed herein. Methods for treating disease cells, such as cancer cells, while minimizing effects on normal, somatic cells by administering therapeutically effective amounts of heterologous nucleic acid sequences operably linked to artificial TERT promoters are provided. Kits containing artificial TERT promoters for enhancing differential expression are also provided.

17 Claims, 13 Drawing Sheets

OTHER PUBLICATIONS

Kyo et al., "Sp1 cooperates with c-Myc to activate transcription of the human telomerase reverse transcriptase gene (hTERT)," *Nuc. Acids Res.* 28(3): 669-677, 2000.

Lee et al., "Human Papillomavirus E2 Down-regulates the Human Telomerase Reverse Transcriptase Promoter," *J. Biol. Chem.* 277(31):27748-27756, Aug. 2, 2002.

Leem et al., "The human telomerase gene: complete genomic sequence and analysis of tandem repeat polymorphisms in intronic regions," *Oncogene* 21(5):769-77, Jan. 24, 2002. (abstract only).

Lin et al., "Targeted expression of green fluorescent protein/tumor necrosis factor-related apoptosis-inducing ligand fusion protein from human telomerase reverse transcriptase promoter elicits antitumor activity without toxic effects on primary human hepatocytes," *Cancer Res.* 62:3620-3625, Jul. 1, 2002.

Majumdar et al., "The telomerase reverse transcriptase promoter drives efficacious tumor suicide gene therapy while preventing hepatotoxicity encountered with constitutive promoters," *Gene Ther.* 8:568-578, 2001.

Misiti et al., "Induction of hTERT expression and telomerase activity by estrogens in human ovary epithelium cells," *Mol. Cell Biol.* 20(11):3764-3771, Jun. 2000.

Nettelbeck et al., "Gene therapy designer promoters for tumour targeting," *TIG*, 16(4):174-181, Apr. 2000.

Nielsen et al., "Murine helix-loop-helix transcriptional activator proteins binding to the E-box motif of the Akv murine leukemia virus enhancer identified by cDNA cloning," *Mol. Cell Biol.* 12(8):3449-59, Aug. 1992. (abstract only).

Nyanguile et al., "A nonnatural transcriptional coactivator," *Proc. Natl. Acad. Sci. USA* 94:13402-13406, Dec. 1997.

Oh et al., "In vivo and in vitro analyses of Myc for differential promoter activities of the human telomerase (hTERT) gene in normal and tumor cells," *Biochem. Biophys. Res. Comm.* 263:361-365, 1999.

Oh et al., "The Wilms' tumor 1 tumor suppressor gene represses transcription of the human telomerase reverse transcriptase gene," *J. Biol. Chem.* 274(52):37473-37478, Dec. 24, 1999.

Pollock et al., "Transcriptional activation: Is it rocket science?" *Proc. Natl. Acad. Sci. USA* 94:13388-13389, Dec. 1997.

Prowse et al., "Developmental and tissue-specific regulation of mouse telomerase and telomere length," *Proc. Natl. Acad. Sci. USA* 92:4818-4822, May 1995.

Reddel, "The role of senescence and immortalization in carcinogenesis," *Carcinogen.* 21(3):477-484, 2000.

Takakura et al., "Cloning of human telomerase catalytic subunit (hTERT) gene promoter and identification of proximal core promoter sequences essential for transcriptional activation in immortalized and cancer cells," *Cancer Res.* 59:551-557, Feb. 1, 1999.

Wirth et al., "A Telomerase-dependent Conditionally Replicating Adenovirus for Selective Treatment of Cancer," *Cancer Res.* 63:3181-3188, Jun. 15, 2003.

* cited by examiner

Figure 1

```
-1665  ATCATCAGCT TTTCAAAGAC ACACTAACTG CACCCATAAT ACTGGGTGT CTTCTGGGTA TCATTGAATG
-1585  CCGGGAGGCG TTTCCTCGCC ATGCACATGG TGTTAATTAC TCCAGCATAA TCTTCTGCTT CCATTCCTCT
-1505  TTTAAATTG TGTTTTCTAT GTTGGCTTCT CTGCAGAGAA CCAGTGTAAG CTACAACTTA TCTTTTGTTG GAACAAATTT
-1425  TCCAAACCGC CCCTTGCCC TAGTGGCAGA GACAATTCAC AAACACAGCC CTTTAAAAAG GCTTAGGGAT CACTAAGGGG
-1345  ATTTCTAGAA GAGCGACCCG TAATCCTAAG TATTTACAAG ACGAGGCTAA CCTCCAGCGA GCGTGACAGC CCAGGAGGG
-1265  TGCGAGGCCT GTTCAAATGC TAGCTCCATA AATAAAGCAA TTTCCTCCGG CAGTTTCTGA AAGTAGGAAA GGTTACATTT
-1185  AAGGTTGCGT TTGTTAGCAT TTCAGTGTTT GCCGACCTCA GCTACAGCAT CCCTGCAAGG CCTGGGGAGA CCCAGAAGTT
-1105  TCTCGCCCCT TAGATCCAAA CTTGAGCAAC CCGGAGTCTG GATTCCTGGG AAGTCCTCAG CTGTCCTGCG GTTGTGCCGG
-1025  GGCCCCAGGT CTGGAGGGGA CCAGTGGCCG TGTGCTTGGG ACTGGCTGGC GCCTCCTAGC TCTGCAGTCC
 -945  GAGGCTTGGA CCAGGTGCC GAGTGCCGGG TGGACCCCGA GGGCGGGATG TGGAAGTCGG GCCTTCCATT TTGGCTTCAT
 -865  CTGCCAGACA GAGTGCCGGG GCCCAGGGTC AAGCCGTTG GAGGCGCCCG TGACCAGATG GTGCGCGGCC AGCAGGAGCG
 -785  CCTGGCTCCA TTTCCACCCG CCCCAGGGTG GGACCGCCCC GGTGGGTGAT TAACAGATTT GGGGTGTTT GCTCATGGTG
 -705  GGGACCCTC GCCGCTGAG GGACCAGGGA GAGAAATGAC CAAGGAGCCC AAGTCGCGG GAAGTGTTGC
 -625  AGGGAGGCAC TCCGGGAGGT CCCGCAGGGA CGTCCAGGGA CGTCCAGTCG TCCCCAGCCG CGTCTACGCG
 -545  CCTCCGTCCT CCCCTTCACG TCCGGCATTC GTGGTGCCCG GAGCCCGGTC CCCGCGTCC GGACCCTGGAG GCAGCCCTGG
 -465  GTCTCCGGAT CAGGCCAGCC GCCAAAGGGT CGCCGCACGC ACCTGTTCCC AGGGCCTCCA CATCATGGCC CCTCCCTCGG
 -385  GTTACCCCAC AGCTTAGGCC GATTCGACCT CTCTCCGCTG GGGCCCCTGC TGGCGTCCCT GCACCCCTGG AGCGCGAGCG
                          Sp1                    c-Ets-2 bHLHZ
 -305  GCGCGGGC GGGGAAGCAC GGGGCAGACC CCCGGAGTCC CCCGAGCAG CTGCGTGTC GGGCACCACG CGGGCTCCCA
 -225  GTGGATTCGC GGGCACAGAC GCCCAGGACC CGCCTTCCCA CGTGGCGGAG GGACTGGGGA CCCGGGCTGGGC CGTCCTGCCC
                          Sp1                    bHLHZ        AP-2              NF-E2/Sp1
 -145  CTTCACCTTC CAGCTCCGC TCCTCCGCGC GGACCCCGCC CCGTCCCGAC CCGTCCCGG TCCCCGGCCC AGCCCCCTCC
 -65   GGGCCCTCCC AGCCCCTCCC GCGGGCCCCG CCTCTCCCTCG CGGCCGGAGT TTCAGGCAGC GCTGCGTCCT
       MAZ       MAZ/Sp1                Sp1                                       +1
 +16   GCTGCGCACG TGGGAAGCCC CACCCCCGGC CACCCCCGCG ATGCCGCGCG CGTGCGGCGC CCGAGCCGTG CGCTCCCCTG
       bHLHZ     c-Ets-2                                GW2 primer
 +96   TGCGCAGCCA CTACCGCGAA GTGCTGCCGC TGGCCACGTT CGTGCGGCTG CGTGCGGCG AGGGCTGGCG GCTGGTGCAG
 +176  CGCGGGGACC CGGCGCTTT GTGGCCCAGT GTGGCCGCTG GCCTGGTGTG CGTGCCCTGG GACGCACGC CGCGCACGGC
 +256  CGCGGCCTCC TTCCGCCAGg cagcgcaggc cgggtcggc gtccggctgg ggttgagggc ggcggggg aaccagcgac
 +336  atgcggagag gactcagggc gcttcccccg cag
``` pSGT-5 (SDM/RRE2/hTERT-GFP)

LTR: long terminal repeat
◉ : leader sequence with a splice donor site mutated
gag: gag sequence with a stop codon and a frame shift
PPT: poly purine track
RRE2: Rev response element
hTERT: artificial hTERT promoter
GFP: enhanced green fluorescent protein

SEQUENCE LISTING

<160> NUMBER OF SEQ ID NOS: 18

<210> SEQ ID NO 1
<211> LENGTH: 4293
<212> TYPE: DNA
<213> ORGANISM: Homo sapiens
<220> FEATURE:
<221> NAME/KEY: misc_feature
<222> LOCATION: (3545)..(3609)
<223> OTHER INFORMATION: Region identical to HBV integration site in
      huH-4 cell line
<220> FEATURE:
<221> NAME/KEY: protein_bind
<222> LOCATION: (3729)..(3734)
<223> OTHER INFORMATION: Upstream E-box
<220> FEATURE:
<221> NAME/KEY: misc_feature
<222> LOCATION: (3916)..(3916)
<223> OTHER INFORMATION: Major transcription initiation site
<220> FEATURE:
<221> NAME/KEY: 5'UTR
<222> LOCATION: (3916)..(3970)
<223> OTHER INFORMATION: 5' untranslated region of mRNA
<220> FEATURE:
<221> NAME/KEY: protein_bind
<222> LOCATION: (3937)..(3942)
<223> OTHER INFORMATION: Downstream E-box
<220> FEATURE:
<221> NAME/KEY: CDS
<222> LOCATION: (3971)..(4189)
<223> OTHER INFORMATION: Exon 1
<220> FEATURE:
<221> NAME/KEY: primer_bind
<222> LOCATION: (4029)..(4050)
<223> OTHER INFORMATION: GW2 primer binding site
<220> FEATURE:
<221> NAME/KEY: Intron
<222> LOCATION: (4190)..(4293)
<223> OTHER INFORMATION: Intron 1

<400> SEQUENCE: 1

| | | | | | |
|---|---|---|---|---|---|
| tacacactcc | cgtccacgac | cgaccccgc | tgttttattt | taatagctac | aaagcaggga | 60 |
| aatccctgct | aaaatgtcct | ttaacaaact | ggttaaacaa | acgggtccat | ccgcacggtg | 120 |
| gacagttcct | cacagtgaag | aggaacatgc | cgtttataaa | gcctgcaggc | atctcaaggg | 180 |
| aattacgctg | agtcaaaact | gccacctcca | tgggatacgt | acgcaacatg | ctcaaaaaga | 240 |
| aagattttca | ccccatggca | ggggagtggt | tgggggttaa | ggacggtggg | ggcagcagct | 300 |
| gggggctact | gcacgcacct | tttactaaag | ccagtttcct | ggttctgatg | gtattggctc | 360 |
| agttatggga | gactaaccat | aggggagtgg | ggatggggga | acccggaggc | tgtgccatct | 420 |
| ttgccatgcc | cgagtgtcct | gggcaggata | atgctctaga | gatgcccacg | tcctgattcc | 480 |
| cccaaacctg | tggacagaac | ccgcccggcc | ccagggcctt | tgcaggtgtg | atctccgtga | 540 |

```
ggaccctgag gtctgggatc cttcgggact acctgcaggc ccgaaaagta atccaggggt    600
tctgggaaga ggcgggcagg agggtcagag ggggcagcc tcaggacgat ggaggcagtc    660
agtctgaggc tgaaaaggga gggagggcct cgagcccagg cctgcaagcg cctccagaag    720
ctggaaaaag cggggaaggg accctccacg gagcctgcag caggaaggca cggctggccc    780
ttagcccacc agggcccatc gtggacctcc ggcctccgtg ccataggagg gcactcgcgc    840
tgcccttcta gcatgaagtg tgtggggatt tgcagaagca acaggaaacc catgcactgt    900
gaatctagga ttatttcaaa acaaaggttt acagaaacat ccaaggacag ggctgaagtg    960
cctccgggca agggcagggc aggcacgagt gattttattt agctatttta ttttatttac   1020
ttactttctg agacagagtt atgctcttgt tgcccaggct ggagtgcagc ggcatgatct   1080
tggctcactg caacctccgt ctcctgggtt caagcaattc tcgtgcctca gcctcccaag   1140
tagctgggat tcaggcgtg caccaccaca cccggctaat tttgtatttt tagtagagat   1200
gggctttcac catgttggtc aggctgatct caaaatcctg acctcaggtg atccgcccac   1260
ctcagcctcc caaagtgctg ggattacagg catgagccac tgcacctggc ctatttaacc   1320
attttaaaac ttccctgggc tcaagtcaca cccactggta aggagttcat ggagttcaat   1380 ttcccctta ctcaggagtt accctccttt gatattttct gtaattcttc gtagactggg   1440
gatacaccgt ctcttgacat attcacagtt tctgtgacca cctgttatcc catgggaccc   1500
actgcagggg cagctgggag gctgcaggct tcaggtccca gtggggttgc catctgccag   1560
tagaaacctg atgtagaatc agggcgcgag tgtggacact gtcctgaatc tcaatgtctc   1620
agtgtgtgct gaaacatgta gaaattaaag tccatccctc ctactctact gggattgagc   1680
cccttcccta tcccccccca ggggcagagg agttcctctc actcctgtgg aggaaggaat   1740
gatactttgt tattttcac tgctggtact gaatccactg tttcatttgt tggtttgttt   1800
gttttgtttt gagaggcggt ttcactcttg ttgctcaggc tggagggagt gcaatggcgc   1860
gatcttggct tactgcagcc tctgcctccc aggttcaagt gattctcctg cttccgcctc   1920
ccatttggct gggattacag gcacccgcca ccatgcccag ctaattttt gtatttttag   1980 tagagacggg ggtggggtg gggttcacca tgttggccag gctggtctcg aacttctgac   2040
ctcagatgat ccacctgcct ctgcctccta aagtgctggg attacaggtg tgagccacca   2100
tgcccagctc agaatttact ctgtttgaaa catctgggtc tgaggtagga agctcacccc   2160
actcaagtgt tgtggtgttt taagccaatg atagaatttt tttattgttg ttagaacact   2220
cttgatgttt tacactgtga tgactaagac atcatcagct tttcaaagac acactaactg   2280
cacccataat actggggtgt cttctgggta tcagcgatct tcattgaatg ccggaggcg   2340 tttcctcgcc atgcacatgg tgttaattac tccagcataa tcttctgctt ccatttcttc   2400
tcttccctct tttaaaattg tgttttctat gttggcttct ctgcagagaa ccagtgtaag   2460
ctacaactta acttttgttg gaacaaattt tccaaaccgc ccctttgccc tagtggcaga   2520
gacaattcac aaaacagcc ctttaaaaag gcttagggat cactaagggg atttctagaa   2580
gagcgaccyg taatcctaag tatttacaag acgaggctaa cctccagcga gcgtgacagc   2640
ccagggaggg tgcgaggcct gttcaaatgc tagctccata aataaagcaa tttcctccgg   2700
cagtttctga aagtaggaaa ggttacattt aaggttgcgt ttgttagcat tcagtgttt   2760 gccgacctca gctacagcat ccctgcaagg cctcgggaga cccagaagtt tctcgcccct   2820
tagatccaaa cttgagcaac ccggagtctg gattcctggg aagtcctcag ctgtcctgcg   2880
gttgtgccgg ggccccaggt ctggagggga ccagtggccg tgtggcttct actgctgggc   2940
```

```
tggaagtcgg gcctcctagc tctgcagtcc gaggcttgga gccaggtgcc tggaccccga    3000
ggytgccctc caccctgtgc gggcgggatg tgaccagatg ttggcctcat ctgccagaca    3060
gagtgccggg gccagggtc aaggccgttg tggctggtgt gaggcgcccg gtgcgcggcc     3120
agcaggagcg cctggctcca tttcccaccc tttctcgacg ggaccgcccc ggtgggtgat    3180
taacagattt ggggtggttt gctcatggtg gggacccctc gccgcctgag aacctgcaaa    3240
gagaaatgac gggcctgtgt caaggagccc aagtcgcggg gaagtgttgc agggaggcac    3300
tccggggaggt cccgcgtgcc cgtccaggga gcaatgcgtc ctcgggttcg tccccagccg   3360
cgtctacgcg cctccgtcct cccctttcacg tccggcattc gtggtgcccg gagcccgacg   3420
ccccgcgtcc ggacctggag gcagccctgg gtctccggat caggccagcg gccaaagggt    3480
cgccgcacgc acctgttccc agggcctcca catcatggcc cctccctcgg gttaccccac    3540
agcytaggcc gattcgacct ctctccgctg gggcctcgc tggcgtccct gcaccctggg     3600
agcgcgagcg gcgcgcgggc ggggaagcgc ggcccagacc cccgggtccg cccggagcag    3660
ctgcgctgtc ggggccaggc cgggctccca gtggattcgc gggcacagac gcccaggacc    3720
gcgcttccca cgtggcggag ggactgggga cccgggcacc cgtcctgccc cttcaccttc    3780
cagctccgcc tcctccgcgc ggaccccgcc ccgtcccgac ccctcccggg tccccggccc    3840
agccccctcc gggccctccc agccccctcc cttcctttcc gcggccccgc cctctcctcg    3900
cggcgcgagt ttcaggcagc gctgcgtcct gctgcgcacg tgggaagccc tggccccggc    3960
cacccccgcg atg ccg cgc gct ccc cgc tgc cga gcc gtg cgc tcc ctg      4009
             Met Pro Arg Ala Pro Arg Cys Arg Ala Val Arg Ser Leu
              1               5                  10 ctg cgc agc cac tac cgc gag gtg ctg ccg ctg gcc acg ttc gtg cgg     4057
Leu Arg Ser His Tyr Arg Glu Val Leu Pro Leu Ala Thr Phe Val Arg
    15                  20                  25 cgc ctg ggg ccc cag ggc tgg cgg ctg gtg cag cgc ggg gac ccg gcg     4105
Arg Leu Gly Pro Gln Gly Trp Arg Leu Val Gln Arg Gly Asp Pro Ala
 30                  35                  40                  45 gct ttc cgc gcg ctg gtg gcc cag tgc ctg gtg tgc gtg ccc tgg gac     4153
Ala Phe Arg Ala Leu Val Ala Gln Cys Leu Val Cys Val Pro Trp Asp
                 50                  55                  60 gca cgg ccg ccc ccc gcc gcc ccc tcc ttc cgc cag gtgggcctcc          4199
Ala Arg Pro Pro Pro Ala Ala Pro Ser Phe Arg Gln
                 65                  70 ccggggtcgg cgtccggctg gggttgaggg cggccggggg gaaccagcga catgcggaga   4259
gcagcgcagg cgactcaggg cgcttccccc gcag                               4293

<210> SEQ ID NO 2
<211> LENGTH: 73
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
                 20                  25                  30

Pro Gln Gly Trp Arg Leu Val Gln Arg Gly Asp Pro Ala Ala Phe Arg
             35                  40                  45

Ala Leu Val Ala Gln Cys Leu Val Cys Val Pro Trp Asp Ala Arg Pro
         50                  55                  60
```

```
Pro Pro Ala Ala Pro Ser Phe Arg Gln
65                  70

<210> SEQ ID NO 3
<211> LENGTH: 22
<212> TYPE: DNA
<213> ORGANISM: Artificial
<220> FEATURE:
<223> OTHER INFORMATION: Primer GW1

<400> SEQUENCE: 3
agcactcggg ccaccagctc ct                                              22

<210> SEQ ID NO 4
<211> LENGTH: 22
<212> TYPE: DNA
<213> ORGANISM: Artificial
<220> FEATURE:
<223> OTHER INFORMATION: Primer GW2

<400> SEQUENCE: 4
aacgtggcca gcggcagcac ct                                              22

<210> SEQ ID NO 5
<211> LENGTH: 430
<212> TYPE: DNA
<213> ORGANISM: Homo sapiens

<400> SEQUENCE: 5
gtcctgctgc gcacgtggga agccctggcc ccggccaccc ccgcgatgcc gcgcgctccc      60
cgctgccgag ccgtgcgctc cctgctgcgc agccactacc gcgaggtgct gccgctggcc     120
acgttcgtgc ggcggcctgg gccccagggc tggcggctgg tgcagcgcgg ggacccggcg     180
gctttccgcg cgctggtggc ccagtgcctg gtgtgcgtgc cctgggacgc acggccgccc     240
cccgccgccc cctccttccg ccaggtgtcc tgcctgaagg agctggtggc ccgagtgctg     300
cagaggctgt gcgagcgcgg cgcgaagaac gtgctggcct tcggcttcgc gctgctggac     360
ggggcccgcg ggggccccccc cgaggccttc accaccagcg tgcgcagcta cctgcccaac     420
acggtgaccg                                                            430

<210> SEQ ID NO 6
<211> LENGTH: 460
<212> TYPE: RNA
<213> ORGANISM: Artificial
<220> FEATURE:
<223> OTHER INFORMATION: RNAase protection probe
<220> FEATURE:
<221> NAME/KEY: misc_feature
<222> LOCATION: (1)..(70)
<223> OTHER INFORMATION: Derived from pCR2.1 vector

<400> SEQUENCE: 6
gggcgaauug ggcccucuag augcaugcuc gagcggccgc cagugugaug gauaucugca      60
gaauucggcu aacguggcca gcggcagcac cucgcgguag uggcugcgca gcagggagcg     120
cacggcucgg cagcggggag cgcgcggcau cgcggggggug gccggggcca gggcuuccca     180
cgugcgcagc aggacgcagc gcugccugaa acucgcgccg cgaggagagg gcggggccgc     240
ggaaaggaag gggagggggcu gggagggccc ggaggggggcu gggccgggga cccgggaggg     300
gucgggacgg ggcggggucc gcgcggagga ggcggagcug gaaggugaag gggcaggacg     360
ggugcccggg ucccagucc cuccgccacg ugggaagcgc gguccugggc gucugugccc     420
```

-continued

```
gcgaauccac ugggagcccg gccuggcccc gacagcgcag                    460
```

<210> SEQ ID NO 7
<211> LENGTH: 6
<212> TYPE: DNA
<213> ORGANISM: Artificial
<220> FEATURE:
<223> OTHER INFORMATION: E-box Sequence

<400> SEQUENCE: 7

```
cacgtg                                                         6
```

<210> SEQ ID NO 8
<211> LENGTH: 361
<212> TYPE: DNA
<213> ORGANISM: Homo sapiens
<220> FEATURE:
<221> NAME/KEY: misc_feature
<222> LOCATION: (314)..(323)
<223> OTHER INFORMATION: Single Copy Artificial E-Box Insert

<400> SEQUENCE: 8

```
ggtaccgctg cgctgtcggg gccaggccgg gctcccagtg gattcgcggg cacagacgcc    60
caggaccgcg cttcccacgt ggcggaggga ctggggaccc gggcacccgt cctgcccctt   120
caccttccag ctccgcctcc tccgcgcgga ccccgccccg tcccgacccc tcccgggtcc   180
ccggcccagc cccctccggg ccctcccagc ccctccccctt cctttccgcg gccccgccct   240
ctcctcgcgg cgcgagtttc aggcagcgct gcgtcctgct gcgcacgtgg gaagccctgg   300
ccgatgggct cgacgcacgt gggagcttgg cattccggta ctgttggtaa agccaccatg   360
g                                                                  361
```

<210> SEQ ID NO 9
<211> LENGTH: 381
<212> TYPE: DNA
<213> ORGANISM: Homo sapiens
<220> FEATURE:
<221> NAME/KEY: misc_feature
<222> LOCATION: (314)..(343)
<223> OTHER INFORMATION: Three Copies Artificial E-Box Insert

<400> SEQUENCE: 9

```
ggtaccgctg cgctgtcggg gccaggccgg gctcccagtg gattcgcggg cacagacgcc    60
caggaccgcg cttcccacgt ggcggaggga ctggggaccc gggcacccgt cctgcccctt   120
caccttccag ctccgcctcc tccgcgcgga ccccgccccg tcccgacccc tcccgggtcc   180
ccggcccagc cccctccggg ccctcccagc ccctccccctt cctttccgcg gccccgccct   240
ctcctcgcgg cgcgagtttc aggcagcgct gcgtcctgct gcgcacgtgg gaagccctgg   300
ccgatgggct cgacgcacgt gggcgcacgt gggcgcacgt gggagcttgg cattccggta   360
ctgttggtaa agccaccatg g                                            381
```

<210> SEQ ID NO 10
<211> LENGTH: 10
<212> TYPE: DNA
<213> ORGANISM: Artificial
<220> FEATURE:
<223> OTHER INFORMATION: Gel shift probe

<400> SEQUENCE: 10

```
cgcacgtggg                                                    10
```

```
<210> SEQ ID NO 11
<211> LENGTH: 20
<212> TYPE: DNA
<213> ORGANISM: Artificial
<220> FEATURE:
<223> OTHER INFORMATION: Gel Shift Probe 2

<400> SEQUENCE: 11
gctgcgcacg tgggaagccc                                                 20

<210> SEQ ID NO 12
<211> LENGTH: 20
<212> TYPE: DNA
<213> ORGANISM: Artificial
<220> FEATURE:
<223> OTHER INFORMATION: Gel Shift Probe 3

<400> SEQUENCE: 12
gctgcgcacc cgggaagccc                                                 20

<210> SEQ ID NO 13
<211> LENGTH: 20
<212> TYPE: DNA
<213> ORGANISM: Artificial
<220> FEATURE:
<223> OTHER INFORMATION: Gel Shift Probe 4

<400> SEQUENCE: 13
gcggaccccg ccccgtcccg                                                 20

<210> SEQ ID NO 14
<211> LENGTH: 18
<212> TYPE: DNA
<213> ORGANISM: Artificial
<220> FEATURE:
<223> OTHER INFORMATION: Sequencing Primer

<400> SEQUENCE: 14
agcggagaga ggtcgaat                                                   18

<210> SEQ ID NO 15
<211> LENGTH: 18
<212> TYPE: DNA
<213> ORGANISM: Artificial
<220> FEATURE:
<223> OTHER INFORMATION: Sequencing Primer

<400> SEQUENCE: 15
ctttgcccta gtggcaga                                                   18

<210> SEQ ID NO 16
<211> LENGTH: 19
<212> TYPE: DNA
<213> ORGANISM: Artificial
<220> FEATURE:
<223> OTHER INFORMATION: Sequencing Primer

<400> SEQUENCE: 16
gtgaattgtc tctgccact                                                  19

<210> SEQ ID NO 17
<211> LENGTH: 19
<212> TYPE: DNA
<213> ORGANISM: Artificial
<220> FEATURE:
<223> OTHER INFORMATION: Sequencing Primer
```

-continued

```
<400> SEQUENCE: 17
gattcctggg aagtcctca                                                      19

<210> SEQ ID NO 18
<211> LENGTH: 17
<212> TYPE: DNA
<213> ORGANISM: Artificial
<220> FEATURE:
<223> OTHER INFORMATION: Sequencing Primer

<400> SEQUENCE: 18
acctcgcggt agtggct                                                        17
```

COMPOSITIONS AND METHODS FOR ENHANCING DIFFERENTIAL EXPRESSION

FIELD

This application relates to the field of transcriptional regulatory sequences, specifically to artificial promoters derived from the telomerase reverse transcriptase (TERT) gene promoter, and to the use of such artificial promoters to enhance the differential expression of heterologous nucleic acid sequences and to treat disease, such as cancer.

BACKGROUND

Telomeres are specialized structures at chromosome ends, which consist of tandemly repeated DNA sequences and associated proteins (König and Rhodes, *Trends Biochem. Sci.*, 22: 43-47, 1997). In normal human somatic cells, telomeric DNA progressively shortens with each cell division. Critically short telomeres are thought to cause irreversible cell growth arrest and cellular senescence (Autexier and Greider, *Trends Biochem. Sci.*, 21: 387-391, 1996). In contrast, most cancer cells have mechanisms that compensate for telomere shortening, which allow them to stably maintain their telomeres and grow indefinitely (Chiu and Harley, *Proc. Soc. Exp. Biol. Med.*, 214: 99-106, 1997; Autexier and Greider, *Trends Biochem. Sci.*, 21: 387-391, 1996; Bodnar et al., *Science*, 279: 349-352, 1998).

Telomerase is a specialized, multi-subunit DNA polymerase responsible for the replication of telomeres. Thus, telomerase compensates for telomere shortening in cells where telomerase is active. Telomerase is highly active in many immortalized cell lines and human cancers, and is thought to be a factor in their continuing ability to replicate. In contrast, telomerase activity is low or absent in most normal somatic cells, which is thought to be a factor in their limited ability to replicate.

Several components of the human telomerase complex have been identified. Of these, the RNA component, which acts as an intrinsic template for telomeric repeat synthesis, and the telomerase catalytic subunit, known as human telomerase reverse transcriptase (hTERT), are necessary and sufficient for telomerase activity in vitro (Masutomi et al., *J. Biol. Chem.*, 275: 22568-22573, 2000).

hTERT expression at the mRNA level is correlated with human telomerase activity. Accordingly, the hTERT gene is highly expressed in many immortalized cell lines and human cancers and has limited expression in most normal somatic cells. The native regulatory regions that underlie the differential expression of the hTERT gene in cancer and normal cells have been isolated and characterized (e.g., Leem et al., *Oncogene*, 21(5): 769-777, 2002; Tzukerman et al., *Mol. Biol. Cell*, 11: 4381-4391, 2000; Wick et al., *Gene*, 232(1): 97-106, 1999; Horikawa et al., *Can. Res.*, 59: 826-830, 1999; Cong et al., *Hum. Mol. Genet.*, 8(1): 137-42, 1999). Deletion analyses of the hTERT promoter revealed that no more than several hundred base pairs located immediately upstream of the translation initiation codon were required for differential activity of the promoter in cancer and normal cells (e.g., Horikawa et al., *Can. Res.*, 59: 826-830, 1999). Thus, relatively small fragments of the hTERT promoter may be used to drive cancer-specific expression of operably linked nucleic acid sequences.

The cancer-specific activity of the hTERT promoter makes it a candidate for anti-cancer strategies. Studies using all or part of the native hTERT promoter to drive heterologous cytotoxic gene expression have shown selective killing of cancer cells in experimental models (e.g., Majumdar et al., *Gene Therapy*, 8: 568-578, 2001). However, an important characteristic of any promoter-driven therapeutic strategy must be its ability to target cancer cells while leaving normal cells relatively unaffected. The native hTERT promoter is not entirely silent in normal cells. Thus, heterologous nucleic acids to which the native promoter is operably linked will be expressed in some normal cells.

Even low-level expression of a cytotoxin in normal cells may cause undesired side effects. Thus, it would be advantageous to have available artificial TERT promoters that have minimal activity in normal cells but that maintain high-level expression in other cell types, such as cancer cells; thereby enhancing the differential expression of a TERT promoter in normal and cancer cells, for example.

SUMMARY

An unexpected E-box-mediated repression of transcriptional activity has been identified in the regulation of the hTERT gene promoter. The E-box-mediated transcriptional repression is observed in normal cells and not in many cancer cells. By linking one or more E-box elements in cis with TERT regulatory sequences, it is now possible to preferentially suppress the expression of heterologous nucleic acid sequences operably linked to TERT transcriptional regulatory sequences in normal cells without substantially decreasing the expression of such nucleic acid sequences in cells that do not exhibit the E-box-mediated transcriptional repression (hereinafter, "Repression-negative (R⁻) cells"), such as cancer cells. Hence, differential expression controlled by TERT transcriptional regulatory sequences can be enhanced in R⁻ cells versus normal cells.

This disclosure provides artificial TERT promoters that enhance differential expression in R⁻ cells as compared to normal cells. In some embodiments, one or more synthetic E-box elements are linked in cis with an hTERT promoter to produce an artificial TERT promoter. Also provided herein are methods of using artificial TERT promoters to enhance differential expression of an operably linked heterologous nucleic acid sequence; for instance, to direct the expression of cytotoxins in R⁻ cells while minimizing the expression of such cytotoxins in normal cells. Kits containing artificial TERT promoters suitable for enhancing the differential expression of heterologous nucleic acid sequences are also provided.

The foregoing and other features and advantages will become more apparent from the following detailed description of several embodiments, which proceeds with reference to the accompanying figures.

BRIEF DESCRIPTION OF THE FIGURES

FIG. 1. Nucleotide sequence of the 5'-flanking region, exon 1 and intron 1 of the hTERT gene. The 5'-flanking region and exon 1 are shown in uppercase, and the intron 1 is shown in lowercase. The major transcription initiation site (+1) and the translation initiation codon (ATG) are doubly underlined. A 1/2 EcoRV site (ATC) at the 5' end, two StuI sites (AGGCCT), two PvuII sites (CAGCTG), and an Eco47III site (AGCGCT) are thinly underlined. The GW2 primer, which was used for the PCR-based genomic walking, is shown by dashed underline. The 59-bp region responsible for the full promoter activity is highlighted in bold. Potential transcription factor binding sites from the 5'-end of this 59-bp region to the translation initiation codon are shown by thick underlines. The region identical to the HBV integration site in the huH-4 cell line (GenBank Accession No. X51995) is shown in bold and italic. The HBV genome is inserted adjacent to the position −307, although the downstream end of the insertion is not precisely determined.

The nucleic acid sequence shown in FIG. 1 corresponds to residues 2251 to 4293 of SEQ ID NO: 1. Thus, residue 2251 of SEQ ID NO: 1 is equivalent to position −1665 in FIG. 1, residue 4293 of SEQ ID NO: 1 is equivalent to position +378 in FIG. 1, and so forth for each nucleotide residue/position; provided that there is no position "0" in FIG. 1. Instead, position −1 (corresponding to residue 3915 in SEQ ID NO: 1) is immediately upstream (ie., 5') of position +1 (corresponding to residue 3916 in SEQ ID NO: 1) in FIG. 1.

Figure 2:
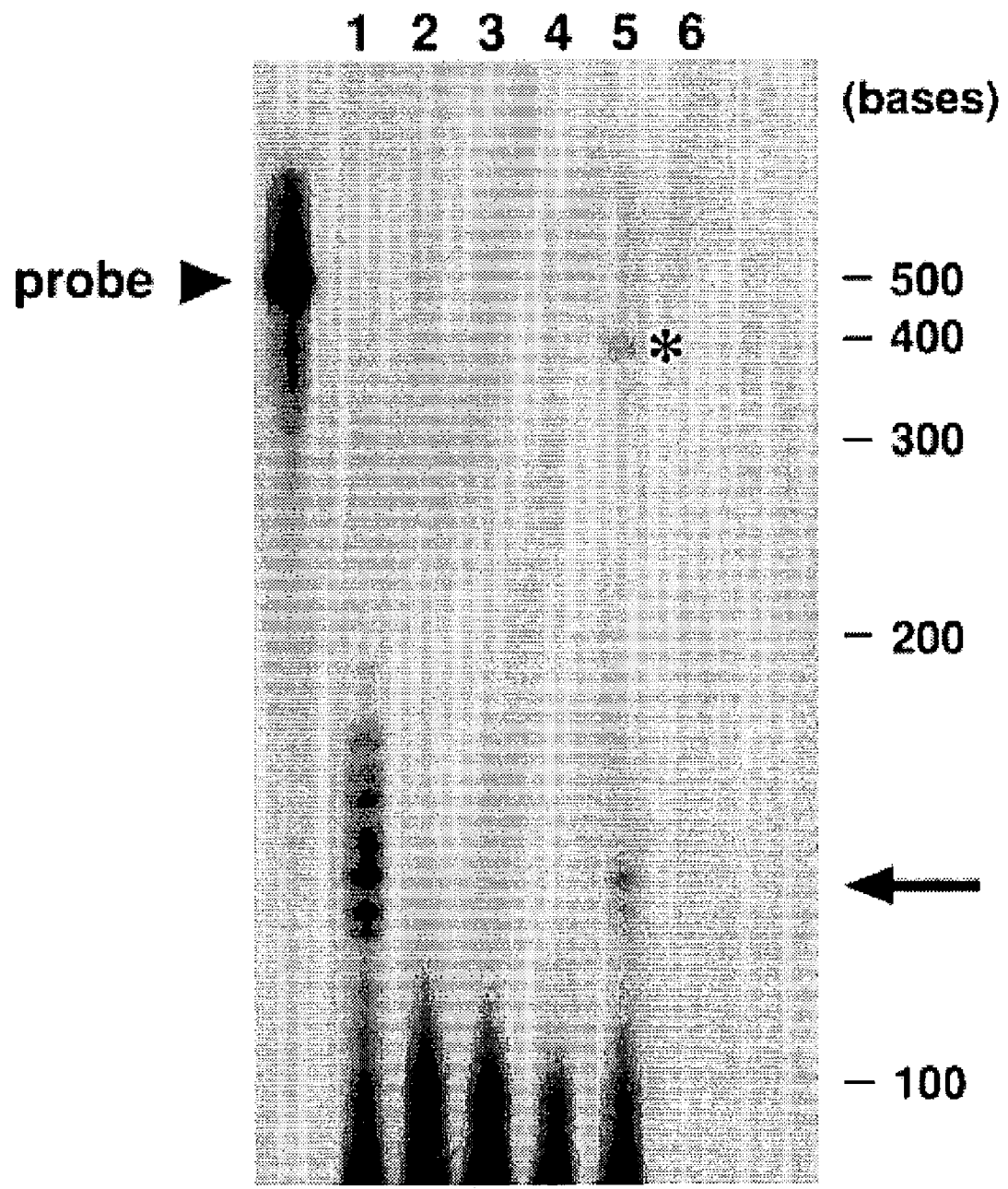

FIG. 2. A digital image of a ribonuclease protection assay used to demonstrate the transcription initiation sites of the hTERT gene. A 460-base RNA probe (SEQ ID NO: 6) complementary to the 390-bp sequence of the hTERT gene (from −255 to +135 in FIG. 1, corresponding to residues 3661 to 4050 of SEQ ID NO: 1) was hybridized to the following RNA samples: lane 1, CMV-Mj-HEL-1; lane 2, SUSM-1; lane 3, RCC23; lane 4, RCC23+3; lane 5, huH-4; lane 6, yeast RNA. The undigested probe is shown on the left. Size markers were transcribed in vitro from the Century marker template (Ambion). A 135-base major protected fragment and a 390-base fragment specific to huH-4 are indicated by an arrow and an asterisk, respectively. Signals near the bottom of the figure were common to both the hTERT mRNA-positive and -negative cell lines and thus appear to be non-specific.

Figure 3:
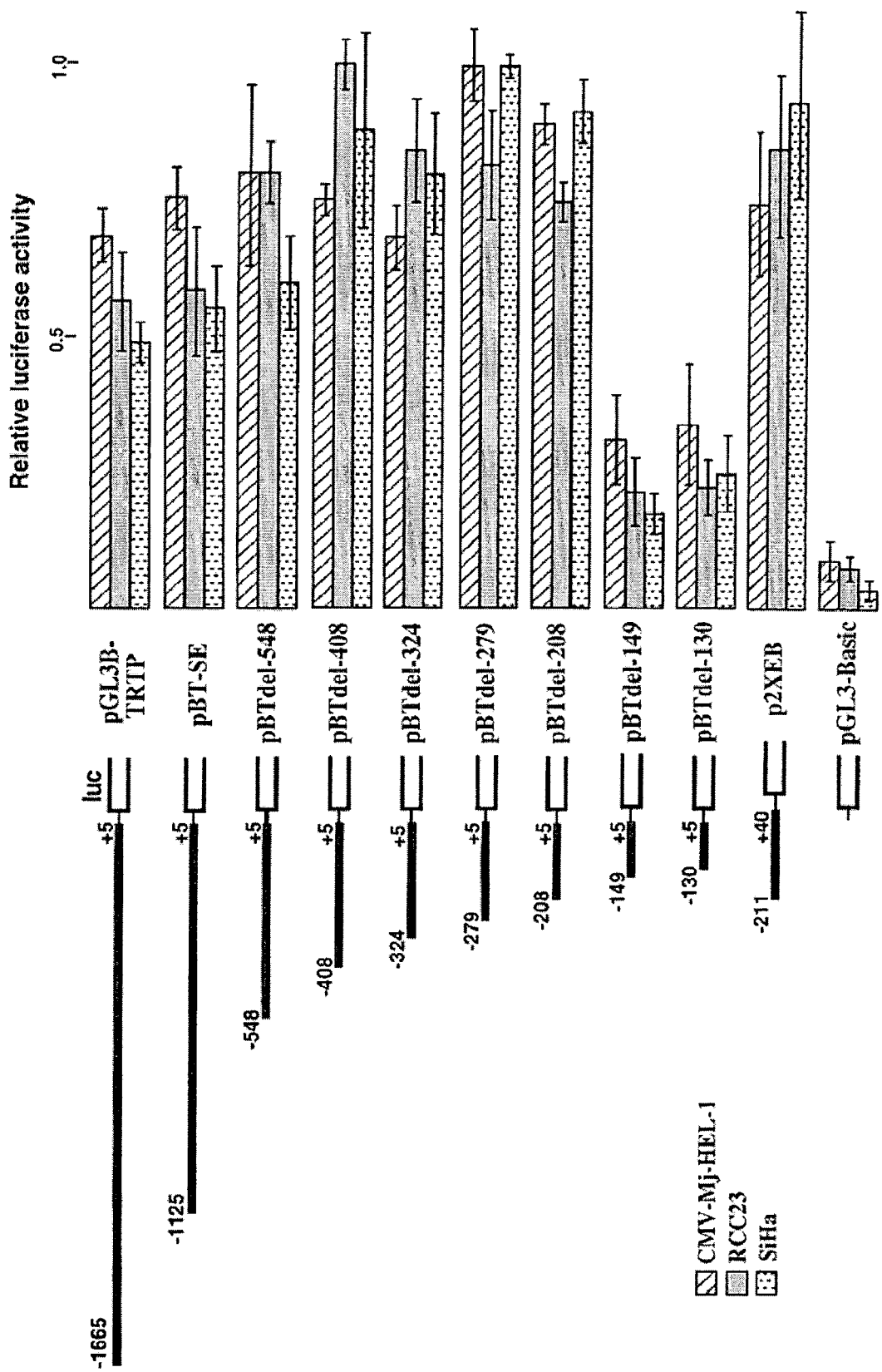

FIG. 3. A graph showing the results of luciferase assays used to identify the regions required for the hTERT gene promoter activity together with schematic representations of the promoter constructs tested. The fragments cloned upstream of the firefly luciferase reporter gene are shown by nucleotide positions which correspond to those in FIG. 1. For each transfection, the firefly luciferase activity was normalized with the *Renilla reniformis* luciferase activity by the co-transfected pRL-SV40. The relative activity of each construct is expressed as a ratio to the activity of the pBTdel-279 (CMV-Mj-HEL-1 and SiHa) or the pBTdel-408 (RCC23). The mean and standard deviation from at least three independent experiments are shown for each construct.

Figure 4:
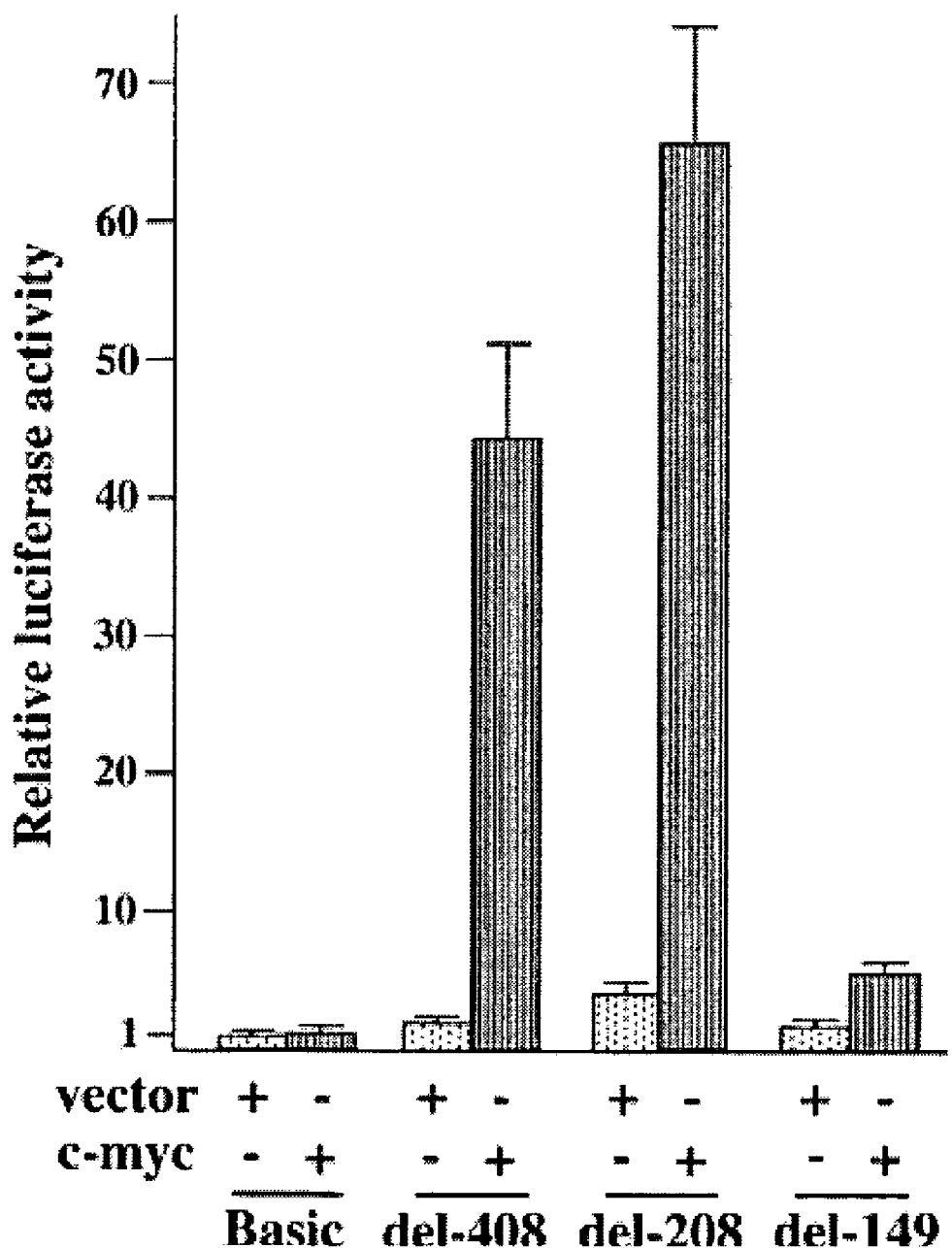

FIG. 4. A graph showing the induction of the hTERT gene promoter activity by c-Myc. A human c-Myc cDNA expression plasmid or a vector alone was co-transfected with the firefly luciferase construct (pGL3-Basic, pBTdel-408, pBTdel-208 or pBTdel-149) and the pRL-SV40 into the SUSM-1 cells. As described for FIG. 3, the firefly luciferase activity was normalized with the *Renilla reniformis* luciferase activity. Promoter activity of each combination of plasmids was expressed as fold induction relative to that of combination of the vector alone and the pGL3-Basic. Mean and standard deviation from three independent experiments are shown.

Figure 5:
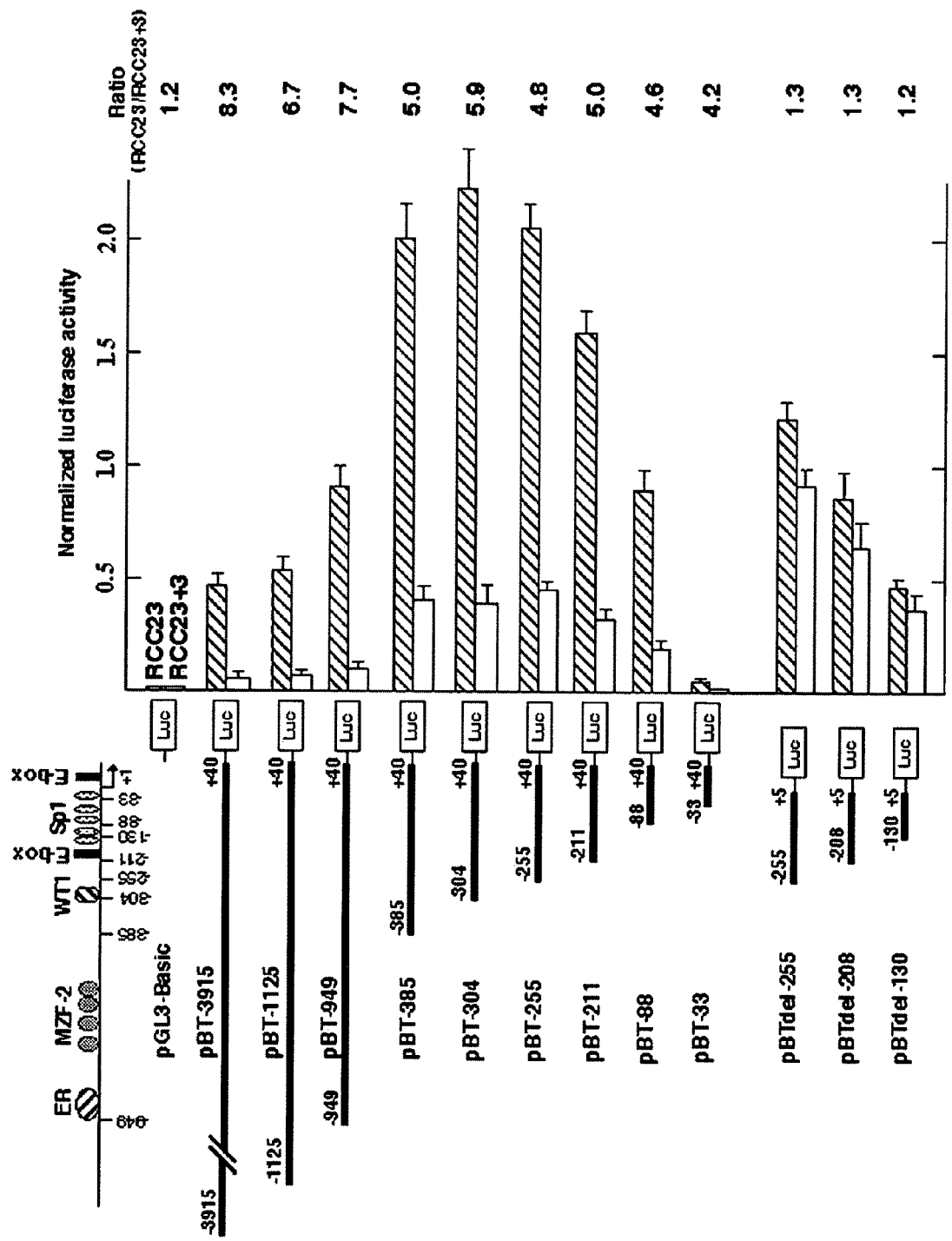

FIG. 5. A graph showing the results of luciferase assays of hTERT promoter activity in RCC23 and RCC23+3 together with schematic representations of the promoter constructs tested. A series of hTERT promoter fragments (nucleotide positions are as shown in FIG. 1) were cloned upstream of the firefly luciferase reporter gene in the pGL3-Basic vector. A schematic representation of transcription factor binding sites in the native hTERT promoter is shown above the promoter constructs. The firefly luciferase activity was normalized with the *Renilla reniformis* luciferase activity by the co-transfected pRL-SV40. The mean and standard deviation from at least three independent experiments are shown. For each construct, the activity in RCC23 was divided by that in RCC23+3 to determine the ratio of RCC23/RCC23+3, as an indicator of chromosome 3-mediated fold repression, which is shown to the right of the graph.

Figure 6:
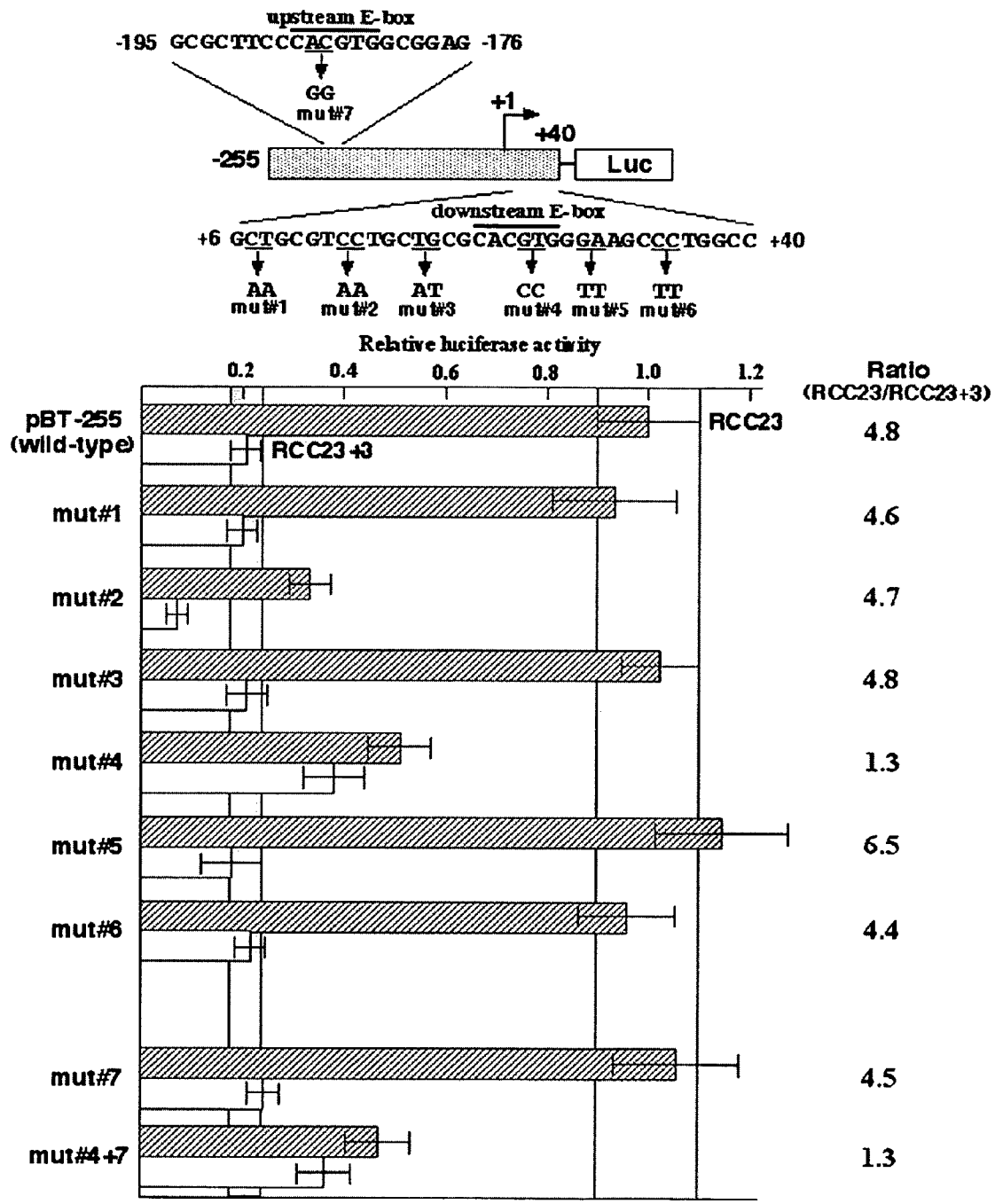

FIG. 6. A graph showing the results of luciferase assays, which identify a DNA element responsible for the differential hTERT transcription in RCC23 and RCC23+3. As shown by the schematic representation of the hTERT promoter located above the graph, six mutations within the region downstream of the transcription initiation site (mut# 1 to #6) and a mutation at the upstream E-box (mut#7) were made by site-directed mutagenesis of the construct pBT-255. The promoter activity of each fragment was measured by the luciferase assay, normalized as in FIG. 5, and expressed as a relative value to the activity of the pBT-255 (wild-type) in RCC23. The mean±SD ranges of the pBT-255 in RCC23 and RCC23+3 are highlighted for statistical comparison between this wild-type fragment and the mutant fragments. The ratio of RCC23/RCC23+3 (see FIG. 5 legend) is shown for each fragment on the right of the graph.

Figure 7:
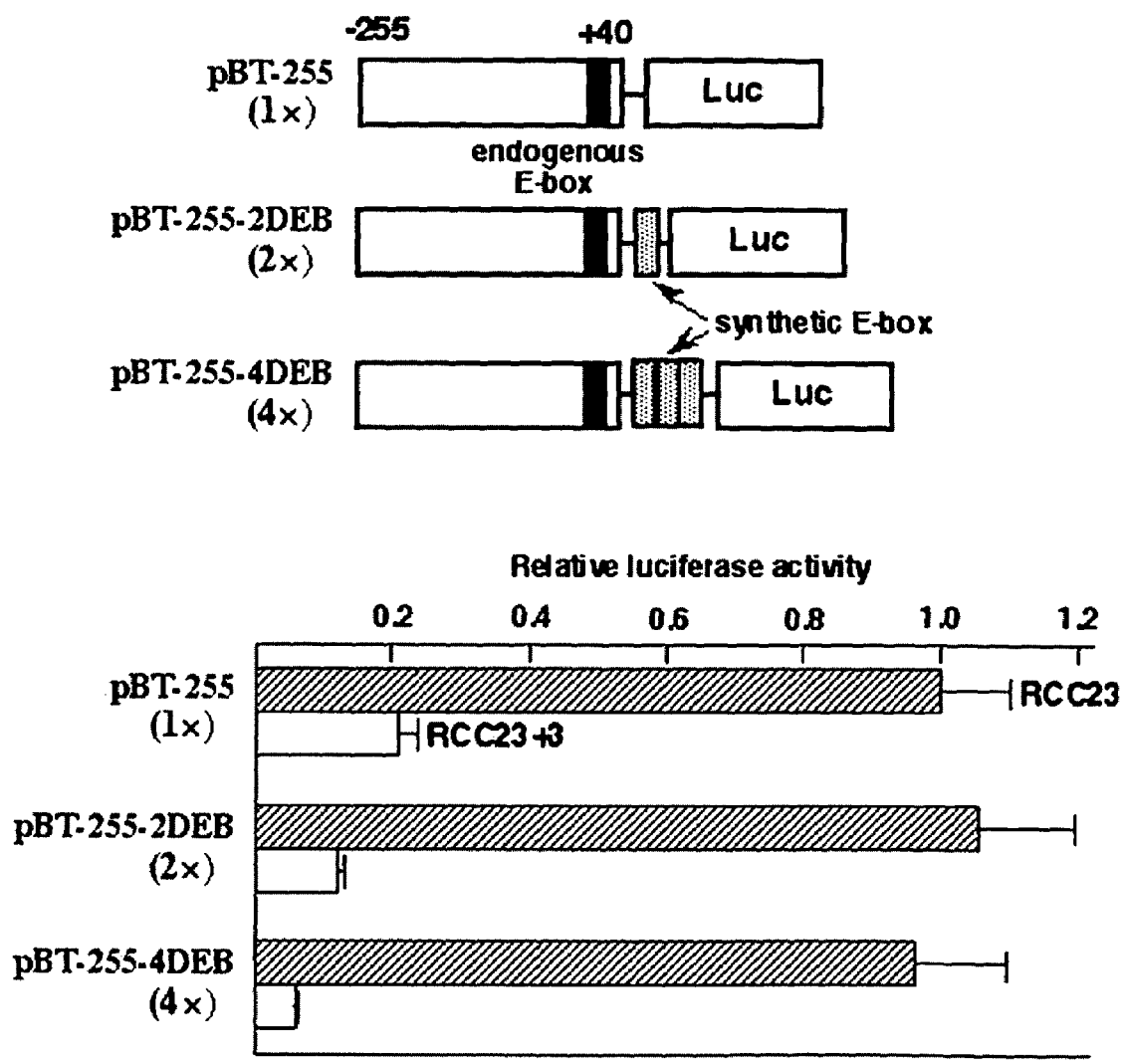

FIG. 7. A graph showing the repressive effect of E-box elements in RCC23+3. As shown by schematic representation, one or three copies of synthetic E-box sequence were inserted downstream of the hTERT promoter in the construct pBT-255 to make the construct pBT-255-2DEB or pBT-255-4DEB, respectively (total number of downstream E-box elements is shown in parenthesis). As described in FIG. 6, the promoter activity of each construct in RCC23 or RCC23+3 is expressed as a relative luciferase activity to the pBT-255 in RCC23.

Figure 8:
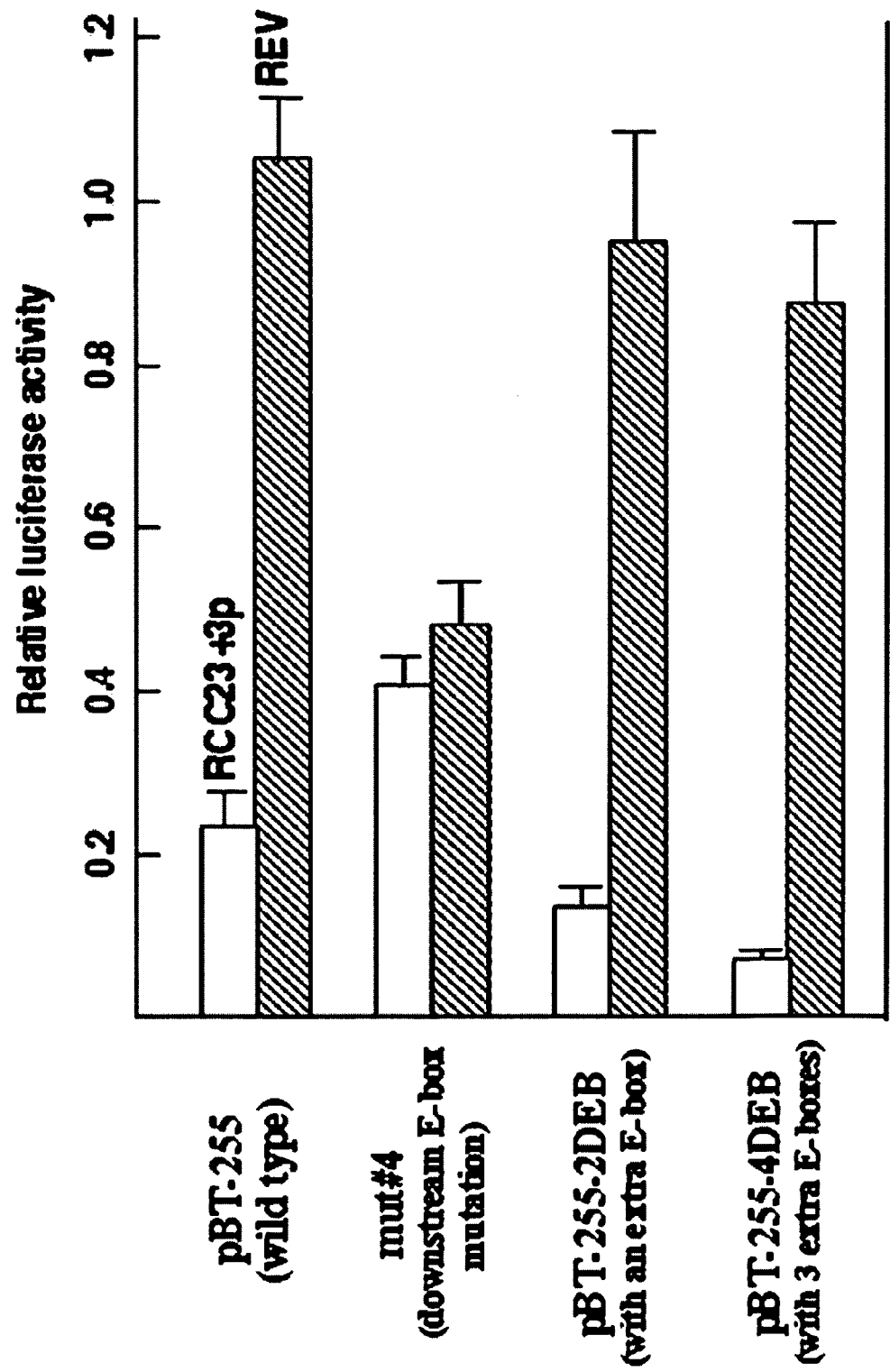

FIG. 8. A graph showing that downstream E-box-mediated repression is observed in RCC23+3p but not in a revertant clone, REV. RCC23+3p and REV cells (as described in Table 3) were used in the luciferase assay with the wild-type hTERT promoter fragment (pBT-255), the downstream E-box mutant (mut#4; see FIG. 6) and the synthetic E-box-containing fragments (pBT-255-2DEB and pBT-255-4DEB; see FIG. 7). The promoter activity of each construct in RCC23+3p or REV is expressed as a relative value to the activity of the pBT-255 in RCC23 (defined as 1.0 in FIGS. 6 and 7).

Figure 9:
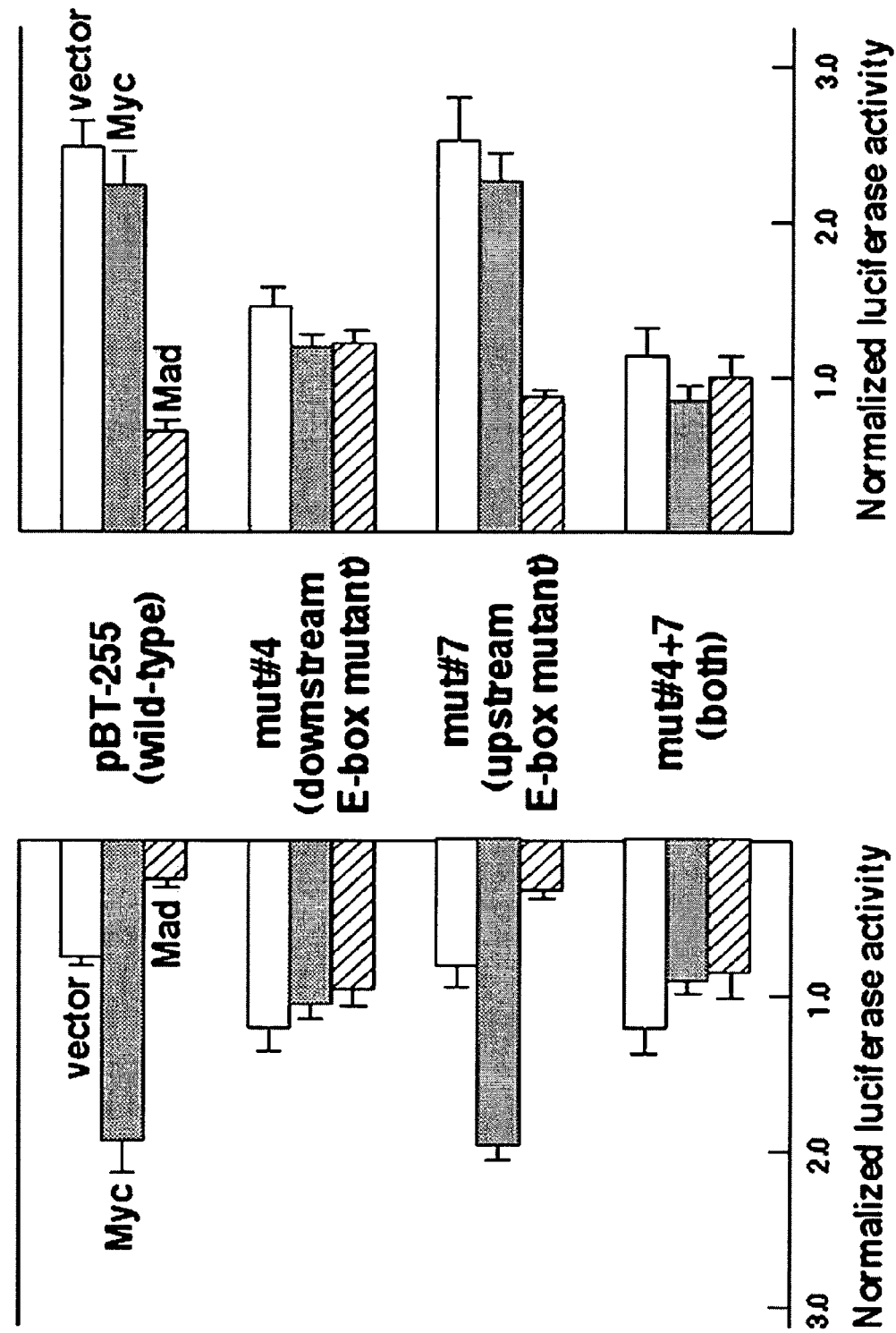

FIG. 9. A graph showing the effects of c-Myc and Mad1 overexpression on hTERT promoter activity. c-Myc or Mad1 expression plasmid or vector control was co-transfected with the pBT-255 and its E-box mutants (see FIG. 6). Overexpression of c-Myc or Mad1 protein was observed at similar levels in RCC23 and RCC23+3 (by western blot analysis, not shown). Normalized luciferase activity is shown for each combination of plasmids.

Figure 10:
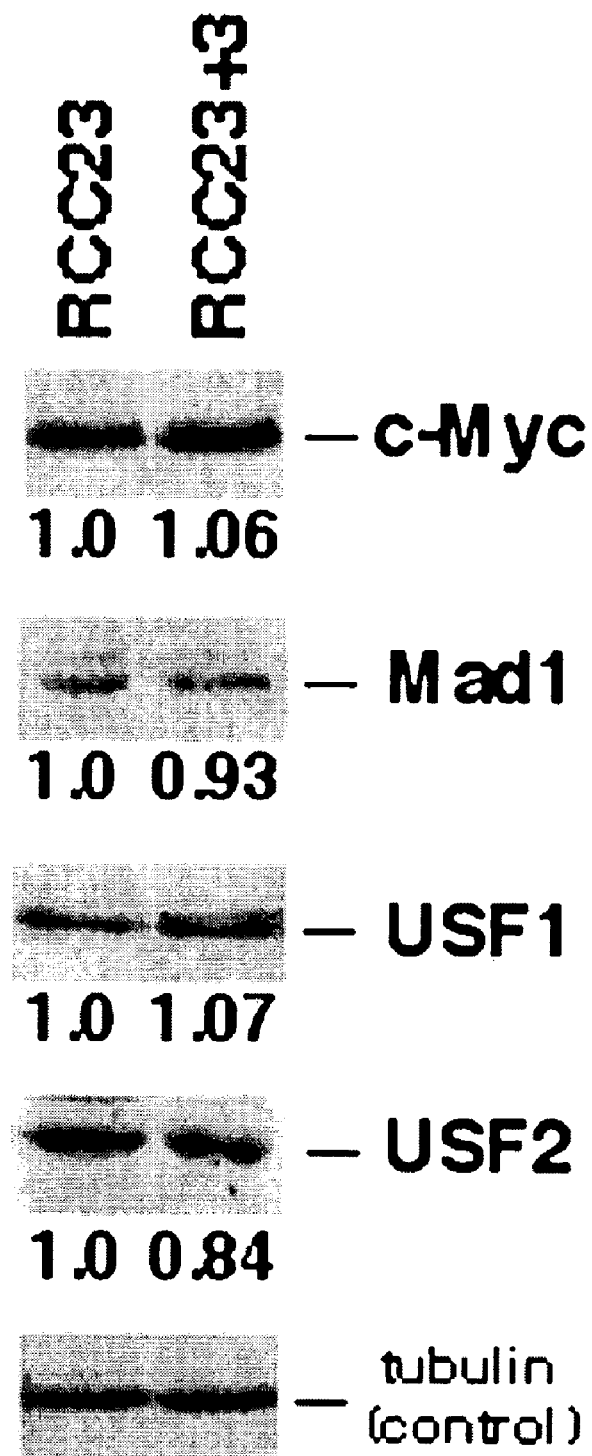

FIG. 10. A digital image of a western blot analysis of E-box binding proteins. Expression levels of representative E-box binding proteins (c-Myc, Mad 1, USF1 and USF2) and α-tubulin (a control for quantitation) were measured by densitometric analysis. The value of E-box binding proteins was normalized with that of α-tubulin. The expression level in RCC23+3 is shown relatively to that in RCC23.

Figure 11:
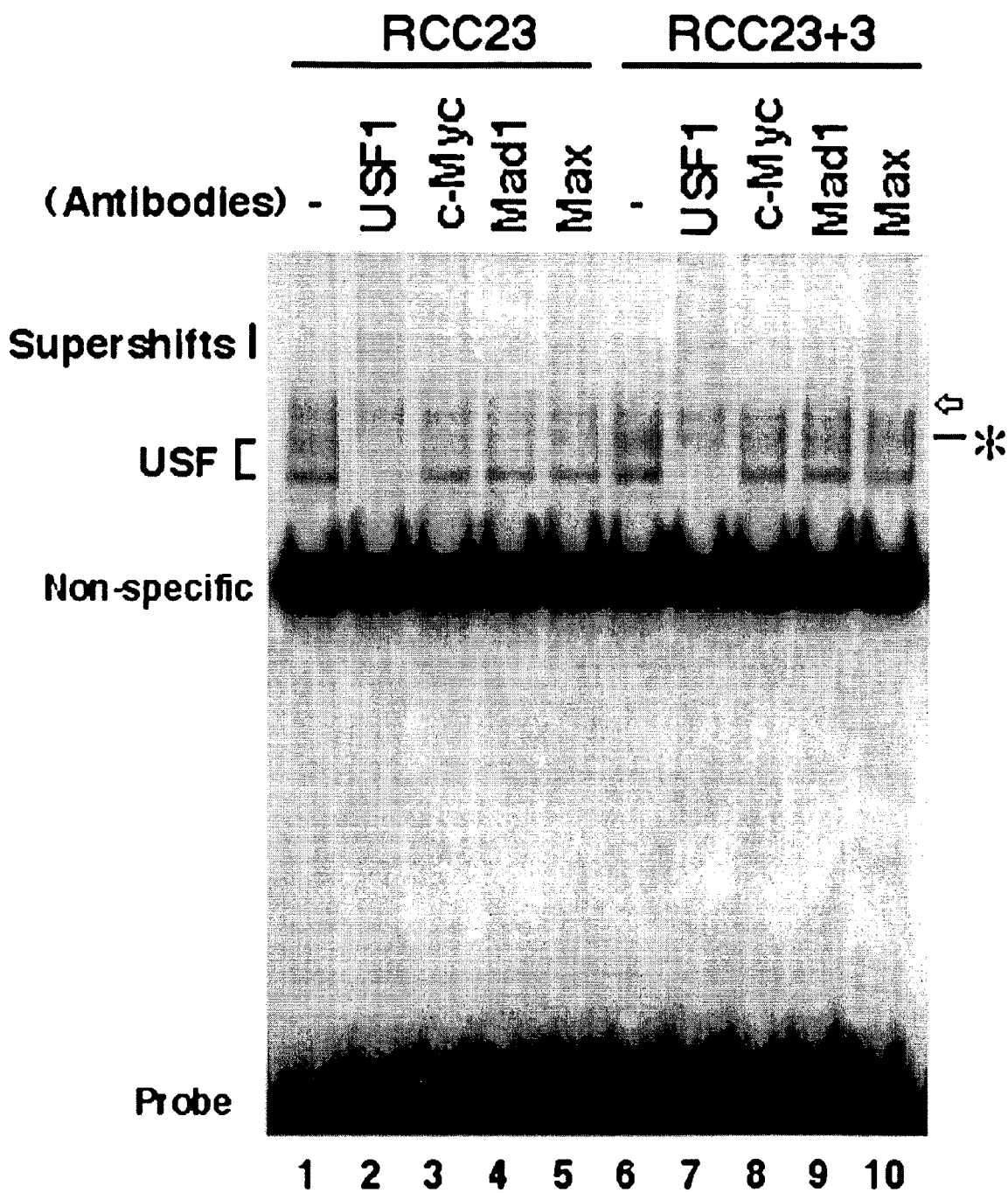

FIG. 11. A digital image of a gel mobility shift assay of E-box binding proteins in RCC23 and RCC23+3 cells. Result using the 10-bp probe containing a canonical E-box (from +20 to +29 in FIG. 1; SEQ ID NO: 10) is shown. For lanes 2 to 5 and 7 to 10, whole cell extracts were pre-incubated with the antibodies specific to the E-box binding proteins indicated. Position of the USF complexes is shown on the left. The asterisk indicates an RCC23+3-specific complex that was not supershifted or abrogated by any antibodies tested. The open arrow indicates a complex that is supershifted by the Max antibody. The supershifted bands containing the USF1 or Max antibody are indicated. These complexes were also detected by the 20-bp probe containing a canonical E-box (from +16 to +35 in FIG. 1; SEQ ID NO: 11), but not by the 20-bp probe with the E-box mutated (data not shown). The strong band common to all samples was also observed with the E-box-mutated probe and unrelated sequences (e.g., the Sp1 probe) and represents a non-specific binding. At the bottom of the figure is the free probe.

Figure 12:
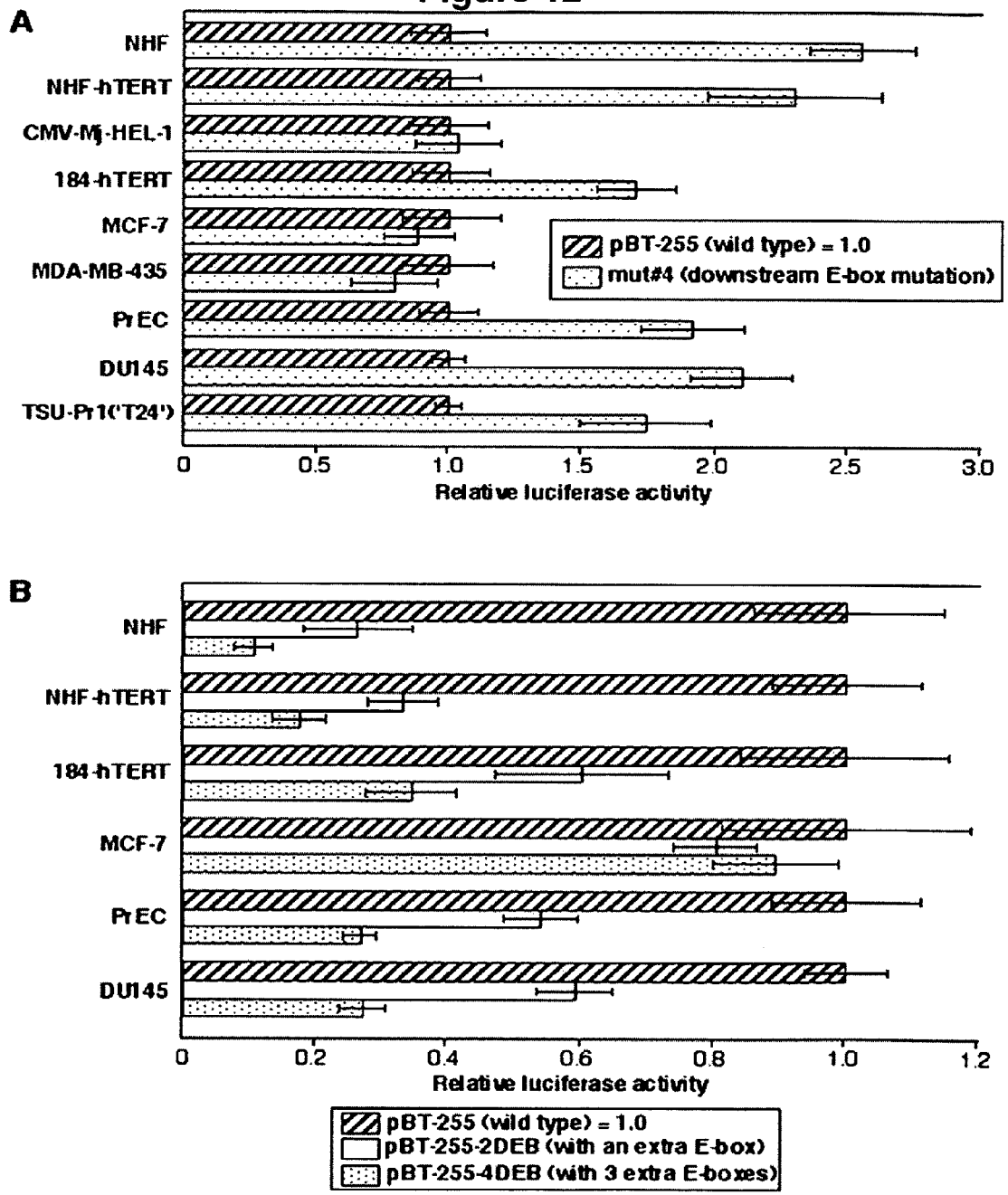

FIG. 12. Two graphs showing the results of experiments demonstrating the downstream E-box-mediated mechanism for the hTERT repression in normal human cells, retroviral hTERT-expressing cells, and endogenous hTERT-expressing immortalized and cancer cell lines. NHF, normal human fibroblasts; NHF-hTERT, retroviral hTERT-expressing NHF; CMV-Mj-HEL-1, immortalized fibroblast cell line; 184-hTERT, retroviral hTERT-expressing mammary epithelial cells 184; MCF-7, breast cancer cell line; MDA-MB-435, breast cancer cell line; PrEC, normal prostate epithelial cells; DU145, prostate cancer cell line; TSU-Pr1('T24'), bladder cancer cell line. (A) The promoter activity of the downstream E-box-mutated fragment (mut#4) was compared with that of the wild-type fragment (pBT-255), which was defined as 1.0 in each cell line. (B) The promoter activity of the synthetic E-box-containing fragments (pBT-255-2DEB and pBT-255-4DEB) was compared with that of the wild-type pBT-255 (defined as 1.0 in each cell line, as in (A)). For both (A) and (B), note that absolute values of hTERT promoter activity in normal cells (NHF and PrEC) and the retroviral hTERT-expressing cells (NHF-hTERT and 184-hTERT) are much lower (one twentieth to one hundredth) than in the endogenous hTERT-expressing cell lines.

Figure 13:
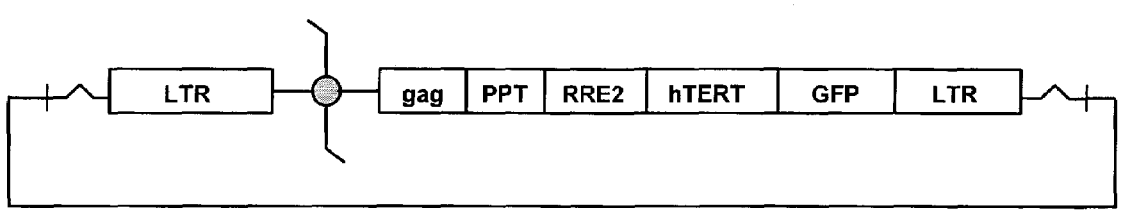

FIG. 13. A schematic representation of a lentiviral vector in which expression of a heterologous nucleic acid sequence is under the control of an artificial hTERT promoter.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows the nucleic acid sequence of a portion of the 5'flanking region, the first exon and the first intron of the human hTERT gene.

SEQ ID NO: 2 shows the amino acid sequence encoded by the first exon of the hTERT gene.

SEQ ID NO: 3 shows the nucleic acid sequence of Primer GW1.

SEQ ID NO: 4 shows the nucleic acid sequence of Primer GW2.

SEQ ID NO: 5 shows the nucleic acid sequence of the 430-bp probe used to screen the RPCI-11 human BAC library probe.

SEQ ID NO: 6 shows the nucleic acid sequence of the RNA probe used in RNAse protection assays.

SEQ ID NO: 7 shows the nucleic acid sequence of one E-box element embodiment.

SEQ ID NO: 8 shows the nucleic acid sequence of the pBT-255-2DEB hTERT promoter cassette, which includes one exogenous E-box element located downstream of a portion of the native hTERT promoter.

SEQ ID NO: 9 shows the nucleic acid sequence of the pBT-255-4DEB hTERT promoter cassette, which includes three exogenous E-box elements located downstream of a portion of the native hTERT promoter.

SEQ ID NO: 10 shows the nucleic acid sequence of a probe used for gel mobility shift assays.

SEQ ID NO: 11 shows the nucleic acid sequence of a probe used for gel mobility shift assays.

SEQ ID NO: 12 shows the nucleic acid sequence of a probe used for gel mobility shift assays.

SEQ ID NO: 13 shows the nucleic acid sequence of a probe used for gel mobility shift assays.

SEQ ID NO: 14 shows the nucleic acid sequence of a sequencing primer described herein.

SEQ ID NO: 15 shows the nucleic acid sequence of a sequencing primer described herein.

SEQ ID NO: 16 shows the nucleic acid sequence of a sequencing primer described herein.

SEQ ID NO: 17 shows the nucleic acid sequence of a sequencing primer described herein.

SEQ ID NO: 18 shows the nucleic acid sequence of a sequencing primer described herein.

DETAILED DESCRIPTION

I. Abbreviations

| | |
|---|---|
| ATCC | American Type Culture Collection |
| GFP | green fluorescent protein |
| HLH | helix-loop-helix |
| hTERT | human telomerase reverse transcriptase |
| NCBI | National Center for Biotechnology Information |
| NHF | normal human fibroblasts |
| ORF | open reading frame |
| PrEC | normal human prostate epithelial cells |
| TERT | telomerase reverse transcriptase |
| TU | transducing units |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

5' ends and 3' ends: Nucleic acid molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular nucleic acid molecule, discrete elements are referred to as being "upstream" or 5' of the "downstream" or 3' elements. This terminology reflects that transcription proceeds in a 5' to 3' direction along a DNA strand. The promoter and enhancer elements, which direct transcription of an operably linked nucleic acid sequence, are generally located 5' or upstream of the coding region. However, enhancer elements can exert their effect even when located 3' of the promoter element and the coding region. Transcription termination and polyadenylation signals are located 3' or downstream of the coding region.

5'-flanking region: Nucleic acid sequences, often regulatory in nature, that are located 5' of a transcription initiation site of a transcribed nucleic acid sequence. A 5'-flanking region may comprise several hundreds or thousands of upstream nucleotides.

Cancer: A biological condition in which a neoplasm has undergone characteristic anaplasia with loss of differentiation, increased rate of growth, invasion of surrounding tissue, and which is capable of metastasis.

The term(s) includes, but is not limited to, breast carcinomas (e.g. lobular and duct carcinomas), and other solid tumors, sarcomas, and carcinomas of the lung like small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma such as serous cystadenocarcinoma and mucinous cystadenocarcinoma, ovarian germ cell tumors, testicular carcinomas, and germ cell tumors, pancreatic adenocarcinoma, biliary adenocarcinoma, heptacellular carcinoma, bladder carcinoma including transitional cell carcinoma, adenocarcinoma, and squamous carcinoma, renal cell adenocarcinoma, endometrial carcinomas including adenocarcinomas and mixed Mullerian tumors (carcinosarcomas), carcinomas of the endocervix, ectocervix, and vagina such as adenocarcinoma and squamous carcinoma, tumors of the skin like squamous cell carcinoma, basal cell carcinoma, melanoma, and skin appendage tumors, esophageal carcinoma, carcinomas of the nasopharynx and oropharynx including squamous carcinoma and adenocarcinomas, salivary gland carcinomas, brain and central nervous system tumors including tumors of glial, neuronal, and meningeal origin, tumors of peripheral nerve, soft tissue sarcomas and sarcomas of bone and cartilage. Also included are non-solid hematopoietic tumors, such as leukemias.

Cis: Denotes that two or more nucleic acid sequences are located on the same nucleic acid molecule. For example, two or more nucleic acid sequences located on the same chromosome or on the same plasmid are oriented in cis with respect to each other. For example, a promoter and the gene it controls, which are located on a single chromosome, are oriented in cis with respect to each other. To be located or oriented in cis, two or more nucleic acid sequences need not be contiguous on the same nucleic acid molecule, nor be located near each other on the same nucleic acid molecule. A "cis-acting regulatory element" or "cis-acting element" is a regulatory control element that is located on the same nucleic acid molecule as the gene that it regulates. For example, an enhancer is a cis-acting element with respect to the gene whose transcription is increased by enhancer activation. More specifically, for example, an E-box element is a cis-acting element with respect to an operably linked heterologous nucleic acid sequence. Enhancer, silencers, and transcription initiation sites are each examples of cis-acting elements.

Cytotoxin, Cytotoxic Agent, or Toxin: Any agent that may be expressed in a cell under the control of an artificial TERT promoter, e.g., an RNA or polypeptide, that has a direct or indirect toxic, poisonous or therapeutic effect on a cell or cells. Such agents may also be called "therapeutic substances." Examples of polypeptide toxins include, without limitation, *Pseudomonas* exotoxin, *Pseudomonas* endotoxin, ricin A, saporin, abrin, ribonuclease, DNase I, *Staphylococcal* enterotoxin-A, pokeweed antiviral protein, gelonin, diphtheria toxin, tumor necrosis factor alpha, *Crotalus durissusterrificus* toxin, *Crotalus adamenteus* toxin, *Naja naja* toxin, and *Naja mocambique* toxin. The cellular toxin may be capable of inducing apoptosis, such as the ICE-family of cysteine proteases, the BcI-2 family of proteins, bax, bcIXs and caspases (e.g., Favrot, *Gene Ther.*, 5: 728-739, 1998; McGill, *Front. Biosci.*, 2: D353-D379, 1997; McDonnell, *Semin. Cancer Biol.*, 6: 53, 1995). Alternatively, the cytotoxic agent may not itself be toxic to a cell, but it may render the cell sensitive to an otherwise nontoxic drug. For example, herpes virus thymidine kinase when expressed in a cell will convert the otherwise non-toxic anti-herpetic agent ganciclovir to a toxic product that interferes with DNA replication in proliferating cells (e.g., Delaney, *J. Neurosci.*, 16: 6908-6918, 1996; Heyman, *Proc. Natl. Acad. Sci.*, 86: 2698, 1989). Cytokines, antisense nucleic acid molecules, ribozymes, and tumor suppressor proteins may also be cytotoxic when expressed in a cell, e.g., a cancer cell. Further examples of therapeutic substances could include, but not be limited to, tumor suppressor gene products, such as annexin 7, tumor suppressor gene peptides, and angiostatin proteins, which block tumor dependent capillary growth. The art describes numerous other suitable toxic, potentially toxic, or therapeutic agents that may be encompassed in the terms in this paragraph.

Differential Expression of a Nucleic Acid Sequence: A nucleic acid sequence is differentially expressed when its level of transcription is higher or lower in one cell (or tissue) type as compared to another cell (or tissue) type. For example, a gene, e.g., hTERT, which is highly expressed in cancer cells, but which has low levels of expression in normal somatic cells is differentially expressed. Thus, differential expression is a relative measurement of transcriptional activity of a nucleic acid sequence in two different cell types. Differential expression may mean, for example, that the expression of a particular nucleic acid sequence in one cell (or tissue) type is at least about 1%, at least about 2%, at least about 5%, at least about 10%, at least about 15%, at least about 20%, at least about 25%, at least about 30%, at least about 50%, at least about 75%, at least about 100%, at least about 150%, or at least about 200% of the expression of that nucleic acid sequence in another cell (or tissue) type. Alternatively, the comparison between cell types may be made in terms of fold difference; for example, the expression of a particular nucleic acid sequence in one cell (or tissue) type may be at least about 2-fold, at least about 3-fold, at least about 4-fold, at least about 5-fold, at least about 10-fold, at least about 20-fold, at least about 50-fold, at least about 100-fold, or at least about 200-fold times the expression of that nucleic acid sequence in another cell (or tissue) type.

Differential expression of a nucleic acid may also be thought of in terms of cell-type-specific (or tissue-type-specific) expression. For example, the expression of the hTERT gene described in the preceding paragraph may also be referred to as cancer-cell-specific expression.

Differential expression depends, at least in part, upon (i) the combination of individual cis-acting elements present in the regulatory control sequence of the transcribed nucleic acid sequence; and (ii) the combination of trans-acting factors that are expressed in each cell type and specifically interact with the regulatory control sequence of interest. The overall activity of a regulatory control sequence will depend upon which trans-acting factors are present in particular cell types, and reflects the combined action of the trans-acting factors associated with the individual cis-acting elements present in the regulatory control sequence. Thus, for example, if a regulatory control sequence contains a silencer that binds a trans-acting inhibitor, which is present in one cell type, e.g., normal cells, and not another cell type, e.g., cancer cells, the regulatory control sequence may be preferentially inhibited in the cells containing the trans-acting inhibitor, e.g., normal cells. Furthering the example, a nucleic acid sequence operably linked to the example regulatory control sequence may be differentially expressed in the two cell types, i.e., higher expression in cancer cells and lower expression in normal cells. One of skill in the art will appreciate the various combinations of cis-acting elements and trans-acting factors that may result in differential expression of a nucleic acid sequence.

Differential expression is "enhanced" by increasing the difference in the level of expression between two cell types. For example, if the expression of a nucleic acid sequence in a normal cell is 40% of the expression of that nucleic acid sequence in a cancer cell, the differential expression is enhanced if expression of the nucleic acid in the normal cell is decreased to 10% of the expression in the cancer cell. One of skill in the art will appreciate that differential expression of a nucleic acid sequence can be enhanced by decreasing expression in the less-active cell type without substantially changing expression in the highly active cell type, or by increasing expression in the highly active cell type without substantially changing expression in the less active cell type, or by concurrently decreasing expression in the less-active cell type and increasing expression in the highly active cell type.

E-box or E-box element: A regulatory control element that is recognized by numerous known transcription factors, e.g., transcription factors from the basic helix-loop-helix structural family (e.g., Corneliussen et al., *J. Virol.*, 65(11): 6084-93, 1991; Nielsen et al., *Mol. Cell. Biol.*, 12(8): 3449-59, 1992). The nucleic acid sequence of the E-box comprises CANNTG, where "N" is any nucleic acid residue. In one embodiment, an E-box element can have the sequence CACGTG. The sequence "CACGTG" is also known as a "canonical E-box." E-box elements have been reported to mediate activation of numerous promoters, including the hTERT promoter (e.g., Yago et al., *FEBS Lett.*, 520: 40-46, 2002; WO00/46355). In addition, E-box elements may be involved in inhibition of transcriptional activity of some promoters (e.g., Gery and Koeffler, *J. Mol. Biol.*, 328(5): 977-983, 2003; Li et al., *J. Biol. Chem.*, 278(19): 16899-16907, 2003). E-box elements may be synthesized, or may be isolated from existing nucleic acid sources that contain E-box sequences. Methods for synthesizing nucleic acids, such as an E-box element, and for isolating nucleic acid fragments, containing, e.g., an E-box element, from existing nucleic acid sources are commonplace and well within the knowledge of those skilled in the art. An "exogenous E-box element" is an isolated or synthetic E-box element that is added in cis to a first regulatory control sequence to produce a second regulatory control sequence. An exogenous E-box element is distinguished herein from one or more native, endogenous E-box elements that may naturally be contained within the first regulatory control sequence. By way of example, one or more synthetic E-box elements may be linked in cis to a promoter, such as an hTERT promoter. While the hTERT promoter (or a fragment or variant thereof) may naturally contain one or more native, endogenous E-box elements, the synthetic E-box elements in this example are considered to be exogenous with respect to the hTERT promoter (and any native, endogenous E-box elements contained therein).

Effective amount of a vector: A quantity of a vector sufficient to achieve a desired therapeutic effect in a subject being treated. For instance, this can be the amount necessary to decrease the size of a tumor in a subject. In general, this amount will be sufficient to monitor the decrease in the size of a tumor in some measurable way, such as by observation, palpitation, contrast radiography, MRI, or PET scan. An effective amount of a vector can be administered in a single dose, or in several doses, for example daily, during a course of treatment. However, the effective amount of the vector will be dependent on the vector applied, the subject being treated, the severity and type of the affliction, and the manner of administration of the vector. The general term "administering to the subject" is understood to include all animals (e.g. humans, apes, dogs, cats, horses, and cows) that have or may develop a tumor.

Enhancer: A cis-acting regulatory sequence that can increase levels of transcription of an operably linked nucleic acid sequence. An enhancer is activated by the specific binding of one or more trans-acting factor(s). Enhancer function does not depend on the distance of the enhancer from, or its orientation with respect to, the operably linked nucleic acid sequence. For instance, enhancers can affect the transcription of operably linked nucleic acid sequences that are located near to, or many tens of kilobases away from the enhancer. Similarly, enhancers can stimulate transcription when placed either upstream or downstream of a transcription initiation site and/or in either a forward or backward orientation. Enhancers may, but need not, contain multiple functional sequence elements that bind different trans-acting factors. A "tissue-specific" enhancer functions only in certain tissues. Such tissue-specific regulation by an enhancer may result, e.g., because the trans-acting factor(s) that specifically interact with the enhancer are expressed in some cell types, but not in others.

Gene: A nucleic acid molecule that comprises a nucleic acid sequence that is transcribed into an RNA transcript (e.g., an mRNA that is translated into a polypeptide) and the expression control sequences that surround the transcribed nucleic acid sequence. For instance, a gene may comprise a promoter, one or more enhancers, a nucleic acid sequence that encodes a polypeptide, downstream regulatory sequences and, possibly, other nucleic acid sequences involved in regulation of the expression of an RNA. As is well-known in the art, eukaryotic genes usually contain both exons and introns. The term "exon" refers to a nucleic acid sequence found in genomic DNA that is bioinformatically predicted and/or experimentally confirmed to contribute a contiguous sequence to a mature RNA transcript. The term "intron" refers to a nucleic acid sequence found in genomic DNA that is predicted and/or confirmed to not contribute to a mature RNA transcript, but rather to be "spliced out" during processing of the transcript.

Heterologous nucleic acid sequence (or heterologous gene): A transcribable nucleic acid sequence that is not normally (i.e. in the wild-type sequence) found adjacent to a second nucleic acid sequence. As described herein, a heterologous nucleic acid sequence (or heterologous gene) includes nucleic acid sequences that are capable of being transcribed into an RNA transcript (e.g., an mRNA that may be translated into a polypeptide or, e.g., an antisense RNA). Thus, unlike the term "gene," regulatory control sequences are not necessarily contemplated within the meaning of the terms "heterologous nucleic acid sequence" or "heterologous gene." In some embodiments, a heterologous nucleic acid sequence is a cDNA or a synthetic DNA. In other embodiments, a heterologous nucleic acid sequence is a genomic sequence that encodes an RNA transcript. In additional embodiments, a heterologous nucleic acid sequence is a reporter gene. In still other embodiments, a heterologous nucleic acid sequence is a nucleic acid sequence encoding a cytotoxin.

Inhibiting cellular growth: The phrase "inhibiting cellular growth" (and analogous phrases, such as inhibition of cell growth or inhibition of cellular proliferation) conveys a wide-range of inhibitory effects that an agent (e.g., a vector including an artificial TERT promoter directing the expression of a therapeutic substance) may have on the normal (i.e., control) rate of cell growth. The phrase "inhibiting cellular growth" (or like terminology) may be considered relative to the normal (i.e., uninhibited or control) rate of growth of a particular cell or population of cells of interest. Thus, inhibiting cellular growth includes situations wherein the normal growth rate of a cell or cell population has slowed (i.e., cell number increases over time, but not as rapidly as in a control population), equals zero (i.e., there is substantially no change in number of cells in the population over time, e.g., cell growth is approximately equal to cell death), or becomes negative (i.e., the number of cells decreases over time, e.g., cell death exceeds cell growth). A negative rate of cell growth can (but need not) result in the death of all cells in a population.

Isolated: When used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids, such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extra-chromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single stranded). Alternatively, it may contain both the sense and anti-sense strands (i.e., the oligonucleotide may be double stranded).

Nucleic acid molecule: A polymeric form of nucleotides and includes both sense and antisense strands of RNA, cDNA, genomic DNA, and synthetic forms and mixed polymers of the above. A nucleotide refers to a ribonucleotide, deoxy-nucleotide or a modified form of either type of nucleotide. A "nucleic acid molecule" as used herein is synonymous with "nucleic acid" and "polynucleotide." The term "nucleic acid molecule" usually refers to a molecule of at least 10 bases in length, unless otherwise specified. The term includes single- and double-stranded forms of DNA. In addition, a polynucleotide may include either or both naturally occurring and modified nucleotides linked together by naturally occurring and/or non-naturally occurring nucleotide linkages.

The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The term "nucleic acid molecule" also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Operably linked: A first nucleic acid sequence is operably linked with a second nucleic acid sequence when the first nucleic acid sequence is in a functional relationship with the second nucleic acid sequence. For instance, a promoter is operably linked to a coding sequence if the promoter affects the transcription or expression of the coding sequence. When recombinantly produced, operably linked nucleic acid sequences are generally contiguous and, where necessary to join two protein-coding regions, in the same reading frame. However, nucleic acids need not be contiguous to be operably linked.

Polylinker: A relatively short nucleic acid sequence (typically, less than 100 nucleotides in length) containing a cluster of numerous restriction endonuclease sites. The restriction sites in a polylinker may overlap, and they are generally not present in the larger nucleic acid sequence, e.g., a plasmid vector, that contains the polylinker. Polylinkers are typically engineered into cloning vectors to facilitate insertion of exogenous nucleic acid fragments, e.g., cDNAs, into the vector. Polylinkers are also known as "multiple cloning sites."

Preventing or treating a disease: Preventing a disease refers to inhibiting the partial or full development or progression of a disease, for example in a person who has symptoms of or is known to have a predisposition to a disease. An example of a person with a known predisposition is someone with a history of cancer in the family, or who has been exposed to factors that predispose the subject to a condition, such as cancer. Treating a disease refers to a therapeutic intervention that ameliorates at least one sign or symptom of a disease or pathological condition, or interferes with a pathophysiological process, after the disease or pathological condition has begun to develop.

Promoter: A nucleic acid sequence comprising a plurality of regulatory control elements (including, e.g., enhancers, silencers, initiators, and core promoter sequences), which collectively control the transcription of an operably linked nucleic acid sequence. The core promoter sequence, which is generally located near the transcription initiation site, is necessary for the binding of RNA polymerase. For example, a TATA box forms a portion of the core promoter sequence of promoters recognized by RNA polymerase II. Enhancer and silencer elements can be located adjacent to the core promoter sequences or can be located hundreds or thousands of base pairs away from the start site of transcription.

A "cell-specific promoter" directs the differential expression of a nucleic acid sequence (defined above). In one embodiment, a cell-specific promoter directs expression in cancer cells, but not in normal somatic cells.

A "TERT promoter" is any of an array of TERT genomic sequences capable of directing differential expression of a nucleic acid sequence. The term encompasses TERT promoters of any species from which TERT genomic regulatory sequences have been or may be isolated using technique described herein or well known in the art. TERT promoter sequences have been isolated, e.g., from human (as described herein, or, e.g., WO00/46355), mouse (e.g., Martin-Rivera et al., *Proc. Natl. Acad. Sci.*, 95(18): 10471-10476, 1998, or WO00/46355), hamster (e.g., Park et al., Int. J. Oncol., 19(4): 755-761, 2001) and other non-mammalian species (e.g., *Euplotes aediculatus, Saccharomyces cerevisiae, Schizosaccharomyces pombe*). "hTERT promoter" refers to a human TERT promoter. TERT promoters include without limitation cis-acting transcriptional control elements and regulatory sequences that are involved in regulating or modulating the timing and/or rate of transcription of an operably linked nucleic acid sequence. A TERT promoter may be thought of as a plurality of cis-acting transcriptional control elements, including, without limitation, enhancers, silencers, core promoter elements, transcription terminators, origins of replication, chromosomal integration sequences, 5' and 3' untranslated regions, exons and introns, which are involved in transcriptional regulation. These cis-acting elements typically interact with proteins or other biomolecules to carry out (e.g., turn on/off, regulate, modulate, etc.) transcription.

One of skill in the art will appreciate that the hTERT promoter sequences provided herein are exemplary only, and that they may be used as a basis to produce numerous versions of artificial TERT promoters that are capable of enhancing differential expression of an operably linked nucleic acid sequence. For purposes of this disclosure, the TERT promoter element of an artificial TERT promoter need only direct differential expression of an operably linked nucleic acid sequence in at least two cell types, e.g., cancer cells and normal, somatic cells. For example, the TERT promoter can direct cancer-cell-specific expression. Certain embodiments of hTERT promoter sequences that direct differential expression in at least two cell types are listed in Table 1 below.

TABLE 1

Certain Embodiments of hTERT Promoter Sequences

| Plasmid Construct | Residues of hTERT Promoter |
| --- | --- |
| pGL3B-TRTP | Residues −1665 to +5 in FIG. 1 (corresponding to residues 2251 to 3920 of SEQ ID NO: 1) |
| pBT-3915 | Residues −3915 to +40 in FIG. 1 (corresponding to residues 1 to 3955 of SEQ ID NO: 1) |
| pBT-1125 | Residues −1125 to +40 in FIG. 1 (corresponding to residues 2791 to 3955 of SEQ ID NO: 1) |
| pBT-949 | Residues −949 to +40 in FIG. 1 (corresponding to residues 2967 to 3955 of SEQ ID NO: 1) |
| pBT-385 | Residues −385 to +40 in FIG. 1 (corresponding to residues 3531 to 3955 of SEQ ID NO: 1) |
| pBT-304 | Residues −304 to +40 in FIG. 1 (corresponding to residues 3612 to 3955 of SEQ ID NO: 1) |
| pBT-255 (−255 to +40) | Residues −255 to +40 in FIG. 1 (corresponding to residues 3661 to 3955 of SEQ ID NO: 1) |
| pBT-255 mut#1 | Residues −255 to +40 in FIG. 1 (corresponding to residues 3661 to 3955 of SEQ ID NO: 1), wherein residues +7 and +8 (corresponding to residues 3922 and 3923 in SEQ ID NO: 1) have been mutated to "AA." |
| pBT-255 mut#2 | Residues −255 to +40 in FIG. 1 (corresponding to residues 3661 to 3955 of SEQ ID NO: 1), wherein residues +13 and +14 (corresponding to residues 3928 and 3929 in SEQ ID NO: 1) have been mutated to "AA." |

TABLE 1-continued

Certain Embodiments of hTERT Promoter Sequences

| Plasmid Construct | Residues of hTERT Promoter |
| --- | --- |
| pBT-255 mut#3 | Residues −255 to +40 in FIG. 1 (corresponding to residues 3661 to 3955 of SEQ ID NO: 1), wherein residues +18 and +19 (corresponding to residues 3933 and 3934 in SEQ ID NO: 1) have been mutated to "AT." |
| pBT-255 mut#5 | Residues −255 to +40 in FIG. 1 (corresponding to residues 3661 to 3955 of SEQ ID NO: 1), wherein residues +24 and +25 in FIG. 1 (corresponding to residues 3939 and 3940 in SEQ ID NO: 1) have been mutated to "TT." |
| pBT-255 mut#6 | Residues −255 to +40 in FIG. 1 (corresponding to residues 3661 to 3955 of SEQ ID NO: 1), wherein residues +34 and +35 in FIG. 1 (corresponding to residues 3949 and 3950 in SEQ ID NO: 1) have been mutated to "TT." |
| pBT-255 mut#7 | Residues −255 to +40 in FIG. 1 (corresponding to residues 3661 to 3955 of SEQ ID NO: I), wherein residues −185 and −186 in FIG. 1 (corresponding to residues 3731 and 3730 in SEQ ID NO: 1) have been mutated to "GG." |
| pBT-211 (−211 to +40) | Residues −211 to +40 in FIG. 1 (corresponding to residues 3705 to 3955 of SEQ ID NO: 1) |
| pBT-88 (−88 to +40) | Residues −88 to +40 in FIG. 1 (corresponding to residues 3828 to 3955 of SEQ ID NO: 1) |
| pBT-33 (−33 to +40) | Residues −33 to +40 in FIG. 1 (corresponding to residues 3883 to 3955 of SEQ ID NO: 1) |
| pBT-SE | Residues −1125 to +5 in FIG. 1 (corresponding to residues 2791 to 3920 of SEQ ID NO: 1) |
| pBTdel-548 | Residues −548 to +5 in FIG. 1 (corresponding to residues 3368 to 3920 of SEQ ID NO: 1) |
| pBTdel-408 | Residues −408 to +5 in FIG. 1 (corresponding to residues 3508 to 3920 of SEQ ID NO: 1) |
| pBTdel-324 | Residues −324 to +5 in FIG. 1 (corresponding to residues 3592 to 3920 of SEQ ID NO: 1) |
| pBTdel-279 | Residues −279 to +5 in FIG. 1 (corresponding to residues 3637 to 3920 of SEQ ID NO: 1) |
| pBTdel-149 | Residues −149 to +5 in FIG. 1 (corresponding to residues 3767 to 3920 of SEQ ID NO: 1) |

One of skill in the art will appreciate that differential expression may be obtained using longer or shorter TERT promoter sequences. In some embodiments, TERT promoter sequences comprising at least the downstream E-box are contemplated; for example, in one embodiment the TERT promoter sequence comprises at least residues −33 to +40 in FIG. 1 (corresponding to residues 3883 to 3955 of SEQ ID NO: 1).

One of skill in the art will further appreciate that promoter sequences that vary from those sequences provided herein by, for example, nucleotide additions, deletions or substitutions may also be used to obtain differential expression. Such variants will share a specified minimum level of structural (sequence) similarity to the disclosed TERT promoter sequences, which similarity may be defined in terms of either sequence identity to the disclosed TERT promoter sequences, or the ability to hybridize to the disclosed sequences at specified levels of hybridization stringency, as discussed below. For example, variant TERT promoters include promoters that hybridize to the TERT promoters disclosed herein under stringent conditions, under medium stringency conditions, or under low stringency conditions, as long as such variant TERT promoters are capable of directing differential expression of a nucleic acid sequence in at least two cell types, e.g., cancer cells and normal, somatic cells. Other variant TERT promoters include promoters that share at least about 50%, at least about 60%, at least about 70%, at least about 75%, at least about 80%, at least about 90%, at least about 95%, at least about 98%, or at least about 99% sequence identity with the originating TERT promoter sequence. Methods for determining sequence identity are discussed below. One of skill in the art will appreciate that these sequence identity ranges are provided for guidance only; it is entirely possible that strongly significant homologues could be obtained that fall outside of the ranges provided.

The determination that a promoter is capable of differential expression can be routinely performed as described in Examples 4 and 8-11. Briefly, the promoter to be tested is operably linked to a coding region that encodes a detectable protein such as luciferase, alkaline phosphatase or green fluorescent protein. This construct is then introduced into at least two different cell types, e.g., a cancer cell line and a normal cell line. Detection of the detectable protein in one cell line, e.g., a cancer cell line, but not in the other cell line, e.g., a normal cell line, or of an elevated level of the detectable protein in one cell line, e.g., a cancer cell line, compared to the other cell line, e.g., a normal cell line (preferably at least a three-fold difference) indicates that the promoter is a TERT promoter.

In alternative embodiments, the TERT promoter sequence comprises TERT sequences that include the downstream E-box element (residues 3937 to 3942 of SEQ ID NO: 1), for example, in one embodiment, the hTERT promoter comprises residues 3661 to 3955 of SEQ ID NO: 1 (e.g., pBT-255). Other embodiments include sequences starting within about the one to five nucleotides downstream (i.e., 3') of the downstream E-box element and ending at about 50, 100, 150, 200, 250, 500, 1000, 1500, 2000, 2500, 3000, 3500 or 3970 nucleotides upstream (i.e., 5') of the downstream E-box element. Such embodiments can optionally include other regulatory sequences, such as, core promoter elements, exon and/or intron sequences. Other embodiments include TERT promoter fragments and TERT promoters containing mutations as described in Example 10.

An "artificial TERT promoter" is a TERT promoter that has been linked in cis with at least 1, at least 2, at least 3, at least 4, at least 5, at least 7, at least 10, at least 12, at least 15, at least 20, or at least 25 exogenous regulatory control sequence, e.g., cis-acting element or, more specifically, exogenous E-box element. For example, an artificial TERT promoter may comprise a portion of the native hTERT promoter linked in cis with one or more exogenous E-box elements. An artificial TERT promoter may optionally contain TERT core promoter sequences, TERT intronic or TERT exon sequences. Preferentially, an artificial TERT promoter will direct differential expression of an operably linked heterologous nucleic acid sequence in at least two cell types, e.g., cancer cells and normal, somatic cells.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. Similarly, a recombinant protein is one encoded for by a recombinant nucleic acid molecule. A recombinant protein may be obtained by introducing a recombinant nucleic acid molecule into a host cell (e.g., a eukaryotic cell or cell line, such as a mammalian cell or yeast, or a prokaryotic cell, such as bacteria, e.g., *E. coli.*) and causing the host cell to produce the gene product. Methods of causing a host cell to express a recombinant protein are well known in the art (see, e.g., Sambrook et al., *Molecular Cloning—A Laboratory Manual,* 2nd edition, New York: Cold Spring Harbor Laboratory Press, 1989).

Regulatory control sequence (or transcriptional regulatory sequence): A nucleic acid sequence comprising a plurality of cis-acting elements, including, without limitation, enhancers, silencers, promoters, transcription terminators, origins of replication, chromosomal integration sequences, 5' and 3' untranslated regions, exons and introns, which in combination form a function unit that regulates the transcription of an operably linked second nucleic acid sequence. For example, a TERT promoter is a regulatory control sequence. In another example, a TERT promoter linked in cis with at least one, such as one or three, synthetic E-box element(s) is a regulatory control sequence.

Reporter gene: A nucleic acid sequence that encodes an easily assayed product (e.g. firefly luciferase, chloramphenicol acetyltransferase (CAT) and β-galactosidase). A reporter gene may be operably linked to a regulatory control sequence and transfected into cells. If the regulatory control sequence is transcriptionally active in a particular cell type, the reporter gene product will normally be expressed in such cells and its activity may be measured using techniques known in the art. The activity of a reporter gene produce can be used, for example, to assess the transcriptional activity of an operably linked regulatory control sequence.

Repression-negative ($R^-$) cells: A cell or cells, e.g., naturally occurring cancer cells or cancer cell lines, in which the expression of an operably linked nucleic acid sequence, e.g., a reporter gene, is not substantially decreased by linking one or more exogenous E-box element(s) in cis with a TERT promoter. Methods for identifying $R^-$ cells are described in detail in Example 15. Without being limited to one theory, it is thought that $R^-$ cells are deficient in a repressive E-box-mediated mechanism that actively functions in normal cells; for example, $R^-$ cells may be deficient in a trans-acting factor that specifically binds the downstream E-box and inhibits transcriptional activity in normal cells. In some embodiments, $R^-$ cells are cancer cells or immortalized cells or telomerase-positive cells. In other embodiments, $R^-$ cells are immortalized fibroblast cells, such as CMV-Mj-HEL-1, and breast cancer cells, such as MCF-7 and MDA-MB-435.

Sequence identity: The similarity between nucleic acid (or amino acid) sequences is expressed in terms of the percentage of conservation between the sequences, otherwise referred to as sequence identity. Sequence identity is measured, for instance, in terms of percentage identity (or similarity or homology); the higher the percentage, the more similar the two sequences are. Homologues or variants of a TERT promoter will possess a relatively high degree of sequence identity when aligned using standard methods.

Methods of alignment of sequences for comparison are well known in the art. Various programs and alignment algorithms are described in: Smith and Waterman, *Adv. Appl. Math.,* 2: 482, 1981; Needleman and Wunsch, *J. Mol. Biol.,* 48: 443, 1970; Pearson and Lipman, *Proc. Natl. Acad. Sci. U.S.A.,* 85: 2444, 1988; Higgins and Sharp, *Gene,* 73: 237, 1988; Higgins and Sharp, *CABIOS,* 5: 151, 1989; Corpet et al., *Nucleic Acids Research,* 16; 10881, 1988; and Pearson and Lipman, *Proc. Natl. Acad. Sci. U.S.A.,* 85: 2444, 1988. Altschul et al., *Nature Genet.,* 6: 119, 1994, presents a detailed consideration of sequence alignment methods and homology calculations.

The NCBI Basic Local Alignment Search Tool (BLAST) (Altschul et al., *J. Mol. Biol.,* 215: 403, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available on the NCBI website on the internet. Other specific, non-limiting examples of sequence alignment programs specifically designed to identify conserved regions of genomic DNA of greater than or equal to 100 nucleotides are PIPMaker (Schwartz et al., *Genome Research,* 10: 577-586, 2000) and DOTTER (Erik et al., *Gene,* 167: GC1-10, 1995).

Homologues and variants of a TERT promoter or artificial TERT promoter sequence are typically characterized by possession of at least 75%, for example at least 80%, 85%, 90%, 95%, 98%, or 99%, sequence identity counted over the full length alignment with the originating nucleic acid sequence (i.e., TERT promoter or artificial TERT promoter, respectively) using the NCBI Blast 2.0, set to default parameters. Methods for determining sequence identity over short windows are available at the NCBI website on the internet. One of skill in the art will appreciate that these sequence identity ranges are provided for guidance only; it is entirely possible that strongly significant homologues could be obtained that fall outside of the ranges provided.

Alternatively, sequence identity exists when a nucleic acid or fragment thereof hybridizes to another nucleic acid, to a strand of another nucleic acid, or to the complementary strand thereof, under selective hybridization conditions. Typically, selective hybridization will occur when there is at least about 75%, at least about 80%, at least about 85%, at least about 90%, at least about 95%, at least about 98%, or at least about 99% sequence identity, over a stretch of at least about 25, at least about 50, at least about 100, at least about 250, at least about 500, at least about 1000, at least about 1500, at least about 2000, at least about 2500 or at least about 3000 nucleotides.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters, including temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See, Sambrook et al., *Molecular Cloning—A Laboratory Manual,* 2nd edition, New York: Cold Spring Harbor Laboratory Press, 1989.

The Tm for a particular DNA-DNA hybrid can be estimated by the formula: Tm=81.5° C.+16.6($\log_{10}$[Na$^+$])+0.41(% G+C)−0.63(% formamide)−(600/1), where 1 is the length of the hybrid in base pairs.

The Tm for a particular RNA-RNA hybrid can be estimated by the formula: Tm=79.8° C.+18.5($\log_{10}$[Na$^+$])+0.58(% G+C)+11.8(% G+C)$^2$−0.35(% formamide)−(820/1).

The Tm for a particular RNA-DNA hybrid can be estimated by the formula: Tm=79.8° C.+18.5($\log_{10}$[Na$^+$])+0.58(% G+C)+11.8(% G+C)$^2$−0.50(% formamide)−(820/1).

In general, the Tm decreases by 1-1.5° C. for each 1% of mismatch between two nucleic acid sequences. Thus, one of ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10-15° C. would be subtracted from the calculated Tm of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well-known in the art.

An example of stringent hybridization conditions for hybridization of complementary nucleic acid sequences having more than 100 complementary residues on a filter in a Southern or Northern blot or for screening a library is 50% formamide/6×SSC at 42° C. for at least ten hours and preferably overnight (approximately 16 hours). Another example of stringent hybridization conditions is 6×SSC at 68° C. without formamide for at least ten hours and preferably overnight. An example of moderate stringency hybridization conditions is 6×SSC at 55° C. without formamide for at least ten hours and preferably overnight. An example of low stringency is 6×SSC at 42° C. for at least ten hours. Hybridization conditions to identify nucleic acid sequences that are similar but not identical can be identified by experimentally changing the hybridization temperature, e.g., from about 68° C. to 42° C., while keeping the salt concentration constant (e.g., 6×SSC), or keeping the hybridization temperature and salt concentration constant (e.g., 42° C. and 6×SSC) and varying the formamide concentration, e.g., from 50% to 0%. Hybridization buffers may also include blocking agents to lower background. These agents are well-known in the art. See Sambrook et al., *Molecular Cloning—A Laboratory Manual,* 2nd edition, New York: Cold Spring Harbor Laboratory Press, 1989; Ausubel et al., *Current Protocols in Molecular Biology,* New York: John Wiley & Sons, 1999; and Sambrook et al., *Molecular Cloning—A Laboratory Manual,* 3rd edition, New York: Cold Spring Harbor Laboratory Press, 2001.

Wash conditions also can be altered to change stringency conditions. An example of stringent wash conditions is a 0.2×SSC wash at 65° C. for 15 minutes. A high stringency wash may be preceded by a low stringency wash to remove excess probe. An exemplary medium stringency wash for duplex DNA of more than 100 base pairs is 1×SSC at 45° C. for 15 minutes. An exemplary low stringency wash for such a duplex is 4×SSC at 40° C. for 15 minutes. In general, a signal-to-noise ratio of 2× or higher than that observed for an unrelated probe in the particular hybridization assay indicates detection of a specific hybridization.

As defined herein, nucleic acid molecules that do not hybridize to each other under stringent conditions are still substantially similar to one another if they encode polypeptides that are substantially identical to each other. This occurs, for example, when a nucleic acid molecule is created synthetically or recombinantly using high codon degeneracy as permitted by the redundancy of the genetic code.

Hybridization conditions for nucleic acid molecules that are shorter than 100 nucleotides in length (e.g., for oligonucleotide probes) may be calculated by the formula: Tm=81.5° C.+16.6($\log_{10}$[Na$^+$])+0.41(% G+C)−(600/N), wherein N is chain length and the [Na$^+$] is 1M or less. See Sambrook et al., *Molecular Cloning—A Laboratory Manual,* 2nd edition, New York: Cold Spring Harbor Laboratory Press, 1989. For hybridization of probes shorter than 100 nucleotides, hybridization is usually performed under stringent conditions (e.g., 5-10° C. below the Tm) using high concentrations (e.g., 0.1-1.0 pmol/ml) of probe. See Sambrook et al., *Molecular Cloning—A Laboratory Manual, 2nd edition*, New York: Cold Spring Harbor Laboratory Press, 1989. Determination of hybridization using mismatched probes, pools of degenerate probes or "guessmers," as well as hybridization solutions and methods for empirically determining hybridization conditions are well-known in the art. See, e.g., Sambrook et al., *Molecular Cloning—A Laboratory Manual, 2nd edition*, New York: Cold Spring Harbor Laboratory Press, 1989; Ausubel et al., *Current Protocols in Molecular Biology*, New York: John Wiley & Sons, 1999.

Silencer: A cis-acting regulatory sequence that can decrease levels of transcription of an operably linked nucleic acid sequence. A silencer is activated by the specific binding of a trans-acting factor. Silencer function does not depend on the distance of the silencer from, or its orientation with respect to, the operably linked nucleic acid sequence. For instance, silencers can affect the transcription of operably linked nucleic acid sequences that are located near to, or many tens of kilobases away from the silencer. Similarly, silencers can suppress transcription when placed either upstream or downstream of a transcription initiation site and/or in either a forward or backward orientation. Silencers may, but need not, contain multiple functional sequence elements that bind different trans-acting factors. A "tissue-specific" silencer functions only in certain tissues. Such tissue-specific regulation by a silencer may result, e.g., because the trans-acting factor(s) that specifically interact with the silencer are expressed in some cell types, but not others.

Trans-acting factor: A factor, e.g., a protein or protein complex, that specifically interacts with a cis-acting element. The specific interaction, e.g., specific binding, of a trans-acting factor with a cis-acting element affects transcription of a nucleic acid sequence operably linked to the cis-acting element. For example, the binding of a trans-acting factor to a cis-acting element may initiate, upregulate or downregulate the transcription of an operably linked nucleic acid sequence. A myriad of known transcription factors are examples of trans-acting factors. More specifically, for example, c-Myc is one of several trans-acting factors known to interact with an E-box element.

Transformed or Transduced or Transfected: A transformed cell is a cell into which has been introduced a nucleic acid molecule by molecular biology techniques. The term "transformed" is synonymous with the terms "transduced" and "transfected," and such terms are used interchangeably in this disclosure. As used herein, the term transformation (or its synonyms) encompasses all techniques by which a nucleic acid molecule might be introduced into such a cell, including, without limitation, transfection with viral vectors, transformation with plasmid vectors, and introduction of naked DNA by electroporation, calcium phosphate precipitation, lipofection, ligand-mediated endocytosis of poly-lysine-DNA complex, and particle gun acceleration.

Vector or Plasmid: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. "Comprising" means "including," hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Embodiments

Provided herein in a first embodiment are regulatory control sequences that include a promoter, which directs differential expression of an operably linked heterologous nucleic acid sequence, linked in cis with at least one exogenous E-box element, where the presence of the E-box element in the regulatory control sequence enhances differential expression by the promoter.

In some specific examples, the promoter is a TERT promoter, or in more specific examples, an hTERT promoter.

In other specific examples, the promoter is residues 2251-3920 of SEQ ID NO: 1; residues 1-3955 of SEQ ID NO: 1; residues 2791-3955 of SEQ ID NO: 1; residues 2967-3955 of SEQ ID NO: 1; residues 3531-3955 of SEQ ID NO: 1; 3612-3955 of SEQ ID NO: 1; residues 3661-3955 of SEQ ID NO: 1; residues 3705-3955 of SEQ ID NO: 1; 3828-3955 of SEQ ID NO: 1; or residues 3883-3955 of SEQ ID NO: 1.

Still further examples of the promoter include nucleic acid sequences that have at least 90% sequence identity with, or hybridize under stringent conditions to, residues 2251-3920 of SEQ ID NO: 1; residues 1-3955 of SEQ ID NO: 1; residues 2791-3955 of SEQ ID NO: 1; residues 2967-3955 of SEQ ID NO: 1; residues 3531-3955 of SEQ ID NO: 1; 3612-3955 of SEQ ID NO: 1; residues 3661-3955 of SEQ ID NO: 1; residues 3705-3955 of SEQ ID NO: 1; 3828-3955 of SEQ ID NO: 1; residues 3883-3955 of SEQ ID NO: 1.

In some embodiments, the regulatory control sequence includes more than one E-box element. In some specific examples, the regulatory control sequence includes three E-box elements.

In other examples, at least one E-box element is located 3' of the promoter. In certain specific embodiments, the regulatory control sequence has the structure 5'-promoter-(E-box)$_n$-3', where "n" is any integer equal to or greater than one.

Other examples of the provided regulatory control sequence also include a heterologous nucleic acid sequence operatively linked thereto. In some specific examples, the heterologous nucleic acid sequence encodes a cytotoxin or therapeutic substance. In other specific examples, the regulatory control sequence has the structure 5'-promoter-(E-box)$_n$-heterologous sequence-3', where "n" is any integer equal to or greater than one.

Still further embodiments provided herein include regulatory control sequences that include a TERT promoter and at least one exogenous E-box element linked in cis, where the TERT promoter (without exogenous E-box element(s) linked in cis) and the regulatory control sequence (with exogenous E-box element(s)) are each separately capable of directing the differential expression of an operably linked heterologous nucleic acid sequence; and where the differential expression of the heterologous nucleic acid sequence by the regulatory control sequence is enhanced as compared to the differential expression of the heterologous nucleic acid sequence by the TERT promoter.

Still other examples of the regulatory control sequence include the nucleic acid sequence set forth in SEQ ID NO: 8 or SEQ ID NO: 9.

Other embodiments include expression vectors including the provided regulatory control sequences. In specific examples, the expression vectors are viral vectors or plasmid vectors. Further embodiments include host cells transformed with the provided vectors. Specific examples of host cells include eukaryotic cells or prokaryotic cells.

Also provided herein are methods for treating cancer in a patient by administering a therapeutically effective amount of a vector provided herein to a patient. Other embodiments include methods of inhibiting the growth of cancer cells by introducing a growth inhibitory amount of a vector provided herein into a cancer cell.

Further provided embodiments are kits, which include an expression vector including an artificial TERT promoter and a polylinker. Other kit embodiments include an expression vector including a heterologous nucleic acid sequence under the control of an artificial TERT promoter. In some specific kit embodiments, the heterologous nucleic acid sequence encodes a reporter protein or a cytotoxin.

IV. Artificial TERT Promoter

Disclosed herein are artificial TERT promoters that may be used to enhance differential expression of operably linked heterologous nucleic acid sequences. An artificial TERT promoter comprises a TERT promoter that has been linked in cis with at least 1, at least 2, at least 3, at least 4, at least 5, at least 7, at least 10, at least 12, at least 15, at least 20, or at least 25 exogenous cis-acting element(s). In certain embodiments, the cis-acting element(s) is (are) one or more exogenous E-box element(s), e.g., at least 1, at least 2, at least 3, at least 4, at least 5, at least 7, at least 10, at least 12, at least 15, at least 20, or at least 25 exogenous E-box elements. The TERT promoter and exogenous E-box element(s) may be combined by any method known in the art. Numerous recombinant DNA methods are known by which a TERT promoter may be linked in cis with exogenous E-box elements; see, e.g., Sambrook et al., *Molecular Cloning—A Laboratory Manual, 2nd edition*, New York: Cold Spring Harbor Laboratory Press, 1989; Ausubel et al., *Current Protocols in Molecular Biology*, New York: John Wiley & Sons, 1999; and Sambrook et al., *Molecular Cloning—A Laboratory Manual, 3rd edition*, New York: Cold Spring Harbor Laboratory Press, 2001.

The TERT promoter and exogenous E-box element(s) may be placed in any orientation with respect to each other, e.g., upstream (i.e., 5') or downstream (i.e., 3'). In one embodiment, at least one exogenous E-box element is located downstream (i.e., 3') of the TERT promoter. In other embodiments, at least one exogenous E-box element is located upstream (i.e., 5') of the TERT promoter. In yet other embodiments, each of several exogenous E-box element is located downstream (i.e., 3') of the TERT promoter, or each of several exogenous E-box element is located upstream (i.e., 5') of the TERT promoter. The TERT promoter and any exogenous E-box element may also be located on the same or different strands of a double-stranded nucleic acid molecule. In another embodiment, the sense orientation of the TERT promoter and each exogenous E-box element of an artificial promoter are located on the same nucleic acid strand of a double-stranded nucleic acid molecule.

The TERT promoter and any exogenous E-box element may be separated by any number of nucleotides as long as the differential repressive effect described herein is observed. For example, there may be at least about 2, at least about 5, at least about 10, at least about 20, at least about 50, at least about 100, at least about 250, at least about 500, at least about 1000, at least about 2000 nucleotides separating the TERT promoter and any one exogenous E-box element. In one embodiment, the TERT promoter is separated from an exogenous E-box element by 13 nucleotides. Moreover, in an artificial TERT promoter comprising more than one exogenous E-box element, the exogenous E-box elements may be separated from one another by any number of nucleotides as long as the effect on differential expression is still achieved. For example, there may be at least about 2, at least about 5, at least about 10, at least about 20, at least about 50, at least about 100, at least about 250, at least about 500, at least about 1000, at least about 2000 nucleotides separating exogenous E-box elements in an artificial TERT promoter. In one embodiment, two exogenous E-box elements are separated from one another by four nucleotides. In another embodiment, three exogenous E-box elements are aligned in series, and each E-box element in the series is separated from the adjoining E-box element by four nucleotides.

In certain embodiments, an artificial TERT promoter has the structure: 5'-$(nt)_{x1}$-TERT promoter-$(nt)_{x2}$-(exogenous E-box element)$_{x3}$-$(nt)_{x4}$-3', where "nt" is any nucleotide, and "x1, x2, x3 and x4" may be any integer. Certain artificial hTERT promoter embodiments having this structure include, without limitation, the nucleic acid sequences set forth in SEQ ID NO: 8, and SEQ ID NO: 9.

TERT Promoter of an Artificial TERT Promoter

A TERT promoter element of an artificial TERT promoter may include all or any portion of any TERT promoter sequence known in the art, including TERT promoter sequences now or hereafter characterized in any living species, e.g., humans, mouse, or hamster; provided that such TERT promoter or portion thereof is differentially regulated in at least two cell types, e.g., cancer cells and normal, somatic cells. For example, numerous hTERT promoter sequences that are differentially regulated in cancer cells and normal, somatic cells, or in immortalized cells and normal, somatic cells are disclosed herein, including the hTERT promoter sequences listed in Table 1.

TERT promoter variants are also envisaged by this disclosure. Variant TERT promoter sequences may be produced, e.g., by standard DNA mutagenesis techniques, including without limitation M13 primer mutagenesis. Details of these techniques are provided in Sambrook et al., *Molecular Cloning: A Laboratory Manual*, New York: Cold Spring Harbor Laboratory Press, 1989, Ch. 15. Mutagenesis of TERT promoter sequences are also described in Example 6. By the use of molecular engineering techniques well known in the art, variants may be created that differ from the TERT promoter sequences disclosed. DNA molecules and nucleotide sequences that are derivatives of those specifically disclosed herein, and which differ from those disclosed by the deletion, addition, or substitution of nucleotides while retaining the capability of directing differential expression of an operably linked heterologous nucleic acid sequence are comprehended by this disclosure. Also comprehended are more closely related nucleic acid molecules that share at least 80%, at least 85%, at least 90%, at least 95%, or at least 98% nucleotide sequence homology with the disclosed TERT promoter sequences.

Nucleic acid molecules that are derived from the TERT promoter sequences disclosed include molecules that hybridize under stringent conditions to the disclosed TERT promoter nucleic acid sequences, or fragments thereof. Useful hybridization conditions are described in Section II of this disclosure.

One of skill in the art can readily identify TERT promoter sequences (or variants) thereof that are capable of directing differential expression of an operably linked heterologous nucleic acid sequence. For example, a skilled artisan may engineer a vector having a reporter gene under the control of a TERT promoter sequence (or variant), and measure reporter gene activity in cells transfected with the vector. When normalized for differences in transfection efficiency, which is a standard correction well known in the art, reporter gene activity will differ between cell types for a differentially regulated TERT promoter (or variant). For example, the activity of the reporter gene may be higher in a cancer cell (such as an R$^-$ cancer cell) as compared to a normal, somatic cell. The activity of the reporter gene may be at least about 2-fold, at least about 3-fold, at least about 4-fold, at least about 5-fold, at least about 10-fold, at least about 20-fold, at least about 50-fold, at least about 100-fold, or at least about 200-fold times higher in the cancer cell as compared to the normal, somatic cell.

The reporter gene described in the preceding paragraph may, e.g., encode an enzyme which catalyses a reaction which produces a detectable signal, preferably a visually detectable signal, such as a colored product. Many examples are known, including β-galactosidase and luciferase. β-galactosidase activity may be assayed by production of blue color on substrate, the assay being by eye or by use of a spectrophotometer to measure absorbance. Fluorescence, for example that produced as a result of luciferase activity, may be quantified using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labeled directly or indirectly using any standard technique. Those skilled in the art are well aware of a multitude of possible reporter genes and assay techniques which may be used to determine transcriptional activity. Any suitable reporter/assay may be used and it should be appreciated that no particular choice is essential to or the present disclosure.

Exogenous E-Box Elements

E-box elements were first recognized as cis-acting elements involved in activating transcription of the immunoglobulin heavy chain (IgH). Several of these cis-acting elements were identified in both the IgH gene promoter (containing five E-box elements) and in the Ig kappa light-chain gene promoter (containing three E-box elements), and were found to share a signature motif consisting of the core hexa-nucleotide sequence, CANNTG. E-box elements have been subsequently found in numerous other promoters, including some promoters that regulate cell-specific gene expression.

A large family of trans-acting factors are known to specifically bind to E-box elements and thereby regulate transcription of promoters containing such elements. These trans-acting factors share a conserved helix-loop-helix (HLH) structural motif. Over 240 HLH proteins have been identified in a wide range of organisms. HLH proteins may either activate or inhibit transactivation upon binding an E-box element. For a review of E-box elements and HLH proteins, see, e.g., Massari and Murre, Mol. Cell. Biol., 20(2): 429-440, 2000.

Exogenous E-box elements as disclosed herein may be synthesized, either individually or as multimers, using techniques commonly known in the art. Alternatively, exogenous E-box elements may be excised from any nucleic acid source containing an E-box element; in which case, non-E-box sequences included in the excised nucleic acid fragment would preferably lack regulatory control elements (e.g., core promoter elements, enhancers or silencers).

The exogenous E-box elements disclosed herein may have any sequence consistent with the E-box sequence, CANNTG. Thus, any nucleotide may be substituted at either position designated by an "N" in the sequence. In certain embodiments, the E-box element has the sequence, CACGTG.

V. Expression Systems

An artificial TERT promoter can be included in an expression vector to direct the expression of an operably linked heterologous nucleic acid sequence. Such expression vector may optionally contain auxiliary expression control sequences, including without limitation core promoter sequences, transcription initiators, transcription terminators, a start codon (i.e., ATG) preceding a protein-encoding nucleic acid sequence, splicing signal for introns, maintenance of the correct reading frame of that nucleic acid sequence to permit proper translation of mRNA, and stop codons. Generally, auxiliary expression control sequences will include the minimal sequence sufficient to support transcription.

The expression vector typically contains an origin of replication and specific genes which allow phenotypic selection of transformed cells. Vectors suitable for use include, but are not limited to, the pGL3-Basic (Promega) expression vector for expression in eukaryotic cells.

In certain embodiments, an expression vector includes a nucleic acid sequence encoding a polypeptide of interest. A polypeptide of interest can be a polypeptide that affects a function of the transfected cell. Polypeptides of interest include, but are not limited to, polypeptide cytotoxins. A polypeptide of interest can also be a marker polypeptide, which is used to identify a cell of interest. Marker polypeptides include fluorescent polypeptides, enzymes, or antigens that can be identified using conventional molecular biology procedures. For example, the polypeptide can be a fluorescent marker (e.g., green fluorescent protein, *Aequoria Victoria*, or *Discosoma* DSRed), an antigenic markers (e.g., human growth hormone, human insulin, human HLA antigens), a cell surface marker (e.g., CD4, or any cell surface receptor), or an enzymatic marker (e.g., lacZ, alkaline phosphatase). Techniques for identifying these markers in host cells include immunohistochemistry and fluorescent microscopy, and are well known in the art. In other embodiments, the expression vector may include a polylinker (i.e., a multiple cloning site) to permit insertion of a nucleic acid sequence encoding a polypeptide of interest.

RNA molecules transcribed from an expression vector need not always be translated into a polypeptide to express a functional activity. Specific non-limiting examples of other molecules of interest include antisense RNA molecules complementary to an RNA of interest, ribozymes, small inhibitory RNAs, and naturally occurring or modified tRNAs.

Expression vectors including an artificial TERT promoter can be used to transform host cells. Hosts can include isolated microbial, yeast, insect and mammalian cells, as well as cells located in the organism. Biologically functional viral and plasmid DNA vectors capable of expression and replication in a host are known in the art, and can be used to transfect any cell of interest. Where the cell is a mammalian cell, the genetic change is generally achieved by introduction of the DNA into the genome of the cell (i.e., stable) or as an episome.

Transfection of a host cell with recombinant nucleic acid molecule may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, transfection of nucleic acid molecules may be achieved by, e.g., calcium phosphate coprecipitates, microinjection, electroporation, insertion of a plasmid encased in liposomes, or use of virus vectors. Eukaryotic cells can also be transformed with more than one nucleic acid molecule; thus, e.g., a eukaryotic cell may be co-transfected with an artificial TERT promoter expression vector and a second foreign nucleic acid molecule encoding a helper protein or a selectable marker. Other useful methods use nucleic acid delivery vehicles derived from viruses, including but not limited to adenoviruses, retroviruses, vaccinia viruses, lentiviruses, and adeno-associated viruses (see, for example, *Eukaryotic Viral Vectors*, Cold Spring Harbor Laboratory Press, Gluzman ed., 1982).

There are several ways to administer recombinant viral expression vectors. For example, such vectors may be directly injected into a solid tumor present in a subject's body (e.g., Haddada et al., *Biochem. Biophys. Res. Comm.*, 195: 1174-1183, 1993; Vincent et al., *Hum. Gene Ther.*, 7: 197-205, 1996). An alternative way of delivering genetic material into solid tumors and/or their metastases is by administering the recombinant viral vector via the blood or lymphatic circulation. All established tumors, both primary and metastatized, that are larger than a few millimeter in diameter are vascularized (Folkman et al., *J. Nat. Cancer Inst.*, 82: 4, 1990; Folkman and Shing, *J. Biol. Chem.*, 267: 10931-10934, 1992). However, it is sometimes preferred that systemic treatment using recombinant viral vectors is restricted to certain tissues, organs, or extremities, or certain combinations thereof. Thus, systemic treatment may include isolated tissue, organ or extremity perfusion (as described, e.g., in U.S. Pat. No. 6,495,131).

VI. Enhanced Differential Expression for Nucleic-Acid-Based Therapy

One hurdle facing medical genetic approaches to combating disease is how to achieve specificity. That is, how to preferentially express the therapeutic nucleic acid in the disease cells and avoid side effects in normal cells. For example, the expression of a cellular toxin in a cancer cell is useful to kill the cancer cells; however, even a small amount of cytotoxin expressed in a normal cell may have undesirable side effects. The artificial TERT promoters disclosed herein are useful to enhance the differential expression of therapeutic nucleic acids, such as cytotoxins. Thus, high level expression of a therapeutic nucleic acid, such as a cytotoxin, can be maintained in $R^-$ cells, such as many cancer cells, while expression of the therapeutic nucleic acid is preferentially decreased in a normal cell. Hence, the side effects of nucleic-acid-based therapy directed by an artificial TERT promoter in a normal cell will be lessened.

Based on this disclosure (see, e.g., Example 15) and knowledge in the art, a skilled artisan will appreciate how to identify $R^-$ cells. For example, after normalization for transfection efficiency, the activity of a reporter gene under the control of an artificial TERT promoter in a transfected $R^-$ cell will not be significantly decreased when compared to the activity of the same reporter gene under the control of the TERT promoter element alone in the same $R^-$ cell type.

A clinician may identify whether a patient's tumor comprises $R^-$ cells, e.g., by testing cells taken from a biopsy of the tumor as described above. Once the presence of $R^-$ cells has been established, then artificial TERT promoters as described herein may be used to enhance the differential expression of an operably linked nucleic acid sequence in the $R^-$ cells as compared to normal cells in the patient; thereby, killing, for example, $R^-$ cancer cells with lessened side effects on normal cells.

VII. Pharmaceutical Compositions and Administration

Expression vectors containing an artificial TERT promoter can be administered directly to the subject for the suppression of tumor cell growth and proliferation. Pharmaceutical compositions that include artificial TERT promoter vectors can be formulated with an appropriate solid or liquid carrier, depending on the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations can be liquid (e.g. syrups, solutions or suspensions), or solid (e.g. powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that comprise an artificial TERT promoter vector in some embodiments of the disclosure will be formulated in unit dosage form, suitable for individual administration of precise dosages. For example, one possible unit dosage can contain from about 1 mg to about 1 g of artificial TERT promoter vector. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The nucleic acids of this disclosure can be administered to humans or other animals on whose cells they are effective in various manners such as topically, orally, intravenously, intramuscularly, intraperitoneally, intranasally, intradermally, intrathecally, and subcutaneously. The particular mode of administration and the dosage regimen will be selected by the attending clinician, taking into account the particulars of the case (e.g. the subject, the disease, the disease state involved, and whether the treatment is prophylactic). Treatment can involve daily or multi-daily doses of nucleic acid(s) over a period of a few days to months, or even years.

A therapeutically effective amount of an artificial TERT promoter vector can be the amount of vector necessary to inhibit further growth of a tumor or the amount necessary to suppress the growth of a tumor. In another embodiment, a therapeutically effective amount of an artificial TERT promoter vector tumor suppressor can be the amount of vector necessary to eliminate a tumor. Specific tumor suppressive effects that can be caused by an artificial TERT promoter vector are described herein. In some embodiments, a tumor suppressive amount of an artificial TERT promoter vector is an amount sufficient to eliminate a tumor (for instance, any of the tumor suppressive amounts discussed herein) without causing a substantial cytotoxic effect (e.g. without killing more than 10% of cells in a sample).

An effective amount of an artificial TERT promoter vector can be administered in a single dose, or in several doses, for example daily, during a course of treatment. However, the effective amount of vector will be dependent on the subject being treated, the severity and type of the affliction, and the manner of administration of the therapeutic(s). For example, a therapeutically effective amount of an artificial TERT promoter vector can vary from about 0.1 mg/Kg body weight to about 1 g/Kg body weight.

Site-specific administration of the disclosed compounds can be used, for instance by applying an artificial TERT promoter vector to a pre-cancerous region, a region of tissue from which a neoplasm has been removed, or a region suspected of being prone to neoplastic development. In some embodiments, sustained intra-tumoral (or near-tumoral) release of the pharmaceutical preparation that comprises a therapeutically effective amount of an artificial TERT promoter vector may be beneficial. Slow-release formulations are known to those of ordinary skill in the art. By way of example, polymers such as bis(p-carboxyphenoxy)propane-sebacic-acid or lecithin suspensions may be used to provide sustained intra-tumoral release. By way of further example, delivery may be via an injected and/or implanted drug depot, for instance comprising multi-vesicular liposomes such as in DepoFoam (SkyePharma, Inc, San Diego, Calif.) (see, for instance, Chamberlain et al., *Arch. Neuro.* 50:261-264, 1993; Katri et al., *J. Pharm. Sci.* 87:1341-1346, 1998; Ye et al., *J. Control Release* 64:155-166, 2000; and Howell, *Cancer J.* 7:219-227, 2001).

It is specifically contemplated in some embodiments that delivery is via an infectious particle or viral vector injected and/or implanted at the tumor site, as discussed previously (see, e.g., Gu et al., *Oncogene*, 21: 4757-4764, 2002; Indraccolo, et al., *Cancer Res.* 62: 6099-6107, 2002).

VIII. Kits

Kits for Expression of Heterologous Nucleic Acid Sequences under the Control of an Artificial TERT Promoter The artificial TERT promoters disclosed herein can be supplied in the form of a kit for use in expressing heterologous nucleic acid sequences, for instance, nucleic acid sequences encoding cytotoxins or therapeutic substances, or, for instance, reporter genes. In one embodiment of such a kit, an appropriate amount of one or more expression vectors comprising an artificial hTERT promoter and, optionally, a polylinker is provided in one or more containers. The vector optionally contains any auxiliary expression control sequences, such as core promoter elements, that may be useful for transcription of an expression cassette to be initiated. The polylinker may be used to insert any transcribable nucleic acid sequence into the vector; thereby, placing such nucleic acid sequence under the transcriptional control of the artificial TERT promoter. Alternatively, the vector may contain a transcribable nucleic acid sequence instead of or in addition to a polylinker. Any heterologous nucleic acid sequence is contemplated herein. In some embodiments, the heterologous nucleic acid sequence encodes one or more cytotoxins or therapeutic substances. In other embodiments the heterologous nucleic acid sequence encodes a protein that confers cellular resistance to an externally applied substance. In still other embodiments, the heterologous nucleic acid sequence is a reporter gene.

In some embodiments, the expression vector(s) supplied in the kit is suitable for expression of heterologous nucleic acid sequences under the control of an artificial TERT promoter in eukaryotic cells, such as yeast cells or mammalian cells or, more particularly, human cells. In another embodiment, the expression vector(s) is suitable for expression of one or more heterologous nucleic acid sequences under the control of an artificial TERT promoter in prokaryotic cells, such as bacteria. In some embodiments, the expression vector is a viral vector, and in some of these embodiments, helper vectors and/or packaging vectors are optionally included in the kit.

In some embodiments, the expression vectors in the kit may be provided suspended in an aqueous solution or as a freeze-dried or lyophilized powder, for instance. The container(s) in which the expression vectors are supplied can be any conventional container that is capable of holding the supplied form, for instance, microfuge tubes, ampoules, or bottles.

The amount of each expression vector contained in the kit can be any appropriate amount, depending for instance on the market to which the product is directed. In one embodiment, the kit is adapted for research or clinical use and the amount of each expression vector is sufficient to perform one or more transformations of one or more host cells. Those of ordinary skill in the art know the amount of expression vector that is appropriate for use in a transformation reaction. General guidelines may for instance be found in Sambrook et al. (In *Molecular Cloning: A Laboratory Manual*, Cold Spring Harbor, N.Y., 1989), and Ausubel et al. (In *Current Protocols in Molecular Biology*, John Wiley & Sons, New York, 1998).

In other embodiments, reaction vessels and auxiliary reagents such as chromogens, buffers, media, enzymes, etc. also may be included in the kits.

Kits for Identifying R⁻ Cells

Kits similar to those disclosed above for the expression of heterologous nucleic acid sequences under the control of an artificial TERT promoter can be used to identify R⁻ cells (see section IV, for example). One embodiment of such a kit may include an appropriate amount of one or more expression vectors comprising an artificial hTERT promoter and a reporter gene, similarly to those provided above. The amount of each expression vector comprising an artificial hTERT promoter supplied in the kit can be any appropriate amount, for example an amount of each expression vector sufficient to transform one or more host cells.

In some embodiments, kits for identifying R⁻ cells may also include control cells, and/or control vectors, and/or instructions, e.g., for carrying out transformations in control and test cells. Other optional kit components may be as described above.

Kits for Identifying Modulators of Differential Expression by an Artificial TERT Promoter Also provided are kits useful for the identification of compounds that enhance differential expression or modulate enhancement of differential expression. In one embodiment, such kits provide the materials necessary to assess the transcriptional activity of an artificial TERT promoter in vitro. In one embodiment, a kit contains a vector comprising an artificial TERT promoter linked in cis with a heterologous nucleic acid sequence having measurable activity on or in a transformed host cell. In some embodiments, the heterologous nucleic acid sequence is a reporter gene. In other embodiments, the heterologous nucleic acid sequence encodes a protein that affects the cell in a way that can be measured, e.g., a protein that causes cell death or confers resistance to an otherwise toxic substance. In another embodiment, the kit contains at least two cell lines wherein differential expression of an artificial TERT promoter is known to be enhanced. In yet another embodiment, a control vector comprising only a TERT promoter is included. Other optional kit components may be as described above.

The following examples are provided to illustrate certain particular features and/or embodiments. These examples should not be construed to limit the invention to the particular features or embodiments described.

EXAMPLES

Example 1

Isolation and Sequence Analysis of hTERT Genomic Clones

Two independent methods were applied to obtain genomic DNA clones containing the 5'-flanking region of the hTERT gene: PCR-based genomic walking and BAC (bacterial artificial chromosome) library screening.

For the PCR-based method, the Human Genome Walker Kit (Clontech Labs, Inc., Palo Alto, Calif.) was used according to the supplier's protocol. The gene-specific primers within the 5'-region of hTERT cDNA were 5'-AGC ACT CGG GCC ACC AGC TCC T-3' (primer GW1; SEQ ID NO: 3) for the initial PCR and 5'-AAC GTG GCC AGC GGC AGC ACC T-3' (primer GW2, SEQ ID NO: 4) for the nested PCR. The use of Advantage-GC Genomic PCR Kit (Clontech Labs, Inc.) designed for PCR of highly GC-rich regions was useful for the amplification step. The final PCR product (approximately 1.8 kb in length) (corresponding to −1665 to +135 in FIG. 1, and residues 2251 to 4050 of SEQ ID NO: 1) was cloned into pCR2.1 vector (Invitrogen, Corp., San Diego, Calif.) via TA cloning method, and sequenced in both strands by the dRhodamine terminator cycle sequencing kit (PE Applied Biosystems, Foster City, Calif.).

The RPCI-11 human BAC library (available, e.g., from Invitrogen) was screened using a 430-bp hTERT cDNA fragment (nucleotides 18 to 447 in GenBank AF015950; SEQ ID NO: 5) as a hybridization probe at the Research Genetics, Inc., Huntsville, Ala. Two resultant positive BAC clones were sequenced by the BigDye terminator cycle sequencing kit (PE Applied Biosystems) using primers (SEQ ID NOs: 14-18) that were designed based on the sequences from the PCR-based clones described above. The sequences of the BAC clones corresponded to a portion of the 5'-flanking region, exon 1 and intron 1, as shown in FIG. 1 (corresponding to residues 2251 to 4293 of SEQ ID NO: 1).

The nucleotide sequences from the PCR-based clones and the two BAC clones were identical except for a few possible polymorphisms. For example, nucleotides −1327 and −913 in FIG. 1 (corresponding to residues 2589 and 3003 of SEQ ID NO: 1) were each found to be "C" in one PCR-based clone and one BAC clone; however the nucleotides at those positions were found to be "T" in the second BAC clone. Similarly, nucleotide −372 in FIG. 1 (corresponding to residue 3544 of SEQ ID NO: 1) was found to be "T" in a PCR-based clone, and "C" in the two BAC clones.

A DNA homology search was performed at the National Center for Biotechnology Information (NCBI) using the basic local alignment search tool (BLAST) network service. Potential transcription factor binding sites were predicted by the TESS search program (available on the website of the Computation Biology and Informatic Laboratory at the University of Pennsylvania; Schug and Overton, *TESS: Transcription Element Search Software on the WWW*, Technical Report CBIL-TR-1997-1001-v0.0, Computational Biology and Informatics Laboratory, School of Medicine, University of Pennsylvania, 1997). A search for CpG islands was carried out using GRAIL (Gene Recognition and Assembly Internet Link, Version 1.3; available on the Oak Ridge National Laboratory website entitled "Computational Biology at ORNL"). The hTERT promoter sequence shown in FIG. 1 (corresponding to residues 2251 to 4293 of SEQ ID NO: 1) is available in GenBank (accession no. AF098956).

The hTERT promoter region is highly GC-rich. Search by GRAIL identified a CpG island of 1138 bps in length (−808 to +330 in FIG. 1, corresponding to residues 3108 to 4245 of SEQ ID NO: 1), with a GC content of 71.3% and a ratio of observed versus expected CpGs of 0.79. A DNA homology search by BLAST of known sequences in GenBank showed that the 65-bp sequence (−371 to −307 in FIG. 1, corresponding to residues 3545 to 3609 of SEQ ID NO: 1) is identical to the cellular sequence of the integration site of the hepatitis B virus (HBV) in the huH-4 cell line (GenBank accession no. X51995; Kekule et al., *Nature*, 343: 457-461, 1990), implying a genomic rearrangement of the hTERT gene promoter and possibly, taken together with the ribonuclease protection assay described below, a transcription initiation from a viral gene promoter in this cell line. Southern blot analysis was used to confirm the genomic rearrangement (data not shown). Although the hTERT gene promoter lacks a typical TATA box or a typical CCAAT box, as seen with many GC-rich promoters, the TESS search program predicts a number of potential transcription factor binding sites near or upstream of the major transcription initiation site, including potential binding sites for Sp1, MAZ (Myc-associated zinc finger protein), a basic-helix-loop-helix-zipper (bHLHZ) class of transcription factors (E boxes), c-Ets-2 and AP-2 (activator protein-2) (see FIG. 1).

Example 2

Determination of hTERT Transcription Initiation Sites

Ribonuclease protection assay was carried out to demonstrate the transcription initiation sites of the hTERT gene. A $^{32}$P-labeled RNA probe (460 bases in length), which corresponds to the 390-base antisense hTERT sequence from +135 (the end of GW2 primer) to −255 (PvuII site) and the pCR2.1 vector-derived 70-base sequence was synthesized by in vitro transcription using the MAXIscript T7 kit (Ambion, Inc., Austin, Tex.). Hybridization between the probe ($5 \times 10^5$ cpm per reaction) and total cellular RNA (50 µg per reaction) and digestion with RNaseA/RNaseT1 were performed using the RPA III kit (Ambion, Inc). The protected fragments were detected on a 5% denaturing polyacrylamide gel.

Multiple protected fragments ranging from approximately 120 to approximately 190 bases were reproducibly observed in the hTERT mRNA-expressing CMV-Mj-HEL-1, RCC23, huH-4 (hepatocellular carcinoma; Huh and Utakoji, *Gann*, 72: 178-179, 1981) and SiHa cells, but not in hTERT mRNA-negative SUSM-1, normal human fibroblasts and RCC23+3 cells (FIG. 2 and data not shown), supporting the presence of multiple transcription initiation sites. The most abundant fragment was approximately 135 bases in length. This supports the finding that a G nucleotide, which lies 55 bps upstream of the translational initiation codon, is a major transcription initiation site, which matches the 5'-end of the hTERT cDNA sequence reported by Nakamura et al. (*Science*, 277: 955-959, 1997). This G is referred to as +1 in this disclosure (and corresponds to residue 3916 of SEQ ID NO: 1). A 390-base fragment was protected only in the hepatocellular carcinoma cell line, huH-4, which supports an alternate transcription initiation upstream of −255 in that cell line.

Example 3

Construction of pGL3B-TRTP and pBTdel-X Luciferase Reporter Gene Constructs

Approximately 1.7-kb SacI/Eco47III fragment (residues −1665 to +5 in FIG. 1, corresponding to residues 2251 to 3920 of SEQ ID NO: 1) was ligated to the SacI/SmaI-digested pGL3-Basic vector (Promega, Madison, Wis.) to allow transcription of firefly luciferase gene under the control of this fragment. The resultant plasmid (pGL3B-TRTP) was digested with SacI and StuI, and then divided into two reactions: one was end-polished by T4 DNA polymerase and self-circularized (pBT-SE); and the other was subject to the unidirectional deletions by the Exonuclease III/Mung bean nuclease system (Stratagene Cloning Systems, La Jolla, Calif.) to make a series of constructs shown in FIG. 3 (pBT-del-X: -X means the nucleotide number in FIG. 1 where the fragment starts). A 251-bp fragment (−211 to +40 in FIG. 1, corresponding to residues 3705 to 3955 of SEQ ID NO: 1) was PCR-amplified and cloned into the SacI/SmaI-digested pGL3-Basic to produce the plasmid p2XEB. All plasmid DNAs were purified with the QIAfilter plasmid kit (Qiagen, Inc., Chatsworth, Calif.) and confirmed to have correct sequences by nucleotide sequencing, and their quantity and quality were routinely checked by agarose gel electrophoresis.

Example 4

Assays of pGL3B-TRTP and pBTdel-X Transcriptional Activity

This example demonstrates that the 1670-bp hTERT promoter fragment described in Example 3 (residues −1665 to +5 in FIG. 1, corresponding to residues 2251 to 3920 of SEQ ID NO: 1) is differentially expressed in telomerase-positive and telomerase-negative cells. In addition, this example describes a deletion analysis of the larger hTERT promoter fragment, which demonstrates some regions of the hTERT promoter that affect maximal promoter activity.

Two human cell lines positive for both telomerase activity and hTERT mRNA expression were used for the luciferase assays described in this Example. Those cell lines are: an immortalized fibroblast cell line, CMV-Mj-HEL-1 (Hensler et al., *Mol. Cell. Biol.*, 14: 2291-2297, 1994); and a uterine cervical carcinoma cell line, SiHa (Uejima et al., *Mol. Carcinog.*, 22: 34-45, 1998). Human cells that express neither telomerase activity nor the hTERT mRNA were also used for luciferase assays. Those cells are: normal human primary fibroblasts derived from foreskin; an immortalized fibroblast cell line, and SUSM-1 (Nakabayashi et al., *Exp. Cell Res.*, 235: 345-353, 1997). The expression of telomerase activity and hTERT mRNA in all of the cells and cell lines described in this example was confirmed by the telomeric repeat amplification protocol (TRAP) assay and the reverse transcription-PCR (RT-PCR), respectively, as previously described (Horikawa et al., *Mol. Carcinog.*, 22: 65-72, 1998).

hTERT mRNA-expressing and non-expressing cells (5 to $7.5 \times 10^4$) were seeded on 24-well plates, cultured overnight, and transiently transfected (1 µg per well) with pGL3B-TRTP (containing the 1670-bp hTERT promoter fragment, as described above) or pGL3-basic (containing no promoter) using the SuperFect transfection reagent (Qiagen). For better comparison among cell lines with different transfection efficiencies, the pGL3-Control plasmid (1 µg per well; Promega), the firefly luciferase gene of which is under the transcriptional control of SV40 enhancer/promoter, was also transfected into each cell line and used for normalization of the activities shown by the hTERT promoter-luciferase construct.

As shown in Table 2, pGL3B-TRTP showed significant activities in hTERT mRNA-positive cells of both fibroblastic (CMV-Mj-HEL-1) and epithelial (SiHa) origins. Specifically, pGL3B-TRTP activity was 18.3 to 30.9% of the pGL3-Control, or approximately 50 to 60-fold of the baseline activity of the pGL3-Basic vector. The highest, normalized luciferase activity observed in the CMV-Mj-HEL-1 cells is consistent with the highest expression of endogenous hTERT mRNA in this cell line, as shown in FIG. 2. In marked contrast, the pGL3B-TRTP construct resulted in no or little luciferase activity (0.2 to 1.0% of the pGL3-Control; 1.4 to 2-fold of the pGL3-Basic) in the hTERT mRNA-negative normal human fibroblasts and SUSM-1 cells.

TABLE 2 hTERT gene promoter activity in endogenous hTERT mRNA-positive and -negative human cells

| | | Firefly luciferase activity[a] | | |
|---|---|---|---|---|
| Cells | Endogenous hTERT mRNA[b] | pGL3-Basic (no promoter) | pGL3B-TRTP (hTERT promoter −1665 to +5[c]) | pGL3-Control (SV40 promoter/enhancer) |
| Fibroblastic origins | | | | |
| CMV-Mj-HEL-1 | + | 2.7 ± 0.2 (0.5%) | 171.1 ± 17.2 (30.9%) | 554.3 ± 63.3 (100%) |
| SUSM-1 | − | 1.4 ± 0.1 (0.1%) | 3.4 ± 0.6 (0.2%) | 1637.0 ± 292.6 (100%) |
| Normal human fibroblasts | − | 0.3 ± 0.1 (0.7%) | 0.4 ± 0.1 (1.0%) | 41.0 ± 5.7 (100%) |
| Epithelial origins | | | | |
| SiHa (uterine cervical carcinoma) | + | 0.4 ± 0.1 (0.4%) | 20.1 ± 3.1 (18.3%) | 109.6 ± 16.5 (100%) |

[a]Average light units and SD are shown. Luciferase activities of pGL3-Basic and pGL3B-TRTP were normalized with that of pGL3-Control for each cell line and are shown as a percentage in the parentheses.
[b]Determined by reverse transcription PCR.
[c]As numbered in FIG. 1

The data in Table 2 supports the finding that the regulation of hTERT gene expression occurs mainly at the transcriptional level, rather than at post-transcriptional level such as control of mRNA stability. This is also consistent with a finding that treatment of hTERT mRNA-negative cells with cycloheximide to diminish short-lived ribonucleases did not induce the hTERT mRNA expression (data not shown).

A series of luciferase constructs containing unidirectionally deleted fragments of the hTERT promoter in the pGL3B-TRTP plasmid were next tested in luciferase assays to demonstrate the elements responsible for the hTERT gene promoter activity. A control plasmid, pRL-SV40 (1 ng per well; Promega) containing the *Renilla reniformis* luciferase gene under the transcriptional control of SV40 enhancer/promoter, was co-transfected with the hTERT promoter-luciferase constructs (1 µg per well, as described above). The level of firefly luciferase activity was normalized to that of *Renilla reniformis* luciferase activity for each transfection.

As shown in FIG. 3, the plasmid pBTdel-279 (containing −279 to +5 in FIG. 1, corresponding to residues 3637 to 3920 of SEQ ID NO: 1) showed the highest promoter activity in the CMV-Mj-HEL-1 and SiHa cells, and pBTdel-408 (containing −408 to +5 in FIG. 1, corresponding to residues 3508 to 3920 of SEQ ID NO: 1) was highest in a renal cell carcinoma cell line, RCC23 (Horikawa et al., *Mol. Carcinog.*, 22: 65-72, 1998). Reduced activities up to approximately 50% of the full promoter activity shown by the constructs containing longer fragments might either reflect the presence of negative regulatory element(s) or be due to the lower transfection efficiency of the larger construct. It is notable that the deletion of 59-bp region from −208 to −150 in FIG. 1 (corresponding to residues 3708 to 3766 of SEQ ID NO: 1) resulted in the remarkably decreased promoter activity in all of the cell lines tested, demonstrating the presence of a cis-element(s) within this 59-bp region that imparts high promoter activity.

The 59-bp region contains a canonical E-box (CACGTG, −187 to −182 in FIG. 1, corresponding to residues 3729 to 3734 of SEQ ID NO: 1) (the "upstream E-box"), which is known as a potential binding site of the bHLHZ class of transcription factors such as the c-Myc oncoprotein and the upstream stimulatory factor (USF) (Grandori and Eisenman, *Trends Biochem. Sci.*, 22: 177-181, 1997). Thus, the upstream E-box may act as an enhancer of hTERT transcription in at least some cells.

There is another canonical E-box downstream of the major transcription initiation site (+22 to +27 in FIG. 1, corresponding to residues 3937 to 3942 of SEQ ID NO: 1) (the "downstream E-box"). The affect of the downstream E-box on hTERT transcription activity is described in more detail in other examples herein.

Example 5

Role of c-Myc and Other Factors in hTERT Promoter Activity

To demonstrate a role of c-Myc protein in the hTERT gene transcription, a human c-Myc cDNA expression plasmid, RSVmycSVpA (provided by Dr. Chi V. Dang, Johns Hopkins University), or an empty vector (0.5 µg per well) was co-transfected with the hTERT promoter-luciferase constructs described above (0.5 µg per well) and the pRL-SV40 (1 ng per well) into the hTERT mRNA-negative SUSM-1 cells. Cells were cultured for 45 to 48 h after transfection, and cell lysates were prepared and examined by using the Dual luciferase reporter assay system (Promega) and the MLX microtiter plate luminometer (Dynex Technologies, Chantilly, Va.). All the data described in this example were obtained from at least three independent experiments.

As shown in FIG. 4, c-Myc expression markedly induced the luciferase activity when the constructs containing the upstream E-box (pBTdel-408 and pBTdel-208), but not the pGL3-Basic vector and the pBTdel-149 lacking it, were used. This supports the finding that the expression of c-Myc protein positively regulates the hTERT gene transcription, probably through the upstream E-box within the 59-bp region identified above. A slight induction observed in the pBTdel-149 might reflect an indirect effect of c-Myc protein by modulating other regulatory factors.

A 3- to 7-fold increase of the promoter activity by the c-Myc expression in the endogenous hTERT-positive cell lines (data not shown) was also observed. These results support an important role of c-Myc in positive regulation of the hTERT gene expression and telomerase activation.

The results in this example are consistent with the finding that retroviral expression of c-Myc increases the amount of hTERT mRNA and activates telomerase in human mammary epithelial cells and fibroblasts (Wang et al., *Genes Dev.*, 12: 1769-1774, 1998), although that investigation did not include transcriptional regulation of the hTERT gene. Activation of c-Myc is a common target of several oncogenic signals, e.g., mutant p53 proteins (Frazier et al., *Mol. Cell. Biol.*, 18: 3735-3743, 1998), viral oncoproteins (Kinoshita et al., *Virology*, 232: 53-61, 1997), and defects in the APC (adenomatous polyposis coli)/β-catenin pathway (He et al., *Science*, 281: 1509-1512, 1998). One non-limiting hypothesis is that these oncogenic signals converge on the transactivation of the hTERT gene promoter through c-Myc activation as a part of their oncogenic functions. Involvement of other factors is also possible, including other bHLHZ transcription factors such as USF (Grandori and Eisenman, *Trends Biochem. Sci.*, 22: 177-181, 1997), members of the Ets family of oncoproteins, which are known to cooperate with the bHLHZ proteins (Sieweke et al., *EMBO J.*, 17: 1728-1739, 1998), and the AP-2 family of transcription factors.

The second typical E-box downstream of the major transcription initiation site appeared in this example to have only a small, if any, positive regulatory effect on hTERT gene promoter activity in the presence of the upstream E-box (see p2XEB in FIG. 3). It is interesting that the constructs without either E-box (pBTdel-149 and pBTdel-130) still showed low, but significant, promoter activity. Multiple potential binding sites for the Sp1 and MAZ proteins, which function cooperatively at some promoters (Parks and Shenk, *J. Biol. Chem.*, 271: 4417-4430, 1996), may be involved with this basal activity of the hTERT gene promoter. Sp1 binding was observed in the hTERT mRNA-positive cell lines by a supershift on gel mobility shift assay using a 20-bp probe (−117 to −98 in FIG. 1; SEQ ID NO: 13).

Example 6

Construction of Additional hTERT Promoter Constructs and c-Myc and Mad1 Expression Constructs A fragment of the hTERT promoter (−3915 to +40 of FIG. 1; corresponding to residues 1 to 3955 of SEQ ID NO: 1) was amplified by PCR from a BAC (bacterial artificial chromosome) clone containing the hTERT genomic sequence using the methods described in Example 1. The 3955-bp hTERT promoter fragment was inserted into SacI/SmaI sites of the luciferase reporter vector pGL3-Basic (Promega Corp., Madison, Wis.) to generate the pBT-3915 plasmid.

A series of unidirectional truncations from the upstream (pBT-1125, pBT-949, pBT-385, pBT-304, pBT-255, pBT-88 and pBT-33) were generated by endonuclease digestion (SacI plus StuI, PstI, BstEII, BssHII, PvuII, SmaI or SacI, respectively) of the pBT-3915 followed by end-polishing and self-circularization. The pBT-211 (previously named p2XEB), pBTdel-255, pBTdel-208 and pBTdel-130 were constructed as described in Example 3.

To make mutations in the pBT-255 construct, which mutations are described in detail in Example 10 and FIG. 6, the QuikChange Site-Directed Mutagenesis kit (Stratagene Cloning Systems, La Jolla, Calif.) was used according to the supplier's protocol. Artificial hTERT promoters with additional E-box elements (pBT-255-2DEB and pBT-255-4DEB), were constructed using standard techniques with one or three copies of the synthetic DNA (5'-CGCACGTGGG-3' (e.g., residues 314 to 323 of SEQ ID NO: 8); a canonical E-box underlined) placed immediately downstream of the hTERT promoter (into XhoI/HindIII sites) in the pBT-255 plasmid. For c-Myc and Mad1 expression constructs, human c-Myc and Mad1 cDNAs were amplified by reverse transcription-PCR from Marathon-ready human kidney cDNA (Clontech) and inserted into the mammalian expression vector pcDNA3.1 (+) (Invitrogen Corp., San Diego, Calif.). All the plasmids were confirmed to have correct sequences by DNA sequencing.

Example 7

Properties of RCC23, RCC23+3, and Other Cell Lines

In order to demonstrate the transcriptional activity of hTERT promoter fragments in cells with a similar genetic backgrounds, a renal cell carcinoma cell line, RCC23, and its derivative with a transferred copy of normal human chromosome 3, RCC23+3 were used in reporter gene assays described below. RCC23 and RCC23+3 were previously described by Horikawa et al. (*Mol. Carcinog.*, 22: 65-72, 1998), and the properties of these cell lines are summarized in Table 3.

As shown in Table 3, RCC23 is a telomerase-positive cell line, while RCC23+3p is a telomerase-negative cell line. RCC23+3p (clone #3-B in Horikawa et al., *Mol. Carcinog.*, 22: 65-72, 1998) carries a transferred copy of partial human chromosome 3 (entire short arm plus cen-q22) and shows similar phenotypes to RCC23+3 (see Table 3). REV is a revertant clone that emerged from senescent RCC23+3p culture with loss of the transferred 3p22-cen loci and reacquired the phenotypes of parental RCC23 cells (as described in Horikawa et al., *Mol. Carcinog.*, 22: 65-72, 1998, and Horikawa et al., *J. Cell. Biochem.* 82, 415-421, 2001).

TABLE 3

Summary of characteristics of RCC23, RCC23+3, RCC23+3p and REV cells

| Cell | Transferred Chromosome 3[a] | Telomerase Activity[b] | hTERT mRNA[c] | Telomere Length[d] | Life Span |
|---|---|---|---|---|---|
| RCC23 | None | + | + | Maintained | Immortal |
| RCC23+3 | Intact 3 | − | −[e] | Shortens Progressively | Mortal (41 PDs)[f] |
| RCC23+3p | 3pter-q22 | − | −[e] | Shortens Progressively | Mortal (28 PDs)[f] |
| REV | 3pter-p23 3cen-q22 | + | + | Maintained | Immortal |

[a]Transferred by means of microcell fusion.
[b]As determined by TRAP (telomeric repeat amplification protocol) assay.
[c]As determined by conventional reverse transcription (RT)-PCR and quantitative real-time RT-PCR (Taqman) assays.
[d]As determined by terminal restriction fragment length by Southern blot.
[e]At least 64-fold lower expression than RCC23 in Taqman assay.
[f]Senesce at 41 or 28 population doublings (PDs) after microcell fusion.

Normal human fibroblasts (NHF) were derived from neonatal foreskin (Horikawa et al., *J. Cell. Biochem.*, 82, 415-421, 2001). Normal human prostate epithelial cells (PrEC) were obtained from BioWhittaker, Inc. (Walkersville, Md.) and maintained according to the supplier's protocol. Rapidly proliferating NHF and PrEC at early-passage culture were used for the examples described herein. The lack of telomerase activity and hTERT mRNA in NHF and PrEC was confirmed as described previously (Horikawa et al., *Mol. Carcinog.* 22, 65-72, 1998). Other human cell lines that express telomerase activity and hTERT mRNA, which were used in the examples described herein, include: CMV-Mj-HEL-1 (described in Example 4); MCF-7 (breast cancer cell line; obtained from American Type Culture Collection (ATCC), Manassas, Va.); MDA-MB-435 (breast cancer cell line; obtained from ATCC); DU145 (prostate cancer cell line; obtained from ATCC); and TSU-Pr1('T24') (a gift from Dr. Carrie Rinker-Schaeffer, University of Chicago), which has been identified as a bladder cancer cell line (van Bokhoven et al., *Cancer Res.*, 61: 6340-6344, 2001).

Human mammary epithelial cells (strain 184; a gift from Dr. Martha Stampfer, Lawrence Berkeley National Laboratory) and NHF were infected with the LXIN retrovirus containing full-length hTERT cDNA (Carney et al., Lab. Invest., 82719-728, 2002) to produce immortal 184-hTERT and NHF-hTERT cells, respectively Example 8

Luciferase Assays Using Cell Lines Described in Example 7

For luciferase assays using RCC23-derived cell lines (see Table 3), cells ($8.0 \times 10^4$) were seeded on 24-well plates, cultured overnight, and transfected with the hTERT promoter-luciferase plasmids (0.5 µg per well) by using FuGENE6 transfection reagent (Roche Diagnostics, Indianapolis, Ind.). The ratio of DNA:FuGENE6 was 1:3, which resulted in similar transfection efficiencies in RCC23 and RCC23+3 cells. These transfection conditions appeared to be more direct and reliable for these particular cells than the transfection conditions described in Example 4.

The pRL-SV40 (2 ng per well; Promega) driving *Renilla reniformis* luciferase was included in each transfection as a control to normalize the transcriptional activity of hTERT promoter fragments. The expression construct (c-Myc, Mad1 or vector alone; 1.0 µg per well) was included in co-transfection experiments. Preparation of cell lysates and measurement of luciferase activity were performed using Dual luciferase reporter assay system (Promega). All the data collected from luciferase assays described in this Example are expressed as the mean and standard deviation (SD), and were from at least three independent experiments.

Luciferase assays using the other human cell lines described in Example 7 were carried out as described for RCC23-derived cell lines, except the other human cells were seeded at $6.0 \times 10^4$ to $1.2 \times 10^5$/well depending on cell size and growth rate.

Example 9

A Sequence Downstream of the Transcription Initiation Site is Responsible for Differential hTERT Transcription Between RCC23 and RCC23+3 Cells Transcriptional activity of the 3955-bp hTERT promoter fragment (−3915 to +40 in FIG. 1, corresponding to residues 1 to 3955 of SEQ ID NO: 1; construct pBT-3915) and the series of 5'-deleted fragments (from position −X to +40; constructs pBT-X's) described in Example 6 was demonstrated in a luciferase assay using RCC23 and RCC23+3 cells as the recipients. As shown in FIG. 5, the 3955-bp fragment (pBT-3915) showed an approximately 8-fold higher activity in RCC23 than in RCC23+3, which supports the finding that the difference in hTERT mRNA expression between these two cells can be attributed largely to differential transcription from the hTERT promoter.

The data from the series of 5'-deleted promoter fragments support the contributions of some known factors to hTERT transcriptional control. Specifically, the increase in the luciferase activity with the deletion of −949 to −386 (compare pBT-949 and pBT-385 in FIG. 5) is consistent with the function of MZF2 repressor and its binding sites within this region (Fujimoto et al., *Nucleic Acids Res.*, 28: 2557-2562, 2000). The marked decrease with the deletion of −211 to −34 (compare pBT-211, pBT-88 and pBT-33 in FIG. 5) can be attributed to transcriptional activation mediated by multiple Sp1 binding sites as previously reported (Kyo et al., *Nucleic Acids Res.*, 28: 669-677, 2000).

However, a significant difference between RCC23 and RCC23+3 was observed for all of the 5'-deleted promoter fragments tested, as shown by the consistently high RCC23/RCC23+3 ratio (e.g., 4.2 to 8.3) shown in FIG. 5. These findings indicated that transcriptional regulators binding to the region of interest (−3915 to −34 in FIG. 1, corresponding to residues 1 to 3882 of SEQ ID NO: 1), such as MZF2 and Sp1, control hTERT transcription in both RCC23 and RCC23+3 cells but were not critical to the differential hTERT transcription observed between the two cell lines. It is also unlikely that the upstream E-box element (−187 to −182 in FIG. 1, corresponding to residues 3729 to 3734 of SEQ ID NO: 1) is responsible for the differential transcription, because the deletion containing this E-box (compare pBT-211 and pBT-88) did not abrogate the difference between RCC23 and RCC23+3.

The activity of hTERT promoter fragments with a 35-bp deletion (+6 to +40 in FIG. 1, corresponding to residues 3921 to 3955 of SEQ ID NO: 1) downstream of the transcription initiation site were tested. All three constructs with this deletion (constructs pBTdel-255, pBTdel-208 and pBTdel-130 in FIG. 5) exhibited comparable hTERT promoter activities in both RCC23+3 and RCC23 cells, with RCC23/RCC23+3 ratios of 1.2 or 1.3. These ratios are significantly lower than the ratio observed with constructs containing the 35-bp sequence. Notably, the deletion of the downstream sequence resulted in an approximately 2-fold increase in the transcriptional activity in RCC23+3, while it resulted in an approximately 40% decrease in RCC23 (compare pBT-255 and pBTdel-255). These results support the finding that the region downstream of the transcription initiation site contains a DNA element or elements that contribute to the differential control of hTERT transcription in RCC23 versus RCC23+3 cells.

Example 10

Downstream E-Box Contributes to the Differential Control of hTERT Transcription

To demonstrate which sequences contribute to the differential control of hTERT transcription observed in Example 9, a series of mutations within the 35-bp downstream sequence (+6 to +40 in FIG. 1, corresponding to residues 3921 to 3955 of SEQ ID NO: 1) were created by site-directed mutagenesis of the construct pBT-255 (see mut#1-#6 in FIG. 6). The specific mutations are shown in FIG. 6.

Four out of the 6 mutant promoter fragments (mut#1, #3, #5 and #6) showed similar transcriptional activities to that of the wild-type promoter in both RCC23 and RCC23+3 cells. In one mutant (mut#2), an approximately 65% decrease in the promoter activity in both RCC23 and RCC23+3 was observed, implying the presence of a novel DNA element involved in the activation of hTERT transcription; however, the difference between RCC23 and RCC23+3 was maintained in this mutant. Mutation of the downstream E-box (mut#4) resulted in an approximately 50% decrease in promoter activity in RCC23, while producing an approximately 2-fold increase in promoter activity in RCC23+3 (RCC23/RCC23+3 ratio=1.3), an effect similar to that observed with promoter fragments lacking the 35-bp downstream sequence. In contrast, when the upstream E-box (−187 to −182 in FIG. 1, corresponding to residues 3729 to 3734 of SEQ ID NO: 1) was mutated (mut#7), no significant change in the promoter activity was observed in either RCC23 or RCC23+3, showing that the upstream E-box has no or little contribution to hTERT transcription in these cells. In the presence of this upstream E-box mutation, the downstream E-box mutation (mut#4+7) again failed to show the difference between RCC23 and RCC23+3.

These results identify the E-box located downstream of the transcription initiation site as an important cis-acting DNA element in determining the differential hTERT promoter activity, and indicate that this E-box element is involved in both activation and repression of the hTERT transcription in RCC23 and RCC23+3, respectively.

To further demonstrate the downstream E-box-mediated regulation of the hTERT transcription, one or three copies of synthetic E-box sequences were inserted downstream of the wild-type promoter (2 or 4 copies of downstream E-boxes in total; as shown in FIG. 7). The extra copies of E-boxes did not affect the promoter activity in RCC23, implying that the E-box-mediated, activating mechanism is fully active with the single endogenous copy of E-box in this cell line. In contrast, a copy number-dependent repression of the promoter activity was observed in RCC23+3, resulting in a more obvious difference in the promoter activity between RCC23 and RCC23+3.

This result does not favor (but does not rule out) the notion that an absence or inactivation of E-box-binding activator(s) is primarily responsible for the repressed hTERT transcription in RCC23+3. Instead, it supports (without being limited to) the existence of an E-box-mediated repressive mechanism that actively functions in RCC23+3 and is defective in RCC23.

Example 11

The Downstream E-Box-Mediated Repression Correlates with the Presence of a Transferred Chromosome 3

To demonstrate the effect of the transferred copy of human chromosome 3 on regulation of hTERT transcription mediated by the downstream E-box element, the activity of wild-type, E-box mutant and synthetic E-box-containing hTERT promoter fragments was determined in a second pair of RCC23-derived cells: RCC23+3p, telomerase/hTERT-negative cells with the transferred partial chromosome 3 (3pter-3q22); and REV, a telomerase/hTERT-expressing revertant clone that emerged from RCC23+3p with loss of 3p22-cen region from the transferred chromosome (as summarized in Table 3).

As shown in FIG. 8, RCC23+3p showed the same results as RCC23+3 for all the fragments examined: approximately 5-fold repression compared with RCC23 in the wild-type promoter (pBT-255); an approximately 2-fold increase with the downstream E-box mutation (mut#4); and enhancement of the repression in an E-box copy number-dependent manner (pBT-255-2DEB and pBT-255-4DEB). In contrast, the activities of these four promoter fragments in REV cells were similar to those observed in RCC23, showing an approximately 50% reduced activity of the E-box mutant fragment and no significant change by the addition of synthetic E-box sequences.

Thus, as observed in RCC23+3 and RCC23, the difference in hTERT promoter activity between RCC23+3p and REV was abrogated by the E-box mutation and became greater with the increased E-box copy number. These findings show that loss of the transferred chromosome 3p22-cen in the hTERT-repressed cells results in reversion to the hTERT-expressing cells, which is consistent with the previous mapping of a telomerase repressor gene on 3p21-p14.2 (Tanaka et al., *Genes Chromosomes Cancer,* 23: 123-133, 1998). One possible non-limiting mechanism for the results described in this Example is that downstream E-box-mediated repression of hTERT transcription depends on the function of a gene on the transferred human chromosome 3.

Example 12 c-Myc and Mad1 can Modulate hTERT Promoter Activity When Overexpressed but are not the Causative Factors in Differential hTERT Transcription in RCC23 and RCC23+3

Previous work indicated that the transcription factors c-Myc and Mad1, which have an ability to bind canonical E-box elements, can activate and repress hTERT promoter activity, respectively (e.g., Greenberg et al., *Oncogene,* 18: 1219-1226, 1999). The effects of these factors in RCC23 and RCC23+3 were demonstrated by cotransfecting c-Myc and Mad1 expression plasmids with the luciferase plasmids pBT-255 or its E-box mutants.

As shown in FIG. 9, forced expression of c-Myc protein enhanced the activity of the wild-type hTERT promoter in RCC23+3, but had little or no effect in RCC23. It is likely that the overexpressed c-Myc protein can abrogate the repressive mechanism functioning in RCC23+3. The inability of the overexpressed c-Myc to further enhance the promoter activity in RCC23 supports a threshold response for the hTERT transcriptional activation.

FIG. 9 also shows that overexpressed Mad1 protein decreased the transcriptional activity of the wild-type promoter in both RCC23 and RCC23+3 (an approximately 70% reduction in both), consistent with its repressive effect on the hTERT transcription as indicated by others (e.g., Günes et al., *Cancer Res.,* 60: 2116-2121, 2000). Results from the promoter fragments mutated at either downstream or upstream E-box or at both (mut#4, #7 and #4+7, respectively) showed that both activation by c-Myc expression and repression by Mad1 expression were mediated primarily by the downstream E-box element (see FIG. 9).

Example 13

Western Blot Analysis of Endogenous c-Myc and Mad1 Protein

This example demonstrates by Western blot analysis that the expression level or activity of endogenous c-Myc or Mad1 is not a determinant of the differential hTERT transcription in RCC23 and RCC23+3.

Forty μg of protein were resolved on 10% polyacrylamide gels and transferred to a nitrocellulose membrane (Hybond- ECL, Amersham Pharmacia Biotech, Inc., Piscataway, N.J.) or a PVDF membrane (Immobilon P, Millipore, Corp., Bedford, Mass.). Blocking and incubation of the membranes with primary and secondary antibodies followed the suppliers' instructions. Protein bands were detected using the ECL western blotting detection system (Amersham Pharmacia Biotech, Inc.). The following antibodies were from Santa Cruz Biotechnology, Inc. (Santa Cruz, Calif.): c-Myc (sc-764), Mad1 (sc-222), Max (sc-197), USF1 (sc-229) and USF2 (sc-861).

As shown in FIG. 10, RCC23 and RCC23+3 expressed similar amounts of endogenous c-Myc and Mad1 proteins, which is consistent with the previous finding that a transferred chromosome 3 did not affect the expression levels of these proteins in 21NT breast carcinoma cells (Ducrest et al., *Cancer Res.*, 61: 7594-7602, 2001). Moreover, neither of the proteins was detected in the major E-box binding complexes in either RCC23 or RCC23+3 under the conditions described herein (as shown by gel shift assays described in Example 14). Thus, the expression level or activity of endogenous c-Myc or Mad1 is not a determinant of the differential hTERT transcription in RCC23 and RCC23+3.

Example 14

Detection of Endogenous Protein Factors that Bind the Downstream E-Box Element by Gel Mobility Shift Assay To demonstrate protein factors that bind the downstream E-box element, a gel mobility shift assay was performed using the whole cell extracts of RCC23 and RCC23+3. Whole cell extracts were prepared from exponentially growing cells as previously described (Mudryj et al., Cell, 65: 1243-1253, 1991). Three (3) µg of protein was incubated with $^{32}$P-labeled double-stranded oligonucleotide at room temperature for 20 min in the binding buffer: 20 mM Hepes (pH 7.4), 1 mM $MgCl_2$, 0.1 mM EDTA, 40 mM KCl, 0.5 mM DTT, 1 µg of sonicated salmon sperm DNA, 60 µg of bovine serum albumin, 1% Ficoll. DNA-protein complexes were resolved on a 4% polyacrylamide gel at 4° C. For supershift of the complexes, whole cell extracts were pre-incubated with the indicated antibodies prior to addition of $^{32}$P-labeled oligonucleotides. The following sequences were used as probes: CG CACGTGGG (SEQ ID NO: 10); canonical E-box underlined), GCTGCGCACGTGGGAAGCCC (SEQ ID NO: 11); canonical E-box underlined), GCTGCG CACCCGGGAAGCCC (SEQ ID NO: 12); mutated E-box underlined) and GCGGACCCCGCCCCGTCCCG (SEQ ID NO: 13); consensus Sp1 binding site underlined).

The result with the 10-bp probe containing the downstream E-box (SEQ ID NO: 10) is shown in FIG. 11. Antibodies to the E-box-binding proteins USF1, c-Myc, Mad1 and Max were included in the binding reactions to detect binding of these proteins. The major shifted bands were supershifted by pre-incubating the extracts with the USF1 antibody (lanes 2 and 7 in FIG. 11). These bands may represent a USF1/USF1 homodimer and a USF1/USF2 heterodimer. No significant difference was observed in the binding of USF complexes between RCC23 and RCC23+3, consistent with similar amounts of USF1 and USF2 proteins in these two cell lines as shown by western blot analysis (see FIG. 10 and Example 13). Neither c-Myc antibody nor Mad1 antibody changed the profile of shifted bands (lanes 3, 4, 8 and 9 in FIG. 11). By addition of the Max antibody, a slowly migrating, faint band was supershifted (lanes 5 and 10 in FIG. 11). Thus, binding of c-Myc or Mad1 to the E-box element was not evident in either RCC23 or RCC23+3. Another E-box binding protein, which remains to be identified, may form a complex with Max to bind the E-box element in both RCC23 and RCC23+3.

A shifted band (marked by the asterisk in FIG. 11) was observed in RCC23+3 but not in RCC23. This band was not supershifted by any of the antibodies tested and became more evident after supershift of co-migrating USF complexes (compare lanes 2 and 7). This DNA-protein complex appears to be relatively unstable because the salt concentration in the binding buffer and the electrophoresis conditions affect its detection.

The 20-bp probe containing the downstream E-box (+16 to +35 in FIG. 1; SEQ ID NO: 1), but not the 20-bp probe with the E-box mutated, detected similar profiles of binding including the common USF complexes and the RCC23+3-specific factor (data not shown). These findings support the presence of an E-box binding factor specific to hTERT-negative cells that affects the transcriptional control of the hTERT gene.

Example 15

The Downstream E-Box Acts as a Negative Regulatory Element in Normal Human Cells but not in Telomerase/hTERT-Positive Cells The repressive mechanism mediated by the downstream E-box element functions was tested in other types of normal and immortal human cells.

As shown in FIG. 12A, the mutation of the downstream E-box (mut#4) resulted in 2.5-fold and 1.9-fold increase in hTERT promoter activity in normal human fibroblasts (NHF) and prostate epithelial cells (PrEC), respectively, as compared with the wild-type hTERT promoter fragment (pBT-255) in those same cell types. This data supports the finding that the downstream E-box acts as a negative regulatory element in these normal human cells, like in RCC23+3.

A similar increase in hTERT promoter activity with the E-box mutation was also observed in retroviral hTERT-immortalized NHF (NHF-hTERT) and mammary epithelial cells (184-hTERT). The NHF-hTERT and 184-hTERT cells, as well as normal human cells (NHF and PrEC), showed much lower activity (one twentieth to one hundredth) of the wild-type hTERT promoter than the other immortalized and cancer cell lines. It is therefore most likely that, in these retroviral hTERT-immortalized cells, the transcription of the endogenous hTERT gene remains tightly repressed and the E-box-mediated repressive mechanism still functions.

In contrast, an immortalized fibroblast cell line CMV-Mj-HEL-1 and breast cancer cell lines MCF-7 and MDA-MB-435 showed no change or a statistically insignificant decrease in the promoter activity with the E-box mutation (see FIG. 12A), which supports the finding that the E-box-mediated repressive mechanism is inactive in these immortal, endogenous telomerase/hTERT-positive cells, like in RCC23.

However, in prostate cancer DU145 and bladder cancer TSU-Pr1 ('T24') cells, the E-box element still appeared to be able to negatively regulate hTERT transcription (FIG. 12A). Thus, it is possible that the downstream E-box-mediated repressive mechanism is active in various cell types and becomes inactivated in some, but not all, cases of human cell immortalization and carcinogenesis.

As shown in FIG. 12 B, normal and retroviral hTERT-immortalized cells of fibroblastic or epithelial origin (NHF, PrEC, NHF-hTERT and 184-hTERT) showed the enhancement of repression of the hTERT transcription in an E-box copy number-dependent manner, as observed in RCC23+3 cells. This copy number-dependent effect was not observed in MCF-7 breast cancer cells (similarly to RCC23 and in contrast to 184-hTERT of breast epithelial origin), while it was evident in DU145 prostate cancer cells (similarly to PrEC).

These results demonstrated that synthetic copies of E-box element placed downstream of the hTERT promoter resulted in the tighter repression in the telomerase-negative RCC23+3 and normal human cells of fibroblastic and epithelial origins, while maintaining the high activity in most telomerase-positive cancer cells (i.e., RCC23 and MCF-7). The artificial hTERT promoters described herein should minimize the cytotoxicity in normal cells without loss of cytotoxic effect on cancer cells when they are used to drive the expression of cytotoxins in anti-cancer therapy.

Example 16

Cancer-Specific Expression of Artificial hTERT Promoter

This example describes cancer-cell-specific expression of a reporter construct (i.e., green fluorescent protein; GFP) directed by an artificial hTERT promoter in a lentivirus vector construct.

The lentivirus vector used in this example (pSGT-5(SDM/RRE2/hTERT-GFP)) is based on a human immunodeficiency virus type 2 (HIV-2) lentiviral vector system described by D'Costa et al., *J. Gen. Virol.*, 82: 425-434, 2001, which is incorporated herein by reference. The pSGT-5(SDM/RRE2/hTERT-GFP) construct has the general structure shown schematically in FIG. 13.

The activity of pSGT-5(SDM/RRE2/hTERT-GFP) was tested in the following telomerase-positive, cancer or immortalized cell lines: 293T (immortalized human embryonic kidney cells), RKO (colon carcinoma cells), MCF-7 (breast carcinoma cells), SK-OV-3 (ovarian carcinoma cells), and RCC23 (renal cell carcinoma cells). The activity of pSGT-5 (SDM/RRE2/hTERT-GFP) was further tested in the following telomerase-negative cells: Normal human fibroblasts, and RCC23+3 (RCC23 cells with a transferred normal human chromosome 3).

Human epitheloid 293T cells were transfected with pSGT-5(SDM/RRE2/hTERT-GFP), together with the helper packaging clones pCM-ROD(SD36/EM) and pCM-VSV-G (see, D'Costa et al., *J. Gen. Virol.*, 82: 425-434, 2001), using the calcium phosphate protocol (Arya and Gallo, *Proc. Natl. Acad. Sci.*, 85: 9753-9757, 1988; Arya and Sadaie, *J. Acquir. Immune. Defic. Syndr.*, 6: 1371-1380, 1993). Typically, $1 \times 10^6$ cells from subconfluent monolayer were transfected with 10 μg of the pSGT-5(SDM/RRE2/hTERT-GFP) vector DNA and 4-10 μg of the cotransfecting plasmid DNAs. Cultures were incubated with calcium-DNA aggregates overnight, washed and reincubated with fresh medium. Cells and culture supernatant were harvested 3 days after transfection.

To demonstrate the expression pattern of the pSGT-5 (SDM/RRE2/hTERT-GFP) construct among the examined cell types, $1.0-2.0 \times 10^5$ of each of 293T, RKO, MCF-7, SK-OV-3, RCC23, normal human fibroblasts, and RCC23+3 cells were separately incubated with approximately $1.0 \times 10^6$ TU of infective particles for 48 or 72 hours. The transduced cells were then observed under a Leica DM IRB microscope equipped with a GFP filter. As indicated in Table 4, GFP fluorescence was observed in each of the telomerase-positive, cancer or immortalized cell lines; however, no fluorescence was observed in normal human fibroblasts or RCC23+3 cells.

TABLE 4

GFP Fluorescence in Cells Transduced With Lentiviral Vector

| Cell Type | GFP Observed |
|---|---|
| 293T | + |
| RKO | + |
| MCF-7 | + |
| SK-OV-3 | + |
| RCC23 | + |
| Normal human fibroblasts | − |
| RCC23+3 | − |

These results show that a lentiviral vector containing an artificial TERT promoter may be packaged into an infectious particle, which in turn may be used to transduce a variety of cell types. Moreover, the artificial TERT promoter contained in the lentiviral construct successfully directs cell-specific expression of an operably linked heterologous nucleic acid sequence, i.e., GPF. Specifically, the expression of GFP under the control of the artificial TERT promoter is observed, e.g., in several cancer cell lines, but not in normal human fibroblasts.

Example 17

In vivo Cancer-Specific Expression of Artificial TERT Promoter Vectors

To demonstrate the expression of an artificial TERT promoter in vivo, immune-deficient mice models (e.g., SCID mice or nude mice) may be used. For example, SCID mice are injected intraperitoneally (i.p.) with approximately $5 \times 10^6$ logarithmically growing cancer cells, e.g., R⁻ cancer cells, in a small volume of sterile saline solution. After several days, e.g., 3, 6, and 9 days, the mice are injected i.p. with either an effective amount of infectious particles (e.g., $3 \times 10^6$ TU in 0.5 ml sterile saline) containing a reporter gene under the control of an artificial TERT promoter, such the lentiviral vector pSGT-5(SDM/RRE2/hTERT-GFP) described in Example 16, or a control solution, such as sterile saline. Tumor growth is monitored daily in experimental and control mice, e.g., by palpation or other technique known in the art. After a sufficient time to permit tumor growth and vector transduction (e.g., about 10 days, about 2 weeks, about 20 days, or about 3 weeks), mice are sacrificed and the expression of the reporter gene measured in cancer cells and normal, surrounding tissues. For example, GFP expression in tumor and normal cells can be determined by a variety of fluorescence microscopy techniques known in the art. For a more detailed discussion of similar techniques, see, e.g., Indraccolo, et al., *Cancer Res.* 62: 6099-6107, 2002.

Example 18

Cytotoxin Expression Under the Control of an Artificial TERT Promoter for Cancer Treatment Viral vectors, such as the lentiviral vector described in Example 16, may be engineered using ordinary techniques in the art to place the expression of a cytotoxin, such as the Bax gene, under the control of an artificial TERT promoter. For example, the GFP open reading frame (ORF) may be excised from pSGT-5(SDM/RRE2/hTERT-GFP) and replaced with a nucleic acid sequence encoding a cytotoxin, such as the Bax gene. Using methods such as those described in Example 17 and described, e.g., in Gu et al., *Oncogene,* 21: 4757-4764, 2002, a therapeutically effective amount of infectious particles carrying the cytotoxic nucleic acid sequence under the control of the artificial TERT promoter is administered to immune-deficient mice carrying either intraperatoneal or subcutaneous tumors induced by appropriate injection of R⁻ cancer cells. Tumor size and progression is monitored in experimental and control animals. Because differential expression of the heterologous nucleic acid sequence, e.g., cytotoxic nucleic acid sequence, operably linked to the artificial TERT promoter is enhanced as a result of preferential suppression of transcription in normal cells, the side effects attributable to expression of the cytotoxic nucleic acid sequence are minimized in normal cells without sacrificing high levels of expression in R⁻ cancer cells.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. A regulatory control sequence comprising: a human telomerase reverse transcriptase (TERT) promoter, wherein said promoter comprises at least the E-box set forth at residues 3937-3942 of SEQ ID NO: 1, wherein said E-box is located downstream of the transcription initiation site, and further comprising at least one exogenous E-box element linked in cis with and located following the 3' end of the TERT promoter; wherein the TERT promoter directs differential expression of an operably linked heterologous nucleic acid sequence in cancer cells as compared to normal cells; and wherein the presence of the at least one exogenous E-box element decreases the expression of the heterologous nucleic acid sequence operably linked to the regulatory control sequence in the normal cells without substantially decreasing the expression of the heterologous nucleic acid sequence in the cancer cells.

2. The regulatory control sequence of claim 1, wherein the TERT promoter comprises a nucleic acid sequence selected from the group consisting of: (a) residues 1-3955 of SEQ ID NO: 1; residues 2791-3955 of SEQ ID NO: 1; residues 2967-3955 of SEQ ID NO: 1; residues 3531-3955 of SEQ ID NO: 1; residues 3612-3905 of SEQ ID NO: 1; residues 3661-3955 of SEQ ID NO: 1; residues 3705-3955 of SEQ ID NO: 1; residues 3828-3955 of SEQ ID NO: 1; and residues 3883-3955 of SEQ ID NO: 1; and (b) a nucleic acid sequence having at least 95% sequence identity with any one of the nucleic acid sequences in (a), wherein said nucleic acid comprises at least the E-box set forth at residues 3937-3942 of SEQ ID NO: 1, and wherein said E-box is located downstream of the transcription initiation site.

3. The regulatory control sequence of claim 1, comprising more than one exogenous E-box element.

4. The regulatory control sequence of claim 3, comprising three exogenous E-box elements.

5. The regulatory control sequence of claim 1, having the structure 5'-TERT promoter comprising the downstream E-box-(exogenous E-box)$_n$-3', wherein "n" is any integer equal to or greater than two.

6. The regulatory control sequence of claim 1, further comprising a heterologous nucleic acid sequence operatively linked thereto.

7. The regulatory control sequence of claim 6, wherein the heterologous nucleic acid sequence encodes a cytotoxin or a therapeutic substance.

8. The regulatory control sequence of claim 6, having the structure 5'-TERT promoter comprising the downstream E-box-(exogenous E-box)$_n$-heterologous sequence-3', wherein "n" is any integer equal to or greater than one.

9. The regulatory control sequence of claim 1, comprising the nucleic acid sequence set forth as SEQ ID NO: 8 or SEQ ID NO: 9.

10. An expression vector comprising the regulatory control sequence of claim 1.

11. The vector of claim 10, wherein the vector is a viral vector.

12. The vector of claim 10, wherein the vector is a plasmid vector.

13. An isolated host cell transformed with the vector of claim 10.

14. The isolated host cell of claim 13, wherein the host cell is a eukaryotic cell.

15. The isolated host cell of claim 13, wherein the host cell is a prokaryotic cell.

16. An expression vector comprising the regulatory control sequence of claim 7.

17. The regulatory control sequence of claim 2, wherein the nucleic acid sequence of (b) has at least 98% sequence identity with any one of the nucleic acid sequences in (a), wherein said nucleic acid comprises at least the E-box set forth at residues 3937-3942 of SEQ ID NO: 1, and wherein said E-box is located downstream of the transcription initiation site.

\* \* \* \* \*

UNITED STATES PATENT AND TRADEMARK OFFICE
CERTIFICATE OF CORRECTION

| | | |
|---|---|---|
| PATENT NO. | : 7,598,077 B2 | Page 1 of 1 |
| APPLICATION NO. | : 10/456830 | |
| DATED | : October 6, 2009 | |
| INVENTOR(S) | : Horikawa et al. | |

It is certified that error appears in the above-identified patent and that said Letters Patent is hereby corrected as shown below:

On the Title page,

[*] Notice:  Subject to any disclaimer, the term of this patent is extended or adjusted under 35 USC 154(b) by (1216) days Delete the phrase "by 1216 days" and insert -- by 1811 days --

In the Specification:

Column 36, line 19: "with a similar" should read -- with similar --

Column 37, line 20: "respectively" should read -- respectively. --

In the Claims:

Claim 2 at Column 57, line 40: "3612-3905" should read -- 3612-3955 --

Signed and Sealed this

First Day of June, 2010

David J. Kappos
*Director of the United States Patent and Trademark Office*